United States Patent
Pegoraro

(10) Patent No.: US 8,343,963 B2
(45) Date of Patent: Jan. 1, 2013

(54) SULFAMOYL-PHENYL-UREIDO COMPOUNDS AND THEIR USE AS MEDICAMENT

(75) Inventor: Stefano Pegoraro, Planegg-Martinsried (DE)

(73) Assignee: 4SC AG, Planegg-Martinsried (DE)

( * ) Notice: Subject to any disclaimer, the term of this patent is extended or adjusted under 35 U.S.C. 154(b) by 166 days.

(21) Appl. No.: 12/696,479

(22) Filed: Jan. 29, 2010

(65) Prior Publication Data

US 2010/0197640 A1 Aug. 5, 2010

Related U.S. Application Data

(60) Provisional application No. 61/148,617, filed on Jan. 30, 2009.

(51) Int. Cl.
| | | |
|---|---|---|
| *A61K 31/5375* | (2006.01) | |
| *A61K 31/541* | (2006.01) | |
| *A61K 31/495* | (2006.01) | |
| *A61K 31/17* | (2006.01) | |
| *C07C 311/47* | (2006.01) | |
| *C07D 207/09* | (2006.01) | |
| *C07D 211/22* | (2006.01) | |
| *C07D 211/62* | (2006.01) | |
| *C07D 213/36* | (2006.01) | |
| *C07D 215/42* | (2006.01) | |
| *C07D 277/04* | (2006.01) | |
| *C07D 279/12* | (2006.01) | |

(52) U.S. Cl. ............ 514/227.5; 514/238.5; 514/252.12; 514/253.01; 514/254.1; 514/255.01; 514/327; 514/331; 514/365; 514/422; 514/428; 514/597; 544/58.2; 544/59; 544/169; 544/360; 544/374; 544/389; 544/400; 546/231; 548/146; 548/518; 548/578; 564/49

(58) Field of Classification Search .................... None
See application file for complete search history.

(56) References Cited

U.S. PATENT DOCUMENTS 6,284,772 B1 * 9/2001 Pitzer et al. .................... 514/308
6,949,567 B2 * 9/2005 Aschenbrenner et al. .... 514/309

OTHER PUBLICATIONS

Vippagunta et al Advanced Drug Delivery Reviews, vol. 48, pp. 3-26 (2001).*
Leban et al. Bioorganic & medicinal Chemistry Letters vol. 14, p. 1979-1982 (2004).*

* cited by examiner

*Primary Examiner* — Emily Bernhardt
(74) *Attorney, Agent, or Firm* — Millen, White, Zelano & Branigan, P.C.

(57) ABSTRACT

The present invention relates to novel sulfamoyl-phenyl-ureido compounds having the formula (I) or a physiologically acceptable salt or derivative thereof which are suitable for the therapy of infections caused by protozoa and in particular uncomplicated or severe malaria caused by plasmodia.

formula (I)

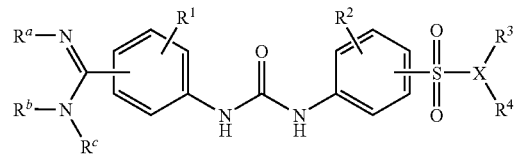

24 Claims, No Drawings

SULFAMOYL-PHENYL-UREIDO COMPOUNDS AND THEIR USE AS MEDICAMENT

This application claims the benefit of the filing date of U.S. Provisional Application Ser. No. 61/148,617 filed Jan. 30, 2009, which is incorporated by reference herein.

The present invention relates to compounds which are suitable for the therapy of infections caused by protozoa and in particular uncomplicated or severe malaria caused by plasmodia.

Malaria is a life-threatening parasitic disease transmitted from person to person through the bite of a female *anopheles* mosquito (Tuteja R.; Malaria—an overview. *FEBS J.*, 274 (2007), 4670-4679). The disease is a public health problem in more than 90 countries and more than 2 billion people are at risk, most of them living in tropical Africa. High risk groups include children, pregnant women, migrant workers and tourist or business travellers entering into endemic areas (Snow R. W., et al.; The global distribution of clinical episodes of *Plasmodium falciparum* malaria. *Nature* 434 (2005), 214-217). A resurgence of this serious disease is currently registered. It is caused by several factors such as increased drug resistance by the parasites, increased mosquito resistance to insecticide, demographic or environmental changes caused by the human population.

By far, the most important factor for malaria resurgence in sub-Saharan Africa and Southeast Asia is the development of resistance by *Plasmodium falciparum* to the cheap and effective drugs in use, notably chloroquine and sulfadoxine/pyrimethamine. Lethal *Plasmodium falciparum* strains resistant to amodiaquine, mefloquine, and quinine have been observed as well (Hyde J. E.; Drug-resistant malaria—an insight. *FEBS J.*, 274 (2007), 4688-4698). At this time, the recommended new treatments for malaria in these parts of the globe are the so-called ACT (artemisinine-based combination therapy) which combines the rapid effect of an artemisinin compound with a longer-half-life drug selected from a pool of known drugs. For example Coartem® combines arthemether and lumefantrine whereas Coarsucam® combines artesunate and amodiaquine; other drugs of this type are currently being released or at late clinical development stage (Wells T. N. C., et al.; New medicines to improve control and contribute to the eradication of malaria. *Nature Reviews Drug Discovery*, 8 (2009), 879-891). The World Health Organization (WHO) has recently endorsed ACT as the "policy standard" for all malaria infections in areas where *Plasmodium falciparum* is the predominant infecting species. The large use of ACT and the positive results registered reinforces the hopes to achieve, within the next years, the goal of controlling the spread of malaria.

In 2007 the Bill and Melinda Gates Foundation called for a renewed global effort to eradicate malaria worldwide (Mills A., et al.; Malaria eradication: the economic, financial and institutional challenge. *Malaria Journal*, 7(Suppl 1):S11 (2008)). Initiatives to eliminate malaria are critically dependent on the efficacy of these ACT therapies. Unfortunately, there is recent worrying evidence that artemisinin resistance has arisen at the That-Cambodian border (Dondrop A. M., et al.; Artemisinin Resistance in *Plasmodium falciparum* Malaria. *New England Journal of Medicine*, 361 (2009) 455-467). The That-Cambodian border area is historically the source of the global diaspora of anti-malarial drug resistance. Resistance to chloroquine and sulphadoxine-pyrimethamine in *Plasmodium falciparum* originated there, spread across Asia and Africa, and caused millions of deaths.

Clearly, to achieve the goal of malaria control and eradication, antimalaria drug discovery must continue working on the development of new medicines to treat malaria, mainly targeting the asexual blood stages of the parasite. Preferentially these new drugs should possess a mode of action diverse from all known and used drugs to prevent the phenomenon of resistance and to open the possibility to combined therapies.

We discovered diaryl-urea compounds which possess anti-parasite properties (Leban J., et al.; Sulfonyl-phenyl-ureido benzamidines: a novel structural class of potent antimalarial agents. *Bioorganic & Medicinal Chemistry Letters*, 14 (2004), 1979-1982.; Aschenbrenner A., et al.; Derivatives of diphenylurea, diphenyloxalic acid diamide and diphenylsulfuric acid diamide and their use as medicaments. PCT Int. Appl. (2002) WO 02/070467). Several of these compounds were able to kill a chloroquine-resistant strain of *Plasmodium falciparum*, cultured in vitro. Unfortunately, these compounds lack the ability to clear completely the parasites from circulating blood of infected animal models and this was attributed to the poor physico-chemical and pharmacokinetic properties. Unexpectedly we found a new class of compounds with improved absorption, distribution, metabolism, and excretion ("ADME") properties as well as better physico-chemical characteristics, which still displayed high antiparasite and antimalaria activity most likely with a new mechanism of action.

The present invention relates to compounds of the formula (I):

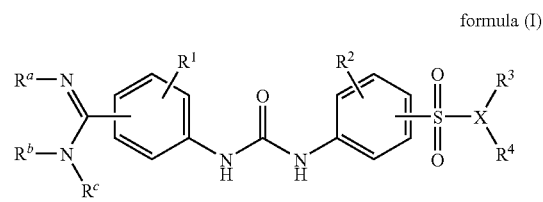

formula (I)

or a physiologically acceptable salt or derivative thereof, wherein $R^a$ is hydrogen, alkyl, alkoxy, hydroxyl, hydroxyalkyl, alkoxyalkyl, —OCOR', —C(O)R', —CONHR' or —CO$_2$R';

$R^b$ and $R^c$ independently are alkyl, alkoxy, hydroxyl, hydroxyalkyl, alkoxyalkyl, aminoalkyl, alkylaminoalkyl, haloalkyl, cycloalkyl, aryl and heteroaryl, heterocyclyl or —CO$_2$R';

or $R^b$ forms together with $R^c$ a 3-, 4-, 5-, 6- or 7-membered saturated, partially unsaturated or entirely unsaturated heterocyclic ring selected from the group consisting of cycloalkyl, aryl, heterocycloalkyl and heteroaryl which optionally has 0, 1, 2 or 3 substituents R", where chemically appropriate, two R" taken together can form a group =O; this heterocyclic group is preferably selected from the group consisting of piperidinyl, piperazinyl, morpholinyl, pyrrolidinyl, thiazolidinyl, thiomorpholinyl, piperidin-4-one-1-yl, S,S-dioxo-thio-morpholinyl, piperazin-3-one-1-yl, or azepanyl R' independently represents hydrogen, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, amino, aminoalkyl, alkylamino, alkoxy, —OH, —SH, alkylthio, hydroxyalkyl, hydroxyalkylamino, halogen, haloalkyl, haloalkoxy, aryl, haloaryl, haloarylalkyl, arylalkyl, heterocyclyl or heteroaryl;

R" is independently hydrogen, —$(CH_2)_mR'$, —$CO_2R'$, —$CON(R')_2$, —CR'O, —$SO_2N(R')_2$, —NR'-CO-haloalkyl, —$NO_2$, —$NR'$-$SO_2$-haloalkyl, —$NR'$-$SO_2$-alkyl, —$NR'$-$SO_2$-aryl, —$NR'$-$SO_2$-heteroaryl, —$SO_2$-alkyl, —$SO_2$-aryl, —$SO_2$-heteroaryl, —NR'—CO-alkyl, —NR'—CO-aryl, —NR'—CO-heteroaryl, —NR'—CO—$N(R')_2$, —CN, alkyl, amino, amide, cycloalkyl, aminoalkyl, alkylamino, alkoxy, alkoxyalky, hydroxyl, —SH, alkylthio, hydroxyalkyl, hydroxyalkylamino, halogen, haloalkyl, haloalkoxy, aryl, arylalkyl or heteroaryl; where chemically appropriate, two R" taken together can form a group =O; wherein R' groups are as defined above and may be selected independently from each other;

$R^1$ and $R^2$ independently represent hydrogen, —$(CH_2)_mR'$, —$CO_2R'$, —$CON(R')_2$, —CR'O, —$SO_2N(R')_2$, —NR'—CO-haloalkyl, $NO_2$, —$NR'$—$SO_2$-haloalkyl, $NR'$—$SO_2$-alkyl, —$NR'$—$SO_2$-aryl, —$NR'$—$SO_2$-heteroaryl, —$SO_2$-alkyl, —$SO_2$-aryl, —$SO_2$-heteroaryl, —NR'—CO-alkyl, —NR'—CO-aryl, —NR'—CO-heteroaryl, —NR'—CO—$N(R')_2$, —CN, alkyl, amino, amide, cycloalkyl, aminoalkyl, alkylamino, alkoxy, hydroxyl, —SH, alkylthio, hydroxyalkylamino, halogen, haloalkyl, haloalkoxy, aryl, arylalkyl or heteroaryl wherein R' groups are as defined above and may be selected independently from each other;

m is 1, 2, 3, 4, 5, 6, 7, 8, 9, 10, 11, or 12;

wherein if

X is $CR^5$, then $R^3$ forms together with $R^4$ an unsaturated or saturated cyclic group selected from the group consisting of cycloalkyl, aryl, heterocyclyl and heteroaryl which optionally has 0, 1, 2 or 3 substituents R", and wherein if X is part of a double bond, $R^5$ is absent;

$R^5$ is H, OH, halogen, $C_1$-$C_4$-alkyl;

or wherein if

X is N, then $R^3$ is hydrogen, alkyl, alkoxy, hydroxyl, hydroxyalkyl, alkoxyalkyl, or —$CO_2R'$;

$R^4$ is hydrogen, hydroxyalkyl, haloalkyl, aminoalkyl, alkoxy, cyanoalkyl, amino, alkyl, arylalkyl or a partially or entirely unsaturated or saturated cyclic group selected from the group consisting of cycloalkyl, aryl, arylalkyl, heterocyclyl, haloalkylalkyl and heteroaryl which is optionally substituted with R" as defined herein;

or wherein if

X is N, then or $R^3$ forms together with $R^4$ a 3-, 4-, 5-, 6- or 7-membered saturated or partially unsaturated or entirely unsaturated heterocyclic ring consisting of cycloalkyl, aryl, heterocyclyl, heterocycloaryl and heteroaryl which optionally has 0, 1, 2 or 3 substituents R"

In another preferred embodiment, the present invention relates to a compound of formula (I) or a physiologically acceptable salt or derivative thereof, where Ra is hydrogen, alkyl, alkoxy, hydroxyl, hydroxyalkyl, alkoxyalkyl, or —$CO_2R'$;

$R^1$ and $R^2$ are hydrogen;

$R^b$ and $R^c$ independently are alkyl, alkoxy, hydroxyl, hydroxyalkyl, alkoxyalkyl, cycloalkyl, aryl and heteroaryl, heterocycloalkyl or —$CO_2R'$;

or $R^b$ forms together with $R^c$ a 3-, 4-, 5-, 6- or 7-membered saturated or partially or entirely unsaturated heterocyclic ring which optionally has 0, 1, 2 or 3 substituents R";

R' is independently hydrogen, hydroxyalkyl, haloalkyl, aminoalkyl, alkoxy, cyanoalkyl, amino, alkyl or an unsaturated or saturated cyclic group selected from the group consisting of cycloalkyl, aryl and heteroaryl;

R" independently represents hydrogen, —$(CH_2)_mR'$, —$CO_2R'$, —$CON(R')_2$, —CR'O, —$SO_2N(R')_2$, —NR'—CO-haloalkyl, —$NO_2$, —$NR'$—$SO_2$-haloalkyl, —$NR'$—$SO_2$-alkyl, —$NR'$—$SO_2$-aryl, —$NR'$—$SO_2$-heteroaryl, —$SO_2$-alkyl, —$SO_2$-aryl, —$SO_2$-heteroaryl, —NR'—CO-alkyl, —NR'—CO-aryl, —NR'—CO-heteroaryl, —NR'—CO—$N(R')_2$, —CN, alkyl, amino, amide, cycloalkyl, aminoalkyl, alkylamino, alkoxy, hydroxyl, —SH, alkylthio, hydroxyalkyl, hydroxyalkylamino, halogen, haloalkyl, haloalkoxy, aryl, arylalkyl or heteroaryl; where chemically appropriate, two R" taken together can form a group =O; wherein R' groups are as defined above and may be selected independently from each other;

m is 1, 2, 3, 4, 5, 6, 7, 8, 9, 10, 11, or 12;

wherein if

X is $CR^5$, then $R^3$ forms together with $R^4$ an unsaturated or saturated cyclic group selected from the group consisting of cycloalkyl, aryl, heterocycloalkyl and heteroaryl which optionally has 0, 1, 2 or 3 substituents R", and wherein if X is part of a double bond, $R^5$ is absent;

or wherein if

X is N, then $R^3$ is independently hydrogen, alkyl, alkoxy, hydroxyl, hydroxyalkyl, alkoxyalkyl, or —$CO_2R'$;

$R^4$ is independently hydroxyalkyl, haloalkyl, aminoalkyl, alkoxy, cyanoalkyl, amino, alkyl, arylalkyl or a partially or entirely unsaturated or saturated cyclic group selected from the group consisting of cycloalkyl, aryl, heterocycloalkyl and heteroaryl which is optionally substituted with R" as defined herein;

$R^5$ is H, OH, halogen, $C_{1-4}$ alkyl;

or $R^3$ forms together with $R^4$ a 3-, 4-, 5-, 6- or 7-membered saturated or partially or entirely unsaturated heterocyclic ring which optionally has 0, 1, 2 or 3 substituents R" as defined herein;

Preferably, $R^3$=H, $R^4$=alkylaryl, $R^a$=H, and $R^b$ forms together with $R^c$ a 6-membered saturated heterocyclic ring which optionally has 0, 1, 2 or 3 substituents R".

More preferably $R^3$=H, $R^4$=benzyl, substituted with aminosulfonyl, $R^a$=H, and $R^b$ forms together with $R^c$ a piperazinyl, substituted with n-butyl.

In another preferred embodiment, the present invention relates to a compound of formula (I) and the pharmaceutically acceptable salt or solvate thereof, wherein $R^a$ is hydrogen, alkyl, alkoxy, hydroxyl, hydroxyalkyl, alkoxyalkyl, —OCOR', —C(O)R', —CONHR' or —$CO_2R'$;

$R^b$ and $R^c$ independently are alkyl, alkoxy, hydroxyl, hydroxyalkyl, alkoxyalkyl, aminoalkyl, alkylaminoalkyl, haloalkyl, cycloalkyl, aryl and heteroaryl, heterocyclyl or —$CO_2R'$;

R' independently represents hydrogen, —$CO_2R"$, —CONHR", —CR"O, —$SO_2N(R')_2$, —$SO_2NHR"$, —NR"—CO-haloalkyl, —$NO_2$, —$NR"$-$SO_2$-haloalkyl, —$NR"$-$SO_2$-alkyl, —$SO_2$-alkyl, —NR"—CO-alkyl, —CN, alkyl, cycloalkyl, amino, aminoalkyl, alkylamino, alkoxy, —OH, —SH, alkylthio, hydroxyalkyl, hydroxyalkylamino, halogen, haloalkyl, haloalkoxy, aryl, haloaryl, haloarylalkyl, arylalkyl, heterocyclyl or heteroaryl;

R" is independently hydrogen, —$(CH_2)_mR'$, —$CO_2R'$, —$CON(R')_2$, —CR'O, —$SO_2N(R')_2$, —NR'—CO-haloalkyl, —$NO_2$, —$NR'$—$SO_2$-haloalkyl, —$NR'$—$SO_2$-alkyl, —$NR'$-$SO_2$-aryl, —$NR'$-$SO_2$-heteroaryl, —$SO_2$- alkyl, —SO$_2$-aryl, —SO$_2$-heteroaryl, —NR'—CO-alkyl, —NR'—CO-aryl, —NR'—CO-heteroaryl, —NR'—CO—N(R')$_2$, —CN, alkyl, amino, amide, cycloalkyl, aminoalkyl, alkylamino, alkoxy, alkoxyalky, hydroxyl, —SH, alkylthio, hydroxyalkyl, hydroxyalkylamino, halogen, haloalkyl, haloalkoxy, aryl, arylalkyl or heteroaryl; where chemically appropriate, two R" taken together can form a group =O; wherein R' groups are as defined above and may be selected independently from each other;

$R^1$ and $R^2$ independently represents hydrogen, —(CH$_2$)$_m$R', —CO$_2$R', —CON(R')$_2$, —CR'O, —SO$_2$N(R')$_2$, —NR'—CO-haloalkyl, NO$_2$, —NR'—SO$_2$-haloalkyl, NR'—SO$_2$-alkyl, —NR'—SO$_2$-aryl, —NR'—SO$_2$-heteroaryl, —SO$_2$-alkyl, —SO$_2$-aryl, —SO$_2$-heteroaryl, —NR'—CO-alkyl, —NR'—CO-aryl, —NR'—CO-heteroaryl, —NR'—CO—N(R')$_2$, —CN, alkyl, amino, amide, cycloalkyl, aminoalkyl, alkylamino, alkoxy, hydroxyl, —SH, alkylthio, hydroxyalkyl, hydroxyalkylamino, halogen, haloalkyl, haloalkoxy, aryl, arylalkyl or heteroaryl wherein R' groups are as defined above and may be selected independently from each other;

m is 1, 2, 3, 4, 5, 6, 7, 8, 9, 10, 11, or 12;

wherein if

X is CR$^5$, then $R^3$ forms together with $R^4$ an unsaturated or saturated cyclic group selected from the group consisting of cycloalkyl, aryl, heterocyclyl and heteroaryl which optionally has 0, 1, 2 or 3 substituents R", and wherein if X is part of a double bond, R$^5$ is absent;

$R^5$ is H, OH, halogen, C$_1$-C$_4$-alkyl;

or wherein if

X is N, then $R^3$ is hydrogen, alkyl, alkoxy, hydroxyl, hydroxyalkyl, alkoxyalkyl, or —CO$_2$R';

$R^4$ is hydrogen, hydroxyalkyl, haloalkyl, aminoalkyl, alkoxy, cyanoalkyl, amino, alkyl, arylalkyl or a partially or entirely unsaturated or saturated cyclic group selected from the group consisting of cycloalkyl, aryl, arylalkyl, heterocyclyl, haloarylalkyl and heteroaryl which is optionally substituted with R" as defined herein;

or wherein if

X is N, then or $R^3$ forms together with $R^4$ a 3-, 4-, 5-, 6- or 7-membered saturated or partially unsaturated or entirely unsaturated heterocyclic ring consisting of cycloalkyl, aryl, heterocyclyl, heterocycloaryl and heteroaryl which optionally has 0, 1, 2 or 3 substituents R"

In another preferred embodiment, the present invention relates to a compound of formula (I) and the pharmaceutically acceptable salt or solvate thereof, wherein $R^a$ is hydrogen, alkyl, alkoxy, hydroxyl, hydroxyalkyl, alkoxyalkyl, —OCOR', —C(O)R', —CONHR' or —CO$_2$R';

$R^b$ forms together with $R^c$ a 3-, 4-, 5-, 6- or 7-membered saturated, partially unsaturated or entirely unsaturated heterocyclic ring selected from the group consisting of cycloalkyl, aryl, heterocycloalkyl and heteroaryl which optionally has 0, 1, 2 or 3 substituents R", where chemically appropriate, two R" taken together can form a group =O; this heterocyclic group is preferably selected from the group consisting of piperidinyl, piperazinyl, morpholinyl, pyrrolidinyl, thiazolidinyl, thiomorpholinyl, piperidin-4-one-1-yl, S,S-dioxo-thio-morpholinyl, piperazin-3-one-1-yl, or azepanyl R' independently represents hydrogen, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, amino, aminoalkyl, alkylamino, alkoxy, —OH, —SH, alkylthio, hydroxyalkyl, hydroxyalkylamino, halogen, haloalkyl, haloalkoxy, aryl, haloaryl, haloarylalkyl, arylalkyl, heterocyclyl or heteroaryl;

R" independently hydrogen, —(CH$_2$)$_m$R', —CO$_2$R', —CON(R')$_2$, —CR'O, —SO$_2$N(R')$_2$, —NR'—CO-haloalkyl, —NO$_2$, —NR'—SO$_2$-haloalkyl, —NR'—SO$_2$-alkyl, —NR'—SO$_2$-aryl, —NR'—SO$_2$-heteroaryl, —SO$_2$-alkyl, —SO$_2$-aryl, —SO$_2$-heteroaryl, —NR'—CO-alkyl, —NR'—CO-aryl, —NR'—CO-heteroaryl, —NR'—CO—N(R')$_2$, —CN, alkyl, amino, amide, cycloalkyl, aminoalkyl, alkylamino, alkoxy, alkoxyalky, hydroxyl, —SH, alkylthio, hydroxyalkyl, hydroxyalkylamino, halogen, haloalkyl, haloalkoxy, aryl, arylalkyl or heteroaryl; where chemically appropriate, two R" taken together can form a group =O; wherein R' groups are as defined above and may be selected independently from each other;

$R^1$ and $R^2$ independently represents hydrogen, —(CH$_2$)$_m$R', —CO$_2$R', —CON(R')$_2$, —CR'O, —SO$_2$N(R')$_2$, —NR'—CO-haloalkyl, NO$_2$, —NR'—SO$_2$-haloalkyl, NR'—SO$_2$-alkyl, —NR'—SO$_2$-aryl, —NR'—SO$_2$-heteroaryl, —SO$_2$-alkyl, —SO$_2$-aryl, —SO$_2$-heteroaryl, —NR'—CO-alkyl, —NR'—CO-aryl, —NR'—CO-heteroaryl, —NR'—CO—N(R')$_2$, —CN, alkyl, amino, amide, cycloalkyl, aminoalkyl, alkylamino, alkoxy, hydroxyl, —SH, alkylthio, hydroxyalkyl, hydroxyalkylamino, halogen, haloalkyl, haloalkoxy, aryl, arylalkyl or heteroaryl wherein R' groups are as defined above and may be selected independently from each other;

m is 1, 2, 3, 4, 5, 6, 7, 8, 9, 10, 11, or 12;

wherein if

X is CR$^5$, then $R^3$ forms together with $R^4$ an unsaturated or saturated cyclic group selected from the group consisting of cycloalkyl, aryl, heterocyclyl and heteroaryl which optionally has 0, 1, 2 or 3 substituents R", and wherein if X is part of a double bond, R$^5$ is absent;

$R^5$ is H, OH, halogen, C$_1$-C$_4$-alkyl;

or wherein if

X is N, then $R^3$ is hydrogen, alkyl, alkoxy, hydroxyl, hydroxyalkyl, alkoxyalkyl, or —CO$_2$R';

$R^4$ is hydrogen, hydroxyalkyl, haloalkyl, aminoalkyl, alkoxy, cyanoalkyl, amino, alkyl, arylalkyl or a partially or entirely unsaturated or saturated cyclic group selected from the group consisting of cycloalkyl, aryl, arylalkyl, heterocyclyl, haloarylalkyl and heteroaryl which is optionally substituted with R" as defined herein;

or wherein if

X is N, then $R^3$ forms together with $R^4$ a 3-, 4-, 5-, 6- or 7-membered saturated or partially unsaturated or entirely unsaturated heterocyclic ring consisting of cycloalkyl, aryl, heterocyclyl, heterocycloaryl and heteroaryl which optionally has 0, 1, 2 or 3 substituents R"

In another preferred embodiment, the present invention relates to a compound of formula (I) and the pharmaceutically acceptable salt or solvate thereof, wherein $R^a$ is hydrogen or alkyl;

$R^b$ and $R^c$ independently are alkyl, hydroxyalkyl, alkoxyalkyl, aminoalkyl, alkylaminoalkyl, or —CO2R';

R' independently represents hydrogen, —CO$_2$R", —SO$_2$N(R")$_2$, —SO$_2$NHR", —CN, alkyl, cycloalkyl, aryl, heterocyclyl or heteroaryl;

R" independently represent hydrogen, —SO$_2$N(R')$_2$, —NO$_2$, alkyl, amino, alkylamino, alkoxyalky, hydroxyl, hydroxyalkyl, halogen, wherein R' groups are as defined above and may be selected independently from each other;

R$^1$ and R$^2$ independently represent hydrogen, alkyl, amino, hydroxyl, halogen, or haloalkyl, wherein R' groups are as defined above and may be selected independently from each other;

wherein if

X is CR$^5$, then

R$^3$ forms together with R$^4$ an unsaturated or saturated cyclic group selected from the group consisting of cycloalkyl, aryl, heterocyclyl and heteroaryl which optionally has 0, 1, 2 or 3 substituents R", and wherein if X is part of a double bond, R$^5$ is absent;

R$^5$ is H, OH, halogen, C$_1$-C$_4$-alkyl;

or wherein if

X is N, then

R$^3$ is hydrogen or alkyl;

R$^4$ is hydrogen, amino, alkyl, aryl, arylalkyl, heterocyclyl, haloarylalkyl and heteroaryl or wherein if X is N, then R$^3$ forms together with R$^4$ a 3-, 4-, 5-, 6- or 7-membered saturated or partially unsaturated or entirely unsaturated heterocyclic ring consisting of cycloalkyl, aryl, heterocyclyl, heterocycloaryl and heteroaryl which optionally has 0, 1, 2 or 3 substituents R".

In another preferred embodiment, the present invention relates to a compound of formula (I) and the pharmaceutically acceptable salt or solvate thereof, wherein R$^a$ is hydrogen or alkyl;

R$^b$ forms together with R$^c$ a 3-, 4-, 5-, 6- or 7-membered saturated, partially unsaturated or entirely unsaturated heterocyclic ring selected from the group consisting of cycloalkyl, aryl, heterocycloalkyl and heteroaryl which optionally has 0, 1, 2 or 3 substituents R", where chemically appropriate, two R" taken together can form a group =O; this heterocyclic group is preferably selected from the group consisting of piperidinyl, piperazinyl, morpholinyl, pyrrolidinyl, thiazolidinyl, thiomorpholinyl, piperidin-4-one-1-yl, S,S-dioxo-thio-morpholinyl, piperazin-3-one-1-yl, or azepanyl R' independently represents hydrogen, —CO$_2$R", —SO$_2$N(R")$_2$, —SO$_2$NHR", —CN, alkyl, cycloalkyl, aryl, heterocyclyl or heteroaryl;

R" independently represent hydrogen, —SO$_2$N(R')$_2$, —NO$_2$, alkyl, amino, alkylamino, alkoxyalky, hydroxyl, hydroxyalkyl, halogen, wherein R' groups are as defined above and may be selected independently from each other;

R$^1$ and R$^2$ independently represent hydrogen, alkyl, amino, hydroxyl, halogen, or haloalkyl, wherein R' groups are as defined above and may be selected independently from each other;

wherein if

X is CR$^5$, then

R$^3$ forms together with R$^4$ an unsaturated or saturated cyclic group selected from the group consisting of cycloalkyl, aryl, heterocyclyl and heteroaryl which optionally has 0, 1, 2 or 3 substituents R", and wherein if X is part of a double bond, R$^5$ is absent;

R$^5$ is H, OH, halogen, C$_1$-C$_4$-alkyl;

or wherein if

X is N, then

R$^3$ is hydrogen or alkyl;

R$^4$ is hydrogen, amino, alkyl, aryl, arylalkyl, heterocyclyl, haloarylalkyl and heteroaryl or wherein if X is N, then R$^3$ forms together with R$^4$ a 3-, 4-, 5-, 6- or 7-membered saturated or partially unsaturated or entirely unsaturated heterocyclic ring consisting of cycloalkyl, aryl, heterocyclyl, heterocycloaryl and heteroaryl which optionally has 0, 1, 2 or 3 substituents R".

Preferably, R$^3$=H, R$^4$=alkylaryl, R$^a$=H, and R$^b$ forms together with R$^c$ a 6-membered saturated heterocyclic ring which optionally has 0, 1, 2 or 3 substituents R".

Preferably, R$^3$=H, R$^4$=alkylaryl, R$^a$=H, and R$^b$ forms together with R$^c$ a piperidinyl, piperazinyl, morpholinyl, pyrrolidinyl, thiazolidinyl, thiomorpholinyl, piperidin-4-one-1-yl, S,S-dioxo-thio-morpholinyl, piperazin-3-one-1-yl, or azepanyl, which optionally has 0, 1, 2 or 3 substituents R".

More preferably R$^3$=H, R$^4$=benzyl, substituted with aminosulfonyl, R$^a$=H, and R$^b$ forms together with R$^c$ a piperazinyl, which optionally has 0, 1, 2 or 3 substituents R".

In another preferred embodiment, the present invention relates to a compound of formula (I) and the pharmaceutically acceptable salt or solvate thereof, wherein R$^3$=H, R$^4$=aryl, R$^a$=H, and R$^b$ forms together with R$^c$ a 6-membered saturated heterocyclic ring which optionally has 0, 1, 2 or 3 substituents R".

Preferably, R$^3$=H, R$^4$=aryl, R$^a$=H, and R$^b$ forms together with R$^c$ a piperidinyl, piperazinyl, morpholinyl, pyrrolidinyl, thiazolidinyl, thiomorpholinyl, piperidin-4-one-1-yl, S,S-dioxo-thio-morpholinyl, piperazin-3-one-1-yl, or azepanyl, which optionally has 0, 1, 2 or 3 substituents R".

More preferably R$^3$=H, R$^4$=phenyl, substituted with aminosulfonyl, R$^a$=H, and R$^b$ forms together with R$^c$ a piperazinyl, which optionally has 0, 1, 2 or 3 substituents R".

Another embodiment of the invention is a pharmaceutical composition, comprising a compound according to formula (I) and a pharmaceutically acceptable carrier or diluent.

Another embodiment of the invention is a method of treating or preventing or ameliorating a disease or condition in a subject comprising the administration of a compound according to formula (I).

In a preferred embodiment the disease or condition is malaria.

In a more preferred embodiment the disease or condition is malaria, caused by a strain of *Plasmodium falciparum*.

An aryl group denotes an aromatic group having five to fifteen carbon atoms, which may be substituted by one or more substituents R', and may be fused to another aromatic ring; the aryl group is preferably a phenyl group, -o-C$_6$H$_4$—R', -m-C$_6$H$_4$—R', -p-C$_6$H$_4$—R', 1-naphthyl, 2-naphthyl, 1-anthracenyl or 2-anthracenyl;

a heteroaryl group denotes a 5- or 6-membered heterocyclic group which contains at least one heteroatom like O, S or N, wherein the heteroatom N is optionally substituted with R', and/or the heteroatom S is optionally bonded to =O or (=O)$_2$. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, benzooxazol-2-yl, benzooxazol-4-yl, benzooxazol-5-yl, benzoisooxazol-3-yl, benzoisooxazol-4-yl, benzoisooxazol-5-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, benzoisothiazol-3-yl, benzoisothiazol-4- yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3vyl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4visoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benzimidazol-5-yl, benzimidazol-6-yl, benzimidazol-7-yl, tetrahydro-thieno[3,4-d]imidazol-2-one, pyrazolo[5,1-c][1,2,4]triazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or 4-[1,2,4]triazolo[4,3-a]pyridin-3-yl, 1-furo[2,3-c]pyridin-4-yl, 1-furo[2,3-c]pyridin-5-yl, 1-furo[2,3-c]pyridin-3-yl, and triazolopyridazine group. This heterocyclic group can be substituted by one or more substituents R', wherein R' is as defined above;

a heterocyclyl or heterocycloalkyl group denotes a 3- to 8-membered heterocyclic non-aromatic group which contains at least one heteroatom selected from O, N, and S, wherein the heterocyclyl group may be fused to another non-aromatic ring and may be substituted by one or more substituents R', wherein R' is as defined above; the $C_3$-$C_8$-heterocyclyl residue may be selected from the group consisting of cyclo-$C_3H_5$, cyclo-$C_4H_7$, cyclo-$C_5H_9$, -cyclo-$C_6H_{11}$, -cyclo-$C_7H_{13}$, -cyclo-$C_8H_{15}$, morpholine-4-yl, piperazinyl, morpholine-4-yl, 1-alkylpiperazine-4-yl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, thiazolidinyl, piperidin-4-one-1-yl, S,S-dioxo-thio-morpholinyl, piperazin-3-one-1-yl, azepanyl and pyranyl;

a heterocycloaryl group denotes a 5- or 6-membered heterocyclic non-aromatic group which contains at least one heteroatom selected from O, N, and S, wherein the heterocyclyl group may be fused to an aromatic ring and may be substituted by one or more substituents R', wherein R' is as defined above;

To keep the definitions as short as possible, in the following paragraphs "alkyl" is to be understood to encompass alkyl, alkenyl and alkynyl.

In the context of the present invention, an alkyl group, if not stated otherwise, denotes a linear or branched $C_1$-$C_8$-alkyl, preferably a linear or branched chain of one to five carbon atoms; an alkenyl group, if not stated otherwise, denotes a linear or branched $C_2$-$C_8$-alkenyl; and an alkynyl group, if not stated otherwise, denotes a linear or branched $C_2$-$C_8$-alkynyl group, which may be substituted by one or more substituents R'.

The $C_1$-$C_8$-alkyl, $C_2$-$C_8$-alkenyl and $C_2$-$C_8$-alkynyl residue may be selected from the group consisting of —CH$_3$, —C$_2$H$_5$, —CH═CH$_2$, —C≡CH, —C$_3$H$_7$, —CH(CH$_3$)$_2$, —CH$_2$—CH═CH$_2$, —C(CH$_3$)═CH$_2$, —CH═CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R')$_3$, —C$_2$(R')$_5$, —CH$_2$—C(R')$_3$, —C$_3$ (R')$_7$, —C$_2$H$_4$—C(R')$_3$, —C$_2$H$_4$—CH═CH$_2$, —CH═CH—C$_2$H$_5$, —CH═C(CH$_3$)$_2$, —CH$_2$—CH═CH—CH$_3$, —CH═CH—CH═CH$_2$, —C$_2$H$_4$—C≡CH, —C≡C—C$_2$H$_5$, —CH$_2$—C≡C—CH$_3$, —C≡C—CH═CH$_2$, —CH═CH—C≡CH, —C≡C—C≡CH, —C$_2$H$_4$—CH(CH$_3$)$_2$, —CH(CH$_3$) —C$_3$H$_7$, —CH$_2$—CH(CH$_3$) —C$_2$H$_5$, —CH(CH$_3$) —CH(CH$_3$)$_2$, —C(CH$_3$)$_2$—C$_2$H$_5$, —CH$_2$—C(CH$_3$)$_3$, —C$_3$H$_6$—CH═CH$_2$, —CH═CH—C$_3$H$_7$, —C$_2$H$_4$—CH═CH—CH$_3$, —CH$_2$—CH═CH—C$_2$H$_5$, —CH$_2$—CH═CH—CH═CH$_2$, —CH═CH—CH═CH—CH$_3$, —CH═CH—CH$_2$—CH═CH$_2$, —C(CH$_3$)═CH—CH═CH$_2$, —CH═C(CH$_3$)—CH═CH$_2$, —CH═CH—C(CH$_3$)═CH$_2$, —CH$_2$—CH═C(CH$_3$)$_2$, —C(CH$_3$)═C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH═CH$_2$, —CH$_2$—CH═CH—C≡CH, —CH$_2$—C≡C—C≡CH, —C≡C—CH═CH—CH$_3$, —CH═CH—C≡C—CH$_3$, —C≡C—C≡C—CH$_3$, —C≡C—CH$_2$—CH═CH$_2$, —CH═CH—CH$_2$—C≡CH, —C≡C—CH$_2$—C≡CH, —C(CH$_3$)═CH—CH═CH$_2$, —CH═C(CH$_3$)—CH═CH$_2$, —CH═CH—C(CH$_3$)═CH$_2$, —C(CH$_3$)═CH—C≡CH, —CH═C(CH$_3$)—C≡CH, —C≡C—C(CH$_3$)═CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH═CH$_2$, —CH═CH—C$_4$H$_9$, —C$_3$H$_6$—CH═CH—CH$_3$, —CH$_2$—CH═CH—C$_3$H$_7$, —C$_2$H$_4$—CH═CH—C$_2$H$_5$, —CH$_2$—C(CH$_3$)═C(CH$_3$)$_2$, —C$_2$H$_4$—CH═C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, and —C$_2$H$_4$—C≡C—C$_2$H$_5$;

an arylalkyl group denotes a linear or branched $C_1$-$C_8$-alkyl substituted with at least one aryl group as defined herein. Exemplary arylalkyl groups include benzyl, phenylethyl, 1-(1-phenylethyl), 4-hydroxybenzyl, 3-fluorobenzyl, 2-fluorophenylethyl, and the like. This arylalkyl group can be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring may be substituted by a group E, E being O, S, SO, SO$_2$, N, or NR", R" being as defined above; the $C_3$-$C_8$-cycloalkyl residue may be selected from the group consisting of -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, and 1-alkylpiperazine-4-yl. This cycloalkyl group can be substituted by one or more substituents R', wherein R' is as defined above;

an alkoxy group denotes an O-alkyl group, the alkyl group being as defined above; the alkoxy group is preferably a methoxy, ethoxy, isopropoxy, t-butoxy or pentoxy group;

an alkylthio group denotes a S-alkyl group, the alkyl group being as defined above;

a haloalkyl group denotes a alkyl group as defined above substituted by one or more halogen atoms, preferably substituted by one to five halogen atoms, the haloalkyl group is preferably a —C(R$^{10}$)$_3$, —CR$^{10}$(R$^{10}$)$_2$, —CR$^{10}$(R$^{10'}$)R$^{10''}$, —$C_2(R^{10})_5$, —$CH_2$—$C(R^{10})_3$, —$C(R^{10})_2$—$CH(R^{10'})_2$, —$CH_2$—$CR^{10}(R^{10'})_2$, —$CH_2$—$CR^{10}(R^{10'})R^{10''}$, —$C_3(R^{10})_7$, or —$C_2H_4$—$C(R)_3$, wherein $R^{10}$, $R^{10'}$, $R^{10''}$ represent F, Cl, Br or I, preferably F;

a haloaryl group denotes a aryl group as defined above substituted by one or more halogen atoms, preferably substituted by one to five halogen atoms;

a haloarylalkyl group denotes a linear or branched $C_1$-$C_8$-alkyl substituted with at least one haloaryl group as defined herein;

a cyanoalkyl group denotes a NC-alkyl group, the alkyl group being as defined above;

a hydroxyalkyl group denotes a HO-alkyl group, the alkyl group being as defined above;

a haloalkoxy group denotes an alkoxy group as defined above substituted by one or more halogen atoms, preferably substituted by one to five halogen atoms, the haloalkoxy group is preferably a) —$OC(R^{10})_3$, —$OCR^{10}(R^{10'})_2$, —$OCR^{10}(R^{10'})R^{10''}$, —$OC_2(R^{10})_5$, —$OCH_2$—$C(R^{10})_3$, —$OCH_2$—$CR^{10}(R^{10'})_2$, —$OCH_2$—$CR^{10}(R^{10'})R^{10''}$, —$OC_3(R^{10})_7$ or —$OC_2H_4$—$C(R^{10})_3$, wherein $R^{10}$, $R^{10'}$, $R^{10''}$ represent F, Cl, Br or I, preferably F;

a hydroxyalkylamino group denotes a (HO-alkyl)$_2$—N— group or HO-alkyl-NH— group, the alkyl group being as defined above;

an alkylamino group denotes a HN-alkyl or N-dialkyl group, the alkyl group being as defined above;

an aminoalkyl group denotes an -alkyl-NH$_2$ group, the alkyl group being as defined above;

an alkylaminoalkyl group denotes an alkyl-NH-alkyl or alkyl-N-dialkyl group, the alkyl group being as defined above a halo or halogen group denotes fluorine, chlorine, bromine, or iodine; preferably chlorine or fluorine.

Compounds having infinite chains consisting for instance of repeating R' and R" units and the like are not encompassed by this invention. Thus, the longest chain allowed in each side chain $R^a$, $R^b$, $R^c$, $R^1$, $R^2$, $R^3$, and $R^4$ of the compounds according to the invention are three coupled substituents R' and/or R", e.g. R' substituted with R" further substituted with R' or the like;

this is to be understood such that oligomeric or polymeric side chains comprising more repeating R' and/or R" units as above outlined are not within the scope of the present invention.

Constituents which are optionally substituted as stated herein may be substituted, unless otherwise noted, at any chemically possible position.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The person skilled in the art is aware on account of his/her expert knowledge that certain combinations of the variable characteristics mentioned in the description of this invention lead to chemically less stable compounds. This can apply, for example, to certain compounds, in which—in a manner being disadvantageous for chemical stability—two heteroatoms (S, N or O) would directly meet or would only be separated by one carbon atom. Those compounds according to this invention, in which the combination of the abovementioned variable substituents does not lead to chemically less stable compounds, are therefore preferred.

The invention also provides a pharmaceutical composition comprising a compound of formula (I), in free form or in the form of pharmaceutically acceptable salts and physiologically functional derivatives, together with a pharmaceutically acceptable diluent or carrier therefore.

In another aspect, the present invention also provides a method for the treatment or prophylaxis of diseases which occur due to the attack of humans by protozoa which comprises the administration of an effective amount of a compound of formula (I) and physiologically acceptable salts or physiologically functional derivatives thereof.

The invention is also directed to the use of compounds of the formula (I) and of their pharmacologically tolerable salts or physiologically functional derivatives for the production of a medicament for the prevention and treatment of diseases, where reduction of parasites is of benefit.

Suitable salts for compounds of formula (I) according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are, depending on substitution, also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds of formula (I) according to this invention on an industrial scale, are converted into pharmacologically tolerable salts by processes known to the person skilled in the art.

According to expert's knowledge the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention. For instance, the mono-, di-, tri-, and tetrahydrates of formula (I) are encompassed.

The compounds of the formula (I) and their pharmacologically acceptable salts can be administered to animals, preferably to mammals, and in particular to humans, as therapeutics per se, as mixtures with one another or in the form of pharmaceutical preparations which allow entreat or parenteral use and which as active constituent contain an effective dose of at least one compound of the formula (I) or a salt thereof, in addition to customary pharmaceutically innocuous excipients and additives. The compounds of formula (I) can also be administered in form of their salts, which are obtainable by reacting the respective compounds with physiologically acceptable acids and bases.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

In addition to the active compounds of formula (I), the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula (I) or their pharmacologically acceptable salts and also other therapeutically active substances.

Thus, the compounds of the present invention can be used in the form of one substance alone or in combination with other active compounds—for example with medicaments already known for the treatment of the aforementioned diseases, whereby in the latter case a favorable additive, amplifying effect is noticed.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The physiologically functional derivatives also include prodrugs of the compounds of the invention. Such prodrugs may be metabolized in vivo to a compound of the invention. These prodrugs may or may not be active themselves.

Prodrugs of the compounds of the present invention include but are not limited to: esters, which are transformed in vivo into the corresponding active alcohol, esters, which are transformed in vivo into the corresponding active acid, imines, which are transformed in vivo into the corresponding amines, imines which are metabolized in vivo into the corresponding active carbonyl derivative (e.g. aldehyde or ketone), 1-carboxy-amines, which are decarboxylated in vivo into the active amine, phosphoryloxy-compounds, which are dephosphorylated in vivo by phosphatases into the active alcohols, amidoxime which are transformed into the corresponding amidine, and amides which are metabolized into the corresponding active amine or acid respectively.

For a definition of prodrugs see for example Han Han H. K., Amidon G. L.; Targeted Prodrug Design to Optimize Drug Delivery. *AAPS PharmSci.*, 2(1): article 6. (2000), DOI: 10.1208/ps020106 and Clement B.; Reduction of N-Hydroxylated Compounds: Amidoximes (N-Hydroxyamidines) as prodrugs of amidines. *Drug Metabolism Reviews,* 34 (2002), 565-579. The physiologically functional derivatives furthermore include, for example, glucuronides, sulfuric acid esters, glycosides and ribosides.

The compounds of formula (I) can also be used in the form of a precursor (prodrug) or a suitably modified form that releases the active compound in vivo.

The compounds according to the invention and medicaments prepared therewith are generally suitable for the treatment of diseases which occur due to attack of humans or animals by protozoa. Veterinary- and human-pathogenic protozoa of this type are preferably intracellularly active parasites of the classes Apicomplexa and Zoomastigophora, in particular trypanosomes, plasmodia (malarial parasites), leishmaniasis, babesiasis and theileriasis, cryptosporidiidae, sarcocystidae, amoebae, coccidia and trichomonads. The compounds or corresponding medicaments are particularly preferably suitable for the treatment of diseases caused by plasmodia, in particular for the treatment of tropical malaria, which is caused by *Plasmodium falciparum*, for the treatment of benign tertian malaria, caused by *Plasmodium vivax* and *Plasmodium ovale* and for the treatment of quartan malaria, caused by *Plasmodium malariae*; Most preferred is the use of the compounds according to the invention for the treatment of coccidiosis or malarial diseases or for the production of a medicament or, if appropriate, of a feed for the treatment of coccidioses or malarial diseases. The treatment can in this case be carried out prophylactically or curatively.

The invention thus makes available novel medicaments for the treatment of the various forms of malaria, in particular for the treatment of tropical malaria. It was surprising that the compounds proved active not only against chloroquine-sensitive, but also against chloroquine-resistant, *Plasmodium falciparum* strains.

The compounds of the present invention are also useful for the treatment of diseases which are caused by eukaryotic protists of the genus *Plasmodium.*

The invention relates to the use of a composition according to the invention for the manufacture of a medicament.

The compounds of the present invention can be used alone or in combination with other antimalarial compounds such as chloroquine, sulfadoxine/pyrimethamine, dapsone/pyrimethamine, sulfonamides, halofantrine, amodiaquine, mefloquine, quinine, quinidine, doxycycline, lumefantrine, primaquine, proguanil, atovaquone, pyronaridine, chlorproguanyl, artemesinin, arteflene, artemether, artesunate or trimethoprim.

Exemplary compounds according to this invention may include any one selected from 1. 4-(3-(3-((4-butylpiperazin-1-yl)(imino)methyl)phenyl) ureido)benzenesulfonamide
2. 4-(3-(3-((4-hydroxypiperidin-1-yl)(imino)methyl)phenyl) ureido)benzenesulfonamide
3. 4-(3-(3-(imino(piperazin-1-yl)methyl)phenyl)ureido)benzenesulfonamide
4. 1-(4-(4-bromophenylsulfonyl)phenyl)-3-(3-((4-butylpiperazin-1-yl)(imino)methyl)phenyl)urea
5. 1-(4-(4-bromophenylsulfonyl)phenyl)-3-(3-((4-hydroxypiperidin-1-yl)(imino)methyl)phenyl)urea
6. 1-(3-(imino(morpholino)methyl)phenyl)-3-(4-(4-nitrophenylsulfonyl)phenyl)urea
7. 1-(3-(imino(pyrrolidin-1-yl)methyl)phenyl)-3-(4-(4-nitrophenylsulfonyl)phenyl)urea
8. 1-(3-(imino(4-methylpiperazin-1-yl)methyl)phenyl)-3-(4-(4-nitrophenylsulfonyl)phenyl)urea
9. 1-(3-(imino(thiazolidin-3-yl)methyl)phenyl)-3-(4-(4-nitrophenylsulfonyl)phenyl)urea
10. 1-(3-((4-hydroxypiperidin-1-yl)(imino)methyl)phenyl)-3-(4-(4-nitrophenylsulfonyl)phenyl)urea
11. 1-(4-(4-chlorophenylsulfonyl)phenyl)-3-(3-((4-hydroxypiperidin-1-yl)(imino)methyl)phenyl)urea 12. 1-(4-(4-bromophenylsulfonyl)phenyl)-3-(3-((4-(hydroxymethyl)piperidin-1-yl)(imino)methyl)phenyl)urea
13. 3-(3-(4-(4-bromophenylsulfonyl)phenyl)ureido)-N,N-bis(2-methoxyethyl)benzimidamide
14. 1-(4-(4-bromophenylsulfonyl)phenyl)-3-(3-(imino(thiomorpholino)methyl)phenyl)urea
15. 1-(4-(4-bromophenylsulfonyl)phenyl)-3-(3-(imino(pyrrolidin-1-yl)methyl)phenyl)urea
16. 1-((3-(3-(4-(4-bromophenylsulfonyl)phenyl)ureido)phenyl)(imino)methyl)piperidine-4-carboxamide
17. 1-(4-(4-aminophenylsulfonyl)phenyl)-3-(3-((4-hydroxypiperidin-1-yl)(imino)methyl)phenyl)urea
18. 4-(3-(3-((4-butylpiperazin-1-yl)(imino)methyl)phenyl)ureido)-N-methylbenzenesulfonamide
19. 4-(3-(3-((4-butylpiperazin-1-yl)(imino)methyl)phenyl)ureido)-N-propylbenzenesulfonamide
20. 4-(3-(3-((4-butylpiperazin-1-yl)(imino)methyl)phenyl)ureido)-N,N-bis(2-hydroxyethyl)benzenesulfonamide
21. 1-(3-((4-butylpiperazin-1-yl)(imino)methyl)phenyl)-3-(4-(morpholinosulfonyl)phenyl)urea
22. 4-(3-(3-((4-butylpiperazin-1-yl)(imino)methyl)phenyl)ureido)-N-(7-chloroquinolin-4-yl)benzenesulfonamide
23. 4-(3-(3-((4-butylpiperazin-1-yl)(imino)methyl)phenyl)ureido)-N-(4-sulfamoylphenyl)benzenesulfonamide
24. methyl 4-(imino(3-(3-(4-(N-(4-sulfamoylphenyl)sulfamoyl)phenyl)ureido)phenyl)methyl)piperazine-1-carboxylate
25. 4-(3-(3-(imino(morpholino)methyl)phenyl)ureido)-N-(4-sulfamoylphenyl)benzenesulfonamide
26. 4-(3-(3-(imino(4-methylpiperazin-1-yl)methyl)phenyl)ureido)-N-(4-sulfamoylphenyl)benzenesulfonamide
27. 4-(3-(3-(imino(4-oxopiperidin-1-yl)methyl)phenyl)ureido)-N-(4-sulfamoylbenzyl)benzenesulfonamide
28. 4-(3-(3-((4-(2-hydroxyethyl)piperazin-1-yl)(imino)methyl)phenyl)ureido)-N-(4-sulfamoylbenzyl)benzenesulfonamide
29. 4-(3-(3-((4-(hydroxymethyl)piperidin-1-yl)(imino)methyl)phenyl)ureido)-N-(4-sulfamoylbenzyl)benzenesulfonamide
30. N-ethyl-N-(2-hydroxyethyl)-3-(3-(4-(N-(4-sulfamoylbenzyl)sulfamoyl)phenyl)ureido)benzimidamide
31. 4-(3-(3-(imino(thiomorpholino)methyl)phenyl)ureido)-N-(4-sulfamoylbenzyl)benzenesulfonamide
32. N,N-bis(2-methoxyethyl)-3-(3-(4-(N-(4-sulfamoylbenzyl)sulfamoyl)phenyl)ureido)benzimidamide
33. 1-(imino(3-(3-(4-(N-(4-sulfamoylbenzyl)sulfamoyl)phenyl)ureido)phenyl)methyl)piperidine-4-carboxamide
34. 4-(3-(3-((4-butylpiperazin-1-yl)(imino)methyl)phenyl)ureido)-N-(4-sulfamoylbenzyl)benzenesulfonamide
35. 4-(3-(3-((4-butylpiperazin-1-yl)(imino)methyl)phenyl)ureido)-N-(2,3,6-trifluorobenzyl)benzenesulfonamide
36. N-benzyl-4-(3-(3-((4-butylpiperazin-1-yl)(imino)methyl)phenyl)ureido)benzenesulfonamide
37. 4-(3-(3-((4-ethylpiperazin-1-yl)(imino)methyl)phenyl)ureido)-N-(4-sulfamoylbenzyl)benzenesulfonamide
38. 4-(3-(3-(imino(4-propylpiperazin-1-yl)methyl)phenyl)ureido)-N-(4-sulfamoylbenzyl)benzenesulfonamide
39. 4-(3-(3-((4-allylpiperazin-1-yl)(imino)methyl)phenyl)ureido)-N-(4-sulfamoylbenzyl)benzenesulfonamide
40. 4-(2-(4-(3-(3-((4-butylpiperazin-1-yl)(imino)methyl)phenyl)ureido)phenylsulfonyl)hydrazinyl)benzenesulfonamide
41. 2-(4-(3-(3-((4-butylpiperazin-1-yl)(imino)methyl)phenyl)ureido)phenylsulfonyl)isoindoline-5-sulfonamide
42. 4-(3-(3-((4-butylpiperazin-1-yl)(imino)methyl)phenyl)ureido)-N-(1-(4-sulfamoylphenyl)ethyl)benzenesulfonamide
43. 4-(3-(3-(imino (morpholino)methyl)phenyl)ureido)-N-(4-sulfamoylbenzyl)benzenesulfonamide
44. 4-(3-(3-((1,1-dioxidothiomorpholino)(imino)methyl)phenyl)ureido)-N-(4-sulfamoylbenzyl)benzenesulfonamide
45. 4-(3-(3-(imino (4-(pyridin-4-ylmethyl)piperazin-1-yl)methyl)phenyl)ureido)-N-(4-sulfamoylbenzyl)benzenesulfonamide
46. 4-(3-(3-(imino(pyrrolidin-1-yl)methyl)phenyl)ureido)-N-(4-sulfamoylbenzyl)benzenesulfonamide
47. N-(2-(diethylamino)ethyl)-N-methyl-3-(3-(4-(N-(4-sulfamoylbenzyl)sulfamoyl)phenyl)ureido)benzimidamide
48. 4-(3-(3-((4-hydroxypiperidin-1-yl)(imino)methyl)phenyl)ureido)-N-(4-sulfamoylbenzyl)benzenesulfonamide
49. 4-(3-(3-((3-(dimethylamino)pyrrolidin-1-yl)(imino)methyl)phenyl)ureido)-N-(4-sulfamoylbenzyl)benzenesulfonamide
50. 4-(3-(3-(imino(2-(pyrrolidin-1-ylmethyl)pyrrolidin-1-yl)methyl)phenyl)ureido)-N-(4-sulfamoylbenzyl)benzenesulfonamide
51. tert-butyl 4-(imino(3-(3-(4-(N-(4-sulfamoylbenzyl)sulfamoyl)phenyl)ureido)phenyl)methyl)piperazine-1-carboxylate
52. 4-(3-(3-(imino(piperazin-1-yl)methyl)phenyl)ureido)-N-(4-sulfamoylbenzyl)benzenesulfonamide
53. 4-(3-(3-(imino(4-methylpiperazin-1-yl)methyl)phenyl)ureido)-N-(4-sulfamoylbenzyl)benzenesulfonamide
54. 4-(3-(3-(imino(4-isopropylpiperazin-1-yl)methyl)phenyl)ureido)-N-(4-sulfamoylbenzyl)benzenesulfonamide
55. 4-(3-(3-(imino(4-pentylpiperazin-1-yl)methyl)phenyl)ureido)-N-(4-sulfamoylbenzyl)benzenesulfonamide
56. 4-(3-(3-((4-heptylpiperazin-1-yl)(imino)methyl)phenyl)ureido)-N-(4-sulfamoylbenzyl)benzenesulfonamide
57. 4-(3-(3-((4-acetylpiperazin-1-yl)(imino)methyl)phenyl)ureido)-N-(4-sulfamoylbenzyl)benzenesulfonamide
58. 4-(3-(3-(imino(4-propionylpiperazin-1-yl)methyl)phenyl)ureido)-N-(4-sulfamoylbenzyl)benzenesulfonamide
59. 4-(3-(3-(imino(4-pentanoylpiperazin-1-yl)methyl)phenyl)ureido)-N-(4-sulfamoylbenzyl)benzenesulfonamide
60. methyl 4-(imino(3-(3-(4-(N-(4-sulfamoylbenzyl)sulfamoyl)phenyl)ureido)phenyl)methyl)piperazine-1-carboxylate
61. ethyl 4-(imino(3-(3-(4-(N-(4-sulfamoylbenzyl)sulfamoyl)phenyl)ureido)phenyl)methyl)piperazine-1-carboxylate
62. propyl 4-(imino(3-(3-(4-(N-(4-sulfamoylbenzyl)sulfamoyl)phenyl)ureido)phenyl)methyl)piperazine-1-carboxylate
63. 4-(3-(3-((4-butyl-3-oxopiperazin-1-yl)(imino)methyl)phenyl)ureido)-N-(4-sulfamoylbenzyl)benzenesulfonamide
64. N,N-dimethyl-3-(3-(4-(N-(4-sulfamoylbenzyl)sulfamoyl)phenyl)ureido)benzimidamide
65. 4-(3-(3-((4-(2-cyanoethyl)piperazin-1-yl)(imino)methyl)phenyl)ureido)-N-(4-sulfamoylbenzyl)benzene sulfonamide
66. 4-(3-(3-((4-(cyclopropylmethyl)piperazin-1-yl)(imino)methyl)phenyl)ureido)-N-(4-sulfamoylbenzyl)benzene sulfonamide
67. 4-(3-(3-((4-((1,3-dioxolan-2-yl)methyl)piperazin-1-yl)(imino)methyl)phenyl)ureido)-N-(4-sulfamoylbenzyl)benzene sulfonamide
68. 4-(3-(3-(imino(4-((tetrahydrofuran-2-yl)methyl)piperazin-1-yl)methyl)phenyl)ureido)-N-(4-sulfamoylbenzyl)benzene sulfonamide 69. 4-(3-(3-(imino(4-(2-methoxyethyl)piperazin-1-yl)methyl)phenyl)ureido)-N-(4-sulfamoylbenzyl)benzene sulfonamide
70. 5-((4-(3-(3-((4-butylpiperazin-1-yl)(imino)methyl)phenyl)ureido)phenylsulfonamido)methyl)thiophene-2-sulfonamide
71. 4-(3-(4-((4-butylpiperazin-1-yl)(imino)methyl)phenyl)ureido)-N-(4-sulfamoylbenzyl)benzene sulfonamide
72. methyl 4-((acetylimino)(3-(3-(4-(N-(4-sulfamoylbenzyl)sulfamoyl)phenyl)ureido)phenyl)methyl)piperazine-1-carboxylate
73. methyl 4-((octanoylimino)(3-(3-(4-(N-(4-sulfamoylbenzyl) sulfamoyl)phenyl)ureido)phenyl)methyl)piperazine-1-carboxylate
74. methyl 4-((hydroxyimino)(4-(3-(4-(N-(4-sulfamoylbenzyl) sulfamoyl)phenyl)ureido)phenyl)methyl)piperazine-1-carboxylate

EXPERIMENTAL PART

Abbreviations index

The following abbreviations are presently used:
DCM=dichloromethane; DMF=N,N'-dimethylformamide; MeOH=methanol; EtOH=ethanol; DIEA=diisopropylethylamide; TFA=trifluoroacetic acid; MeCN=acetonitrile; HPLC=high-performance liquid chromatography; rt=room temperature; eq=molar equivalents; h=hours; TLC=Thin layer chromatography; DMSO-$d_6$=Deuterated methylsulfoxide; HPLC-MS=high-performance liquid chromatography/mass spectrometry.

Reagents Used

The following chemicals were obtained from Fisher Scientific, Germany: Isopropanol, DMA, DCM, DMF, DIEA, 3-nitrobenzamidine, 3-aminobenzamidine; tin(II) dichloride dihydrate, formic acid, acetonitrile, 4-trifluoro-methylaniline, 3-chloroaniline, 2-bromoaniline, 2-aminobenzonitrile, 2-bromo-4,6-difluoroaniline, 3-tri-fluoromethyl-4-chloraniline, 3-trifluoromethylaniline, 2-bromo-4-trifluoromethylaniline, 3,6-bis-trifluoro-methylaniline, 2,4-di-bromoaniline, butylamine, benzyl-amine, adamantylamine, oxalamide and sulphamide.

The following chemicals were obtained from Acros Organics, Belgium: 4-aminosulfonamide, 3-isocyanatobenzonitrile, n-butylpiperazine, N-chlorosuccinimide, 4-hydroxypiperidine, piperazine, hydroxylamine, 3-nitrobenzaldehyde, silica gel, 4-(4-bromophenylsulfonyl)aniline, 4-(4-nitrophenylsulfonyl)aniline, 4-(4-chlorophenylsulfonyl)aniline, methyl sulfoxide-$d_6$.

The following chemicals were obtained from Sigma-Aldrich Chemie GmbH, Germany: 4-(Chlorosulphonyl)phenyl isocyanate and 4-nitro-sulphonyl-4-aniline, pyrrolidine, 1-methylpiperazine, thiazolidine, piperidin-4-ylmethanol, bis(2-methoxyethyl) amine, thiomorpholine, piperidine-4-carboxamide, methyl piperazine-1-carboxylate, morpholine, 4-piperidone, 2-(piperazin-1-yl)ethanol, 2-(ethylamino) ethanol, 1-ethylpiperazine, n-propylpiperazine, 1-allylpiperazine, 1-(pyridin-4-ylmethyl)piperazine, tert-butyl piperazine-1-carboxylate, 1-isopropylpiperazine, n-pentylpiperazine, n-heptylpiperazine, 1-butylpiperazin-2-one, N,N-dimethylamine.

The following chemicals were obtained from Maybridge Chemical Comp. Ltd., United Kingdom: 1,1-Dioxo-1H-benzothiophen-6-ylamine, 4-benzene-sulphonylphenylamine and 3H-benzimidazol-5-ylamine.

Analytical Determination

Analytical HPLC-MS determinations were perfomed with Waters 2700 Autosampler, Waters 1525 Multisolvent Delivery System and Micromass ZQ single quadrupol mass spectrometer with electrospray source. Column: Chromolith Fast Gradient C18 (Merck), 50×2 mm, with stainless steel 2 μm prefilter. Eluent A, $H_2O+0.1\%$ HCOOH; eluent B, MeCN.

Preparative HPLC-MS were performed with a Waters 2700 Autosampler, Waters 600 Multisolvent Delivery System with preparative pump heads (500 μL), Waters 600S Controller and Waters ZQ single quadrupole mass spectrometer with electrospray source. Column: Waters X-Terra RP18, 5 μm, 19×150 mm. Eluent A, $H_2O+0.1\%$ HCOOH; eluent B, MeCN. Different linear gradients, individually adapted to sample.

$^1$H-NMR were performed with a Bruker AV300 (300.13 Mhz) at temperature of 305 K. Abbreviations used for the peak identification were: s=singlet; d=doublet; t=triplet; q=quartet; m=multiplet; J=$^1$H-$^1$H coupling constant.

Preparation Process

The compounds described in this document were prepared according to methods described in the following synthesis methods.

Procedure A—General Procedure for the Synthesis of Compounds 1-3

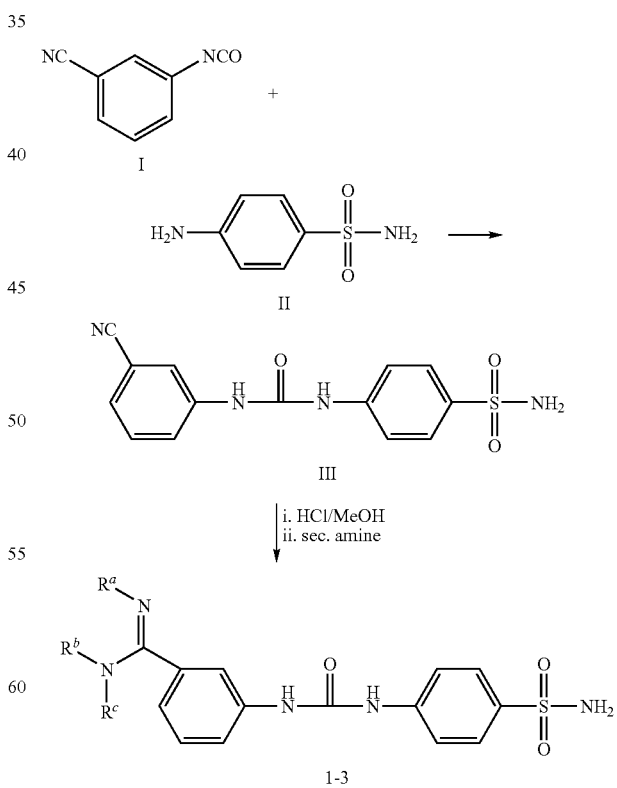

1 equivalent of 4-aminosulfonamide(II) was dissolved in DCM/DMF (3:1 solution). 1 equivalent of 3-isocyanatobenzonitrile (I) was added portionwise at rt and the reaction mixture was allowed to stir overnight. The 4-(3-(3-cyanophenyl)ureido)benzenesulfonamide (III) precipitated and was filtered. Under argon atmosphere, the dried cyano compound (III) was dissolved in a 4 M HCl solution in dioxane/MeOH 5:1 and was allowed to stir overnight at rt. The solvent was removed, the residue was washed with diethylether and the obtained methyl 3-(3-(4-sulfamoylphenyl)ureido) benzimidate was reacted further with the corresponding secondary amine in DMF at temperatures ranging between 55 to 75° C. The product (1-3) was obtained after preparative-HPLC, using a reverse-phase column and a gradient of acetonitrile in 0.1% HCOOH$_{aq}$.

Procedure B1—General Procedure for the Synthesis of Compounds 4-17 with Synthesis of the 4-(substituted)-sulfonylaniline

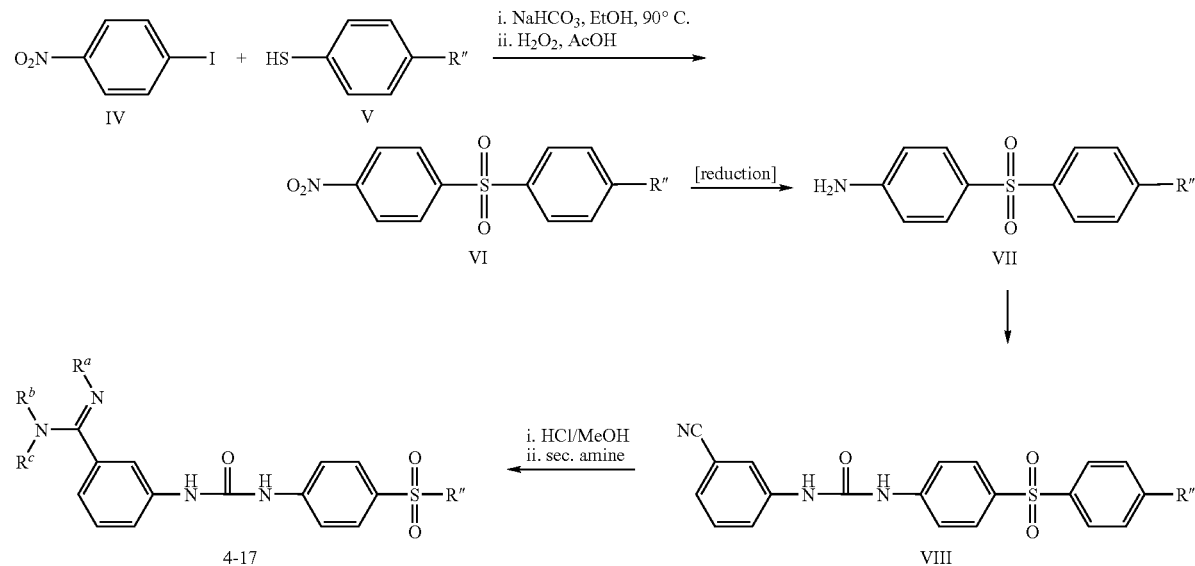

The multistep syntheses of these compounds follow the methods already described in literature (for example: E. D. Amstutz, et al., *J. Am. Chem. Soc.*, 69 (8), pp 1922-1925, 1947) and require the preparation of the 4-(substituted)-sulfonylaniline which is then reacted with 3-isocyanatobenzonitrile (I) to form the urea which is finally converted to the required products.

Step 1. Synthesis of (4-bromophenyl)(4-nitrophenyl)sulfane 1 equivalent of 1-iodo-4-nitrobenzene (IV) and 4-bromobenzenethiol (or a corresponding 4-substituted-benzenethiol) (V) were dissolved in EtOH. 8 equivalents of sodium bicarbonate were added and the mixture was stirred at reflux for 22 hours. The solvent was removed and the residue was suspended in water. The precipitate was filtered and washed with 1 M sodium hydroxide and water. The final product was obtained after re-crystallization from ethanol/water (yield: 60%).

Step 2. Synthesis of 1-bromo-4-(4-nitrophenylsulfonyl)benzene (VI)

(4-bromophenyl)(4-nitrophenyl)sulfane [or a correspondent (4-substituted)(4-nitrophenyl)sulfane)] was dissolved in concentrated acetic acid and a 30% solution of water peroxide was slowly added (18 ml for 12 g sulfane). The solution was refluxed for 2 h. A precipitate formed upon cooling of the solution to room temperature and addition of EtOH. The precipitate was filtered, washed with ice-cold EtOH and dried (yield: 91%).

Step 3. Synthesis of 4-(4-bromophenylsulfonyl)aniline (VII)

A suspension of Tin(II) chloride dihydrate in concentrated acetic acid (66.1 g in 180 ml) was treated with a 3 M solution of chloridric acid in MeOH for 30 minutes. The resulting suspension was added portionwise during 40 minutes to a suspension of the 1-bromo-4-(4-nitrophenylsulfonyl)benzene (IV) compound (28.6 g) [or a correspondent 1-substituted-4-(4-nitrophenylsulfonyl)benzene] dissolved in acetic acid and was stirred at 80° C. for 2 h. 2 litres of water were added and a precipitate formed overnight, which was filtered and washed with 10% aqueous sodium hydroxide and water. The product was crystallized from hot-cold EtOH (yield: 69%).

Step 4. Synthesis of 1-(4-(4-bromophenylsulfonyl) phenyl)-3-(3-cyanophenyl)urea (VIII)

4-(4-bromophenylsulfonyl)aniline (VII) [or a correspondent (4-substituted)sulfonylaniline] (1 equivalent) was dissolved in a 3:1 solution of DCM/DMF. A solution of 3-isocyanatobenzonitrile (I) (1 equivalent) in DCM was added dropwise. The solution was stirred overnight at rt and, after removal of the solvent, the product was crystallized from hot-cold MeOH (yield: 97%).

Step 5. Synthesis of 1-(4-(4-bromophenylsulfonyl) phenyl)-3-(3-((4-hydroxypiperidin-1-yl)(imino)methyl)phenyl)urea (4-17)

Under argon atmosphere, 1 equivalent of 1-(4-(4-bromophenylsulfonyl)phenyl)-3-(3-cyanophenyl)urea (VIII) [or a correspondent 14444-substituted-phenylsulfonyl)phenyl)-3-(3-cyanophenyl)urea] was dissolved in of 4 M HCl in dioxane/MeOH 5:1. The solution was stirred overnight at rt then the solvent was removed in vacuo. The residue was washed with diethylether, dried in vacuo, dissolved in dry MeOH (or DMF) and reacted with 1.1 to 2 equivalents of piperidin-4-ol (or 1.1 to 2 equivalents of the corresponding secondary amine) at temperature between 55 and 70° C. for a minimum of 4 h to a maximum of 22 h. The products were purified either by flash chromatography, using a silica gel column and an appropriate gradient of MeOH in DCM as eluent, or by preparative HPLC, using a reverse-phase column and a gradient of acetonitrile in 0.1% $HCOOH_{aq}$.

Procedure B2—General Procedure for the Synthesis of Compounds 4-17 when the 4-(substituted)-sulfonylaniline were Commercially Available If the 4-(substituted)-sulfonylaniline (VII) were available from commercial source, the syntheses where performed as described in Procedure B1, Step 4 and Step 5.

Procedure C—General Procedure for the Synthesis of Compounds 18-71 tion with ethylacetate/petrol ether or MeOH/diethylether. If necessary, the product was further purified by flash chromatography using a gradient of MeOH in DCM mixtures as eluent.

Step 2

Conversion of the Cyano Compound to Functionalized Benzamidine

Under argon atmosphere, 1 equivalent of the cyanoureido (XII) compound was dissolved with 20 ml of dry MeOH. 4 M HCl in dioxane was added and the solution was stirred overnight at rt. The solvent was removed; the residue was taken in diethylether which was evaporated. This operation was repeated three times to yield either a solid or an oily product.

1 equivalent of the dried benzimidate was dissolved in DMF and variable amounts of the chosen secondary amine were added (1.1 to 3 equivalents). The solution was stirred overnight at temperatures ranging from 55 to 70° C. The solvent was removed and the product was purified by preparative preparative-HPLC and a gradient of acetonitrile in 0.1% $HCOOH_{aq}$.

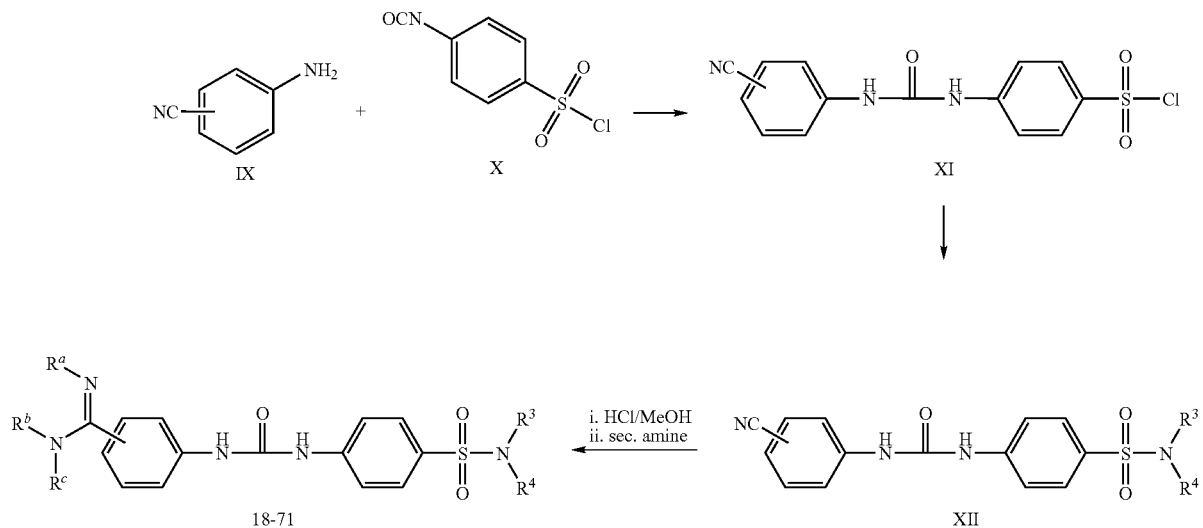

Step 1. Production of the Cyanourea Compound (XII)

28 mmol of 3-aminobenzonitrile (IX) were dissolved in 40 ml DCM. 27 mmol of 4-isocyanatobenzene-1-sulfonyl chloride (X) were added portionwise over 20 minutes and the mixture was allowed to stir at room temperature overnight. The urea product (XI) precipitated, was filtered, washed with cold DCM and was used directly in the next step (yield 93%).

An appropriate amine or aniline compound was dissolved in MeCN and DIEA was added (from 1.2 to 3 equivalents, depending on the amine or aniline compound). The solution was cooled to 0° C. and, under vigorous stifling, 1 equivalent of the ureido-sulfonylchloride compound (XI) was added portionwise. The reaction was allowed to stir overnight, allowing the temperature to increase to rt. The solvent was evaporated and the product (XII) was obtained by precipita- Procedure D—General Procedure for the Synthesis of Compound 74

Compound 74 and analogues can be prepared in a multi-step synthesis following methods known and described in literature (for example: Liu K.-C., et al.; A particularly convenient preparation of benzohydroximinoyl chlorides (nitrile oxide precursors). *Journal of Organic Chemistry*, 45 (1980), 3916-3918; Johnson J. E., et al.; Bisamidoximes: Synthesis and Complexation with Iron(III). *Australian Journal of Chemistry*, 60 (2007), 685-690; Moehrle H., et al.; Assistance of N,N-disubstituted amidoximes in cyclodehydrogenation reactions. *Zeitschrift fuer Naturforschung, B: Chemical Sciences*, 47 (1992), 1333-1340).

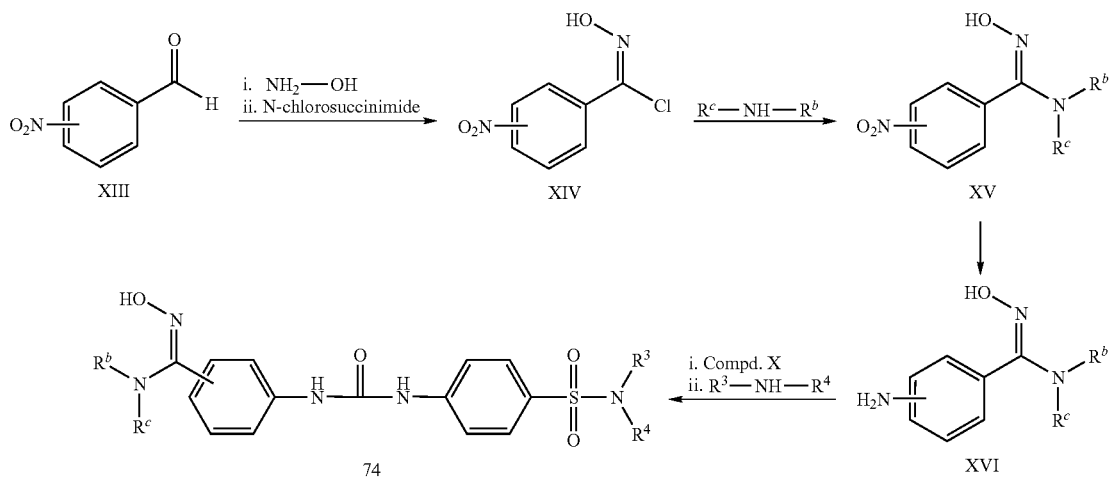

0.13 mol of compound XIII were dissolved in dry DMF. 0.14 mol each of sodium acetate and hydroxylamine hydrochloride were added and the mixture was stirred overnight at rt. After removal of the solvent, the oxime was precipitate from MeOH/diethylether (yield 70%). This compound was dissolved in dry DMF and 1.1 eq of N-chlorosuccinimide was added portionwise over 30 min. The mixture was stirred overnight at rt, then it was poured into ice-water. The suspension was extracted with ethylacetate and the organic solution was washed with water and brine. Compound XIV was obtained after removal of the organic solvent. Compound XIV was dissolved in DCM and 1 eq of methyl piperazine-1-carboxylate (or another secondary amine) were added in the presence of 2.1 eq of DIEA. The mixture was stirred for 24 h at rt, the solvent was removed and the residue was taken into ethylacetate. The organic solution was washed with water and brine and was evaporated. The obtained oil was purified by flash chromatography with silica gel and a mixture DCM/MeOH 95:5 as eluent. The nitro compound XV was reduced by hydrogenation with palladium catalyst to produce the corresponding amino compound XVI. Compound XVI was reacted with 1 eq of compound X in DCM until complete conversion to the corresponding diarylurea. The solvent was removed and the residue was dissolved in dry DMF. To this solution, 1 eq of the corresponding amino compound and 1 eq of DIEA was added. The solution was stirred at 70° C. overnight, then the solvent was removed and compound 74 was obtained after purification by preparative HPLC.

List of Compounds 4-(3-(3-((4-butylpiperazin-1-yl)(imino)methyl)phenyl)ureido)benzenesulfonamide (1)

The title compound was obtained following procedure A and using 3 equivalents of n-butylpiperazine as secondary amine.
Yield: 15%.
[M+H]$^+$: 459.1.
$^1$H NMR (DMSO-d$_6$): 11.45 (s, 1H, NH), 11.44 (s, 1H, NH), 7.87 (t broad, 1H, ArH), 7.77-7.68 (m, 5H, ArH), 7.49 (t, 1H, J=7.9 Hz, ArH), 7.14 (s, 2H, NH$_2$), 7.10 (d, 1H, J=7.1 Hz, ArH), water signal partially covers a group of signals, 2.34 (t, 2H, J=7.2 Hz, NCH$_2$), 1.40 (m, 2H, CH$_2$), 1.29 (m, 2H, CH$_2$), 0.88 (t, 3H, J=7.2, CH$_3$).

4-(3-(3-((4-hydroxypiperazin-1-yl)(imino)methyl)phenyl)ureido) benzenesulfonamide (2)

The title compound was obtained following procedure A and using 2 equivalents of 4-hydroxypiperidine as secondary amine.
Yield: 2%.
[M+H]$^+$: 418.0.

4-(3-(3-(imino(piperazin-1-yl)methyl)phenyl)ureido) benzenesulfonamide (3)

The title compound was obtained following procedure A and using 2 equivalents of piperazine as secondary amine.
Yield: 13%.
[M+H]$^+$: 403.0.

1-(4-(4-bromophenylsulfonyl)phenyl)-3-(3-((4-butylpiperazin-1-yl)(imino)methyl)phenyl)urea (4)

The title compound was obtained following procedure B2 (with 4-(4-bromophenylsulfonyl)aniline) and using 1.14 equivalents of 4-hydroxypiperidine as secondary amine. The product was purified by flash chromatography.
Yield: 27%.
[M+H]$^+$: 599.1.

1-(4-(4-bromophenylsulfonyl)phenyl)-3-(3-((4-hydroxypiperidin-1-yl)(imino)methyl)phenyl)urea (5)

The title compound was obtained following procedure B1 or B2 (with 4-(4-bromophenylsulfonyl)aniline) and using 2 equivalents of 4-hydroxypiperidine as secondary amine. The product was purified by preparative HPLC.
Yield: 9%.
[M+H]$^+$: 556.6
$^1$H NMR (DMSO-d$_6$): 9.59 (s, 1H, NH); 9.42 (s, 1H, NH); 9.30 (s, 1H, NH); 9.02 (s, 1H, NH); 7.82-7.43 (m, 11H, Ar—H); 7.13 (m, 1H, Ar—H); 4.88 (d, 1H, J=3.5 Hz, OH); 3.84-3.13 (m, 5H, CH+2CH$_2$) water signal partly covers this group of signals; 1.92-1.34 (m, 4H, 2CH$_2$).

1-(3-(imino(morpholino)methyl)phenyl)-3-(4-(4-nitrophenylsulfonyl)phenyl)urea (6)

The title compound was obtained following procedure B2 with 4-(4-nitrophenylsulfonyl)aniline and using 0.8 equivalents of morpholine as secondary amine. The product was purified by flash chromatography.

Yield: 2%.

[M+H]$^+$: 510.1.

1-(3-(imino(pyrrolidin-1-yl)methyl)phenyl)-3-(4-(4-nitrophenylsulfonyl)phenyl)urea (7)

The title compound was obtained following procedure B2 with 4-(4-nitrophenylsulfonyl)aniline and using 0.8 equivalents of pyrrolidine as secondary amine. The product was purified by flash chromatography.

Yield: 5%.

[M+H]$^+$: 494.0.

$^1$H NMR (DMSO-d$_6$): 10.09 (s, 1H, NH); 9.86 (s, 1H, NH); 9.25-8.65 (broad, 2H, NH$_2$); 8.31 (m, 2H, Ar—H); 8.10 (m, 2H, Ar—H); 7.85 (m, 2H, Ar—H); 7.73 (m, 1H, Ar—H); 7.63 (m, 2H, Ar—H); 7.52 (m, 1H, Ar—H); 7.43 (m, 1H, Ar—H); 7.14 (m, 1H, Ar—H); 3.46-3.28 (broad, 4H, 2NCH$_2$) water signal partly covers this group of signals; 1.96-1.80 (broad, 4H, 2CH$_2$).

1-(3-(imino(4-methylpiperazin-1-yl)methyl)phenyl)-3-(4-(4-nitrophenylsulfonyl)phenyl)urea (8)

The title compound was obtained following procedure B2 with 4-(4-nitrophenylsulfonyl)aniline and using 1.5 equivalents of 1-methylpiperazine. The product was purified by flash chromatography.

Yield: 18%.

[M+H]$^+$: 523.2

$^1$H NMR (DMSO-d$_6$): 10.18 (broad, 1H, NH); 9.96 (broad, 1H, NH); 9.51 (broad, 1H, NH); 9.26 (broad, 1H, NH); 8.39 (m, 2H, Ar—H); 8.18 (m, 2H, Ar—H); 7.94 (m, 2H, Ar—H); 7.76 (m, 1H, Ar—H); 7.71 (m, 2H, Ar—H); 7.63 (m, 1H, Ar—H); 7.53 (m, 1H, Ar—H); 7.18 (m, 1H, Ar—H); 3.76-3.28 (broad, 4H, 2NCH$_2$) water signal partly covers this group of signals; 2.55-2.38 (broad, 4H, 2NCH$_2$) DMSO signal partly covers this group of signals; 2.23 (s, 3H, CH$_3$).

1-(3-(imino(thiazolidin-3-yl)methyl)phenyl)-3-(4-(4-nitrophenylsulfonyl)phenyl)urea (9)

The title compound was obtained following procedure B2 with 4-(4-nitrophenylsulfonyl)aniline and using 1.5 equivalents of thiazolidine as secondary amine. The product was purified by flash chromatography.

Yield: 1%.

[M+H]$^+$: 512.1.

1-(3-((4-hydroxypiperidin-1-yl)(imino)methyl)phenyl)-3-(4-(4-nitrophenylsulfonyl)phenyl)urea (10)

The title compound was obtained following procedure B1 or B2 with 4-(4-nitrophenylsulfonyl)aniline and using 1.5 equivalents of 4-hydroxypiperidine as secondary amine. The product was purified by flash chromatography.

Yield: 10%.

[M+H]$^+$: 524.1.

$^1$H NMR (DMSO-d$_6$):10.13 (s, 1H, NH); 9.91 (s, 1H, NH); 9.37-9.16 (broad, 2H, NH); 8.29 (AB, 4H, J=63.3 Hz, 8.9 Hz, Ar—H); 7.82 (AB, 4H, J=67.0 Hz, 8.9 Hz, Ar—H); 7.78 (s, 1H, Ar—H); 7.61 (m, 1H, Ar—H); 7.52 (t, 1H, J=7.9 Hz, Ar—H); 7.19 (m, 1H, Ar—H); 4.95 (d, 1H, J=3.6 Hz, OH); 3.87-3.83 (broad, 1H, CH); 3.60-3.10 (broad, 4H, 2NCH$_2$) water signal partly covers this group of signals; 2.00-1.40 (broad, 4H, 2CH$_2$).

1-(4-(4-chlorophenylsulfonyl)phenyl)-3-(3-((4-hydroxypiperidin-1-yl)(imino)methyl)phenyl)urea (11)

The title compound was obtained following procedure B2 with 4-(4-chlorophenylsulfonyl)aniline and using 1.2 equivalents of piperidin-4-ol as secondary amine. The product was purified by preparative HPLC.

Yield: 14%.

[M+H]$^+$: 513.0.

$^1$H NMR (DMSO-d$_6$): 10.44 (s, 1H, NH); 9.33 (broad, 1H, NH); 9.26 (s, 1H, NH); 9.05 (broad, 1H, NH); 7.91-7.80 (m, 5H, Ar—H); 7.70-7.64 (m, 4H, Ar—H); 7.56-7.47 (m, 2H, Ar—H); 7.18-7.16 (m, 1H, Ar—H); 4.91 (d, 1H, J=3.6 Hz, OH); 3.86-3.79 (broad, 1H, CH); water signal covers the group of 2NCH$_2$ signals; 1.84-1.52 (broad, 4H, 2CH$_2$).

1-(4-(4-bromophenylsulfonyl)phenyl)-3-(3-((4-(hydroxymethyl)piperidin-1-yl)(imino)methyl)phenyl) urea (12)

The title compound was obtained following procedure B2 with 4-(4-bromophenylsulfonyl)aniline and using 1.14 equivalents of piperidin-4-ylmethanol as secondary amine. The residue was taken into ethylacetate and washed with 5% NaHCO$_3$, water and brine. The product was obtained after crystallization with methanol/ethyl ether.

Yield: 20%.

[M+H]$^+$: 570.9.

$^1$H NMR (DMSO-d$_6$): 10.22 (broad, 1H, NH); 10.03 (broad, 1H, NH); 9.40 (broad, 2H, NH); 8.11-7.86 (m, 9H, Ar—H); 7.84-7.79 (m, 1H, Ar—H); 7.76-7.68 (m, 1H, Ar—H); 7.39-7.35 (m, 1H, Ar—H); 4.76 (t, 1H, J=5.0 Hz, OH); 4.07-4.02 (broad, 2H, CH$_2$); water signal partially covers the group of 2NCH$_2$ signals; 2.01-1.94 (broad, 3H, CH+CH$_2$); 1.50-1.40 (broad, 2H, CH$_2$).

3-(3-(4-(4-bromophenylsulfonyl)phenyl)ureido)-N,N-bis(2-methoxyethyl)benzimidamide (13)

The title compound was obtained following procedure B2 with 4-(4-bromophenylsulfonyl)aniline and using 1.14 equivalents of bis(2-methoxyethyl)amine as secondary amine. The residue was taken into ethylacetate and washed with 5% NaHCO$_3$, water and brine. The product was obtained by crystallization with MeOH/ethyl ether.

Yield: 30%.

[M+H]$^+$: 589.1.

1-(4-(4-bromophenylsulfonyl)phenyl)-3-(3-(imino(thiomorpholino)methyl)phenyl)urea (14)

The title compound was obtained following procedure B2 with 4-(4-bromophenylsulfonyl)aniline and using 1.14 equivalents of thiomorpholine as secondary amine. The product was purified by flash chromatography.

Yield: 25%.

[M+H]$^+$: 559.0.

1-(4-(4-bromophenylsulfonyl)phenyl)-3-(3-(imino(pyrrolidin-1-yl)methyl)phenyl)urea (15)

The title compound was obtained following procedure B2 with 4-(4-bromophenylsulfonyl)aniline and using 1.14 equivalents of pyrrolidine as secondary amine. The product was purified by flash chromatography.

Yield: 38%.

[M+H]$^+$: 527.0.

1-((3-(3-(4-(4-bromophenylsulfonyl)phenyl)ureido) phenyl)(imino)methyl)piperidine-4-carboxamide (16)

The title compound was obtained following procedure B2 with 4-(4-bromophenylsulfonyl)aniline and using 1.14 equivalents of piperidine-4-carboxamide as secondary amine. The product precipitated directly from the reaction mixture and was filtered, washed with cold diethylether and dried.

Yield: 54%.
$[M+H]^+$: 584.0.

1-(4-(4-aminophenylsulfonyl)phenyl)-3-(3-((4-hydroxypiperidin-1-yl)(imino)methyl)phenyl)urea (17)

A suspension of tin(II) chloride dihydrate (3 equivalents) in concentrated acetic acid was treated with a 3 M solution of chloridric acid in methanol for 30 minutes. The resulting suspension was added portionwise to a solution of 1-(3-((4-hydroxypiperidin-1-yl) (imino)methyl)phenyl)-3-(4-(4-nitrophenyl sulfonyl)phenyl)urea (10) in acetic acid. The resulting solution was stirred 2 hours at 85° C. The reaction mixture was quenched with a 5% NaOH aqueous solution, and extracted with ethyl acetate. The title compound was obtained after preparative HPLC.

Yield: 18%.
$[M+H]^+$: 494.1.
$^1$H NMR (DMSO-$d_6$): 11.30 (s, 1H, NH); 11.22 (s, 1H, NH); 7.81 (m, 1H, Ar—H); 7.72-7.66 (m, 5H, Ar—H); 7.52-7.41 (m, 3H, Ar—H); 7.10-7.06 (m, 1H, Ar—H); 6.62-6.57 (m, 2H, Ar—H); 6.05 (s broad, 2H, NH$_2$); 3.87-3.76 (m, 1H, CH); 3.75-3.67 (m, 2H, NCH$_2$); water signal partially covers a group of signals; 1.90-1.78 (broad, 2H, CH$_2$); 1.58-1.44 (broad, 2H, CH$_2$).

4-(3-(3-((4-butylpiperazin-1-yl)(imino)methyl)phenyl)ureido)-N-methylbenzene sulfonamide (18)

The title compound was prepared from 4-(3-(3-cyanophenyl)ureido)-N-methylbenzenesulfonamide following procedure C and using 2.2 equivalents of n-butylpiperazine as secondary amine. The product was purified by preparative HPLC.

Yield: 1%.
$[M+H]^+$: 473.2.

4-(3-(3-((4-butylpiperazin-1-yl)(imino)methyl)phenyl)ureido)-N-propylbenzene sulfonamide (19)

The title compound was prepared from 3-(3-(4-(N-propylsulfamoyl)phenyl)ureido)benzimidamide following procedure C and using 2 equivalents of n-butylpiperazine as secondary amine. The product was purified by preparative HPLC.

Yield: 13%.
$[M+H]^+$: 501.3.
$^1$H NMR (DMSO-$d_6$): 9.77-9.27 (m broad, 3H, NH); 7.86 (broad, 1H, Ar—H); 7.66-7.46 (m, 6H, NH+Ar—H); 7.32 (m, 1H, Ar—H); 7.18-7.13 (m, 1H, Ar—H); water signal partially covers a group of signals; 2.65-2.57 (m, 2H, CH$_2$); 1.58-1.44 (broad, 2H, CH$_2$); 1.36-1.20 (m, 4H, 2CH$_2$); 0.84 (t, 3H, J=7.3 Hz, CH$_3$); 0.72 (t, 3H, J=7.4 Hz, CH$_3$).

4-(3-(3-((4-butylpiperazin-1-yl)(imino)methyl)phenyl)ureido)-N,N-bis(2-hydroxyethyl)benzenesulfonamide (20)

The title compound was prepared from 4-(3-(3-cyanophenyl)ureido)-N,N-bis(2-hydroxyethyl)benzenesulfonamide following procedure C and using 2 equivalents of n-butylpiperazine as secondary amine. The product was purified by preparative HPLC.

Yield: 18%.
$[M+H]^+$: 547.2.
$^1$H NMR (DMSO-$d_6$): 9.81 (broad, 2H, NH); 9.48 (broad, 1H, NH); 7.97 (broad, 1H, Ar—H); 7.79-7.57 (m, 6H, Ar—H); 7.29-7.24 (m, 1H, Ar—H); 3.55 (t, 4H, J=6.3 Hz, 2CH$_2$); 3.18 (t, 4H, J=6.3 Hz, 2CH$_2$); water signal partially covers a group of signals; 1.68-1.56 (broad, 2H, CH$_2$); 1.43-1.31 (m, 2H, CH$_2$); 0.95 (t, 3H, J=7.3 Hz, CH$_3$).

1-(3((4-butylpiperazin-1-yl)(imino)methyl)phenyl)-3-(4-(morpholinosulfonyl)phenyl)urea (21)

The title compound was prepared from 1-(3-cyanophenyl)-3-(4-(morpholinosulfonyl)phenyl)urea following procedure C and using 2 equivalents of n-butylpiperazine as secondary amine. The product was purified by preparative HPLC.

Yield: 72%.
$[M+H]^+$: 529.2.
$^1$H NMR (DMSO-$d_6$): 9.83-9.13 (broad, 3H, 3NH); 7.90 (broad, 1H, Ar—H); 7.80-7.56 (m, 6H, Ar—H); 7.28-7.22 (m, 1H, Ar—H); 3.67 (m, 4H, 2CH$_2$); 2.89 (m, 4H, 2CH$_2$); water signal partially covers a group of signals; 1.60-1.42 (broad, 2H, CH$_2$); 1.41-1.28 (m, 2H, CH$_2$); 0.93 (t, 3H, J=7.2 Hz, CH$_3$).

4-(3-(3-((4-butylpiperazin-1-yl)(imino)methyl)phenyl)ureido)-N-(7-chloroquinolin-4-yl)benzenesulfonamide (22)

The title compound was prepared from N-(7-chloroquinolin-4-yl)-4-(3-(3-cyanophenyl)ureido)benzenesulfonamide following procedure C and using 2.2 equivalents of n-butylpiperazine as secondary amine. The product was purified by preparative HPLC.

Yield: 25%.
$[M+H]^+$: 620.2.
$^1$H NMR (DMSO-$d_6$): 9.78-9.59 (broad, 2H, 2NH); 8.38 (d, 1H, J=8.9 Hz, Quin-H); 8.26 (s, 1H, NH); 8.14 (d, 1H, J=6.1 Hz, Quin-H), 7.83 (m, 1H, Ar—H); 7.72 (m, 2H, Ar—H); 7.64 (d, 1H, J=2.1 Hz, Quin-H); 7.62-7.46 (m, 4H, Ar—H); 7.33 (dd, 1H, J=8.9 Hz, 2.2 Hz, Quin-H); 7.13 (m, 1H, Ar—H); 6.91 (d, 1H, J=6.1 Hz, Quin-H); water signal partially covers a group of signals; 1.46-1.22 (m, 4H, 2CH$_2$); 0.88 (t, 3H, J=7.2 Hz, CH$_3$).

4-(3-(3-((4-butylpiperazin-1-yl)(imino)methyl)phenyl)ureido)-N-(4-sulfamoylphenyl)benzenesulfonamide (23)

The title compound was prepared from 4-(3-(3-cyanophenyl)ureido)-N-(4-sulfamoylphenyl)benzenesulfonamide following procedure C and using 1.2 equivalents of n-butylpiperazine as secondary amine. The product was purified by preparative HPLC.

Yield: 16.5%.
$[M+H]^+$: 614.2.
$^1$H NMR (DMSO-$d_6$): 10.10-9.31 (broad, 3H, 3NH); 7.82-7.48 (m, 9H, Ar—H); 7.25-7.16 (m, 3H, Ar—H); 7.15 (s broad, 2H, NH$_2$); water signal partially covers a group of signals; 2.33 (t, 2H, J=7.2 Hz, CH$_2$); 1.46-1.22 (2m, 4H, 2CH$_2$); 0.88 (t, 3H, J=7.2 Hz, CH$_3$).

methyl 4-(imino(3-(3-(4-(N-(4-sulfamoylphenyl)sulfamoyl)phenyl)ureido)phenyl)methyl)piperazine-1-carboxylate (24)

The title compound was prepared from 4-(3-(3-cyanophenyl)ureido)-N-(4-sulfamoylphenyl)benzenesulfonamide following procedure C and using 1 equivalent of methyl piperazine-1-carboxylate as secondary amine and 1 equivalent of DIEA as base. The product was purified by preparative HPLC.
Yield: 5.3%.
[M+H]$^+$: 616.0.

4-(3-(3-(imino(morpholino)methyl)phenyl)ureido)-N-(4-sulfamoylphenyl)benzenesulfonamide (25)

The title compound was prepared from 4-(3-(3-cyanophenyl)ureido)-N-(4-sulfamoylphenyl)benzenesulfonamide following procedure C and using 1 equivalent of morpholine as secondary amine and 0.5 equivalent of DIEA as base. The product was purified by preparative HPLC.
Yield: 31.6%.
[M+H]$^+$: 559.1.
$^1$H NMR (DMSO-d$_6$): 10.69-9.10 (broad, 3H, 3NH); 8.44 (broad, 1H, NH); 7.81 (m, 1H, Ar—H); 7.75-7.59 (m, 7H, Ar—H); 7.49 (m, 1H, Ar—H); 7.22-7.08 (m, 5H, Ar—H+NH$_2$); 3.73 (broad, 4H, 2CH$_2$); 3.54 (broad, 4H, 2CH$_2$); water signal interferes with these two signals.

4-(3-(3-(imino(4-methylpiperazin-1-yl)methyl)phenyl)ureido)-N-(4-sulfamoylphenyl)benzenesulfonamide (26)

The title compound was prepared from 4-(3-(3-cyanophenyl)ureido)-N-(4-sulfamoylphenyl)benzenesulfonamide following procedure C and using 1 equivalent of 1-methylpiperazine as secondary amine and 1 equivalent of DIEA as base. The product was purified by preparative HPLC.
Yield: 33.8%.
[M+H]$^+$: 572.1.
$^1$H NMR (DMSO-d$_6$): 10.45 (broad, 1H, NH); 10.34 (broad, 1H, NH); 8.21 (s, 1H, NH); 7.77-7.60 (m, 8H, Ar—H); 7.51 (m, 1H, Ar—H); 7.27-7.21 (m, 2H, Ar—H); 7.19-7.12 (m, 3H, Ar—H+NH$_2$); water signal partially covers a group of signals; 2.23 (s, 3H, CH$_3$).

4-(3-(3-(imino(4-oxopiperidin-1-yl)methyl)phenyl)ureido)-N-(4-sulfamoylbenzyl)benzenesulfonamide (27)

The title compound was prepared from 4-(3-(3-cyanophenyl)ureido)-N-(4-sulfamoylbenzyl)benzenesulfonamide following procedure C and using 2.2 equivalent of both 4-piperidone as secondary amine and DIEA as base. The product was purified first by preparative HPLC and finally with a preparative TLC (eluent: petrolether/DCM/MeOH 2:3:1 containing 2% of a 7 M NH$_3$ solution in MeOH).
Yield: 3%.
[M+H]$^+$: 585.2.
$^1$H NMR (DMSO-d$_6$): 9.69 (broad, 1H, NH); 9.62 (broad, 1H, NH); 8.08 (t, 1H, J=6.3 Hz, NH); 7.92 (m, 1H, Ar—H); 7.77-7.52 (m, 8H, Ar—H); 7.46-7.41 (m, 2H, Ar—H); 7.30-7.23 (m, 3H, Ar—H+NH$_2$); 4.03 (d, 2H, J=6.3 Hz, CH$_2$); 3.82 (broad, 4H, 2CH$_2$); 2.64 (broad, 4H, 2CH$_2$).

4-(3-(3-((4-(2-hydroxyethyl)piperazin-1-yl)(imino)methyl)phenyl)ureido)-N-(4-sulfamoylbenzyl)benzenesulfonamide (28)

The title compound was prepared from 4-(3-(3-cyanophenyl)ureido)-N-(4-sulfamoylbenzyl)benzenesulfonamide following procedure C and using 1.2 equivalent of 2-(piperazin-1-yl)ethanol as secondary amine. The product was purified by preparative TLC (eluent: petrolether/DCM/MeOH 2:3:1 containing 2% of a 7 M NH$_3$ solution in MeOH).
Yield: 2%.
[M+H]$^+$: 616.1.
$^1$H NMR (DMSO-d$_6$): 10.12 (broad, 1H, NH); 10.05 (broad, 1H, NH); 8.09 (t, 1H, J=6.2 Hz, NH); 7.79-7.62 (m, 8H, Ar—H); 7.53 (m, 1H, Ar—H); 7.47-7.41 (m, 2H, Ar—H); 7.29 (s broad, 2H, NH$_2$); 7.19-7.15 (m, 1H, Ar—H); 4.47 (t, 1H, J=5.3 Hz, OH); 4.03 (d, 2H, J=6.0 Hz, CH$_2$); 3.51 (m, 2H, OCH$_2$); water signal partially covers a group of signals; 2.59 (broad, 4H, 2CH$_2$).

4-(3-(3((4-(hydroxymethyl)piperidin-1-yl)(imino)methyl)phenyl)ureido)-N-(4-sulfamoylbenzyl)benzenesulfonamide (29)

The title compound was prepared from 4-(3-(3-cyanophenyl)ureido)-N-(4-sulfamoylbenzyl)benzenesulfonamide following procedure C and using 2.2 equivalents of 4-piperidinylmethanol as secondary amine. The product was purified by preparative HPLC.
Yield: 40%.
[M+H]$^+$: 601.1.
$^1$H NMR (DMSO-d$_6$): 9.61 (broad, 1H, NH); 9.54 (broad, 1H, NH); 8.08 (t, 1H, J=6.2 Hz, NH); 7.83 (m, 1H, Ar—H); 7.79-7.41 (m, 11H, Ar—H); 7.28 (s broad, 2H, NH$_2$); 7.20-7.16 (m, 1H, Ar—H); 4.57 (t, 1H, J=5.1 Hz, OH); 4.03 (d, 2H, J=6.1 Hz, CH$_2$); water signal partially covers a group of signals; 1.89-1.70 (broad, 3H, CH+CH$_2$); 1.40-1.20 (broad, 2H, CH$_2$).

N-ethyl-N-(2-hydroxyethyl)-3-(3-(4-(N-(4-sulfamoylbenzyl)sulfamoyl)phenyl)ureido) benzimidamide (30)

The title compound was prepared from 4-(3-(3-cyanophenyl)ureido)-N-(4-sulfamoylbenzyl)benzenesulfonamide following procedure C and using 1.1 equivalents of 2-(ethylamino)ethanol as secondary amine. The product was purified by preparative HPLC.
Yield: 7%.
[M+H]$^+$: 575.1.

4-(3-(3-(imino(thiomorpholino)methyl)phenyl)ureido)-N-(4-sulfamoylbenzyl)benzenesulfonamide (31)

The title compound was prepared from 4-(3-(3-cyanophenyl)ureido)-N-(4-sulfamoylbenzyl)benzenesulfonamide following procedure C and using 1.1 equivalents of thiomorpholine as secondary amine. The product was purified by preparative TLC (eluent DCM/MeOH 8:2).
Yield: 28%.
[M+H]$^+$: 589.0.
$^1$H NMR (DMSO-d$_6$): 9.74 (broad, 1H, NH); 9.67 (broad, 1H, NH); 8.08 (t, 1H, J=6.3 Hz, NH); 7.87 (m, 1H, Ar—H); 7.77-7.51 (m, 8H, Ar—H); 7.46-7.41 (m, 2H, Ar—H); 7.28 (s broad, 2H, NH$_2$); 7.24-7.20 (m, 1H, Ar—H); 4.03 (d, 2H, J=6.2 Hz, CH$_2$); water signal partially covers a group of signals; 2.85-2.80 (m, 4H, 2CH$_2$).

N,N-bis(2-methoxyethyl)-3-(3-(4-(N-(4-sulfamoylbenzyl)sulfamoyl)phenyl)ureido)benzimidamide (32)

The title compound was prepared from 4-(3-(3-cyanophenyl)ureido)-N-(4-sulfamoylbenzyl)benzenesulfonamide following procedure C and using 1.1 equivalents of bis(2-methoxyethyl)amine as secondary amine. The product was purified by preparative HPLC.
Yield: 11%.
[M+H]$^+$: 619.1.
$^1$H NMR (DMSO-d$_6$): 9.62 (broad, 1H, NH); 9.56 (broad, 1H, NH); 8.07 (t, 1H, J=6.3 Hz, NH); 7.79-7.41 (m, 13H, Ar—H); 7.28 (s broad, 2H, NH$_2$); 7.14-7.11 (m, 1H, Ar—H); 4.03 (d, 2H, J=6.2 Hz, CH$_2$); 3.82-3.48 (broad, 8H, 4-CH$_2$); water signal partially covers a group of signals.

1-(imino(3-(3-(4-(N-(4-sulfamoylbenzyl)sulfamoyl)phenyl)ureido)phenyl)methyl)piperidine-4-carboxamide (33)

The title compound was prepared from 4-(3-(3-cyanophenyl)ureido)-N-(4-sulfamoylbenzyl)benzenesulfonamide following procedure C and using 2.2 equivalents of piperidine-4-carboxamide as secondary amine. The product was purified by preparative HPLC.
Yield: 40%.
[M+H]$^+$: 614.1.
$^1$H NMR (DMSO-d$_6$): 9.63 (broad, 1H, NH); 9.56 (broad, 1H, NH); 8.08 (broad, 1H, NH); 7.84 (m, 1H, Ar—H); 7.77-7.42 (m, 10H, Ar—H); 7.32 (broad, 1H, NH$_2$); 7.28 (broad, 2H, NH$_2$); 7.21-7.18 (m, 1H, Ar—H); 6.87 (broad, 1H, NH$_2$); 4.04-4.02 (broad, 2H, CH$_2$); water signal partially covers a group of signals; 1.92-1.62 (broad, 4H, Ar—H).

4-(3-(3-((4-butylpiperazin-1-yl)(imino)methyl)phenyl)ureido)-N-(4-sulfamoylbenzyl)benzenesulfonamide (34)

The title compound was prepared from 4-(3-(3-cyanophenyl)ureido)-N-(4-sulfamoylbenzyl)benzenesulfonamide following procedure C and using 1.1 equivalents of n-butylpiperazine as secondary amine. The product was purified by preparative HPLC.
Yield: 21%.
[M+H]$^+$: 628.1.
$^1$H NMR (DMSO-d$_6$): 9.81 (broad, 1H, NH); 9.77 (broad, 1H, NH); 9.44 (broad, 1H, NH); 8.08 (t, 1H, J=6.3 Hz, NH); 7.93 (m, 1H, Ar—H); 7.76-7.53 (m, 8H, Ar—H); 7.45-7.41 (m, 2H, Ar—H); 7.28 (broad, 2H, NH$_2$); 7.25-7.21 (m, 1H, Ar—H); 4.03 (d, 2H, J=6.3 Hz, CH$_2$); water signal partially covers a group of signals; 1.64-1.53 (broad, 2H, CH$_2$); 1.33 (m, 2H, CH$_2$); 0.91 (t, 3H, J=7.3 Hz, CH$_3$).

4-(3-(3-((4-butylpiperazin-1-yl)(imino)methyl)phenyl)ureido)-N-(2,3,6-trifluorobenzyl)benzenesulfonamide (35)

The title compound was prepared from 4-(3-(3-cyanophenyl)ureido)-N-(2,3,6-trifluorobenzyl)benzenesulfonamide following procedure C and using 3 equivalents of n-butylpiperazine as secondary amine. The product was purified by preparative HPLC.
Yield (8%)
[M+H]$^+$: 603.2.
$^1$H NMR (DMSO-d$_6$): 11.00 (broad, 1H, NH); 10.97 (broad, 1H, NH); 8.03 (broad, 1H, NH); 7.83 (m, 1H, Ar—H); 7.74-7.63 (m, 5H, Ar—H); 7.51-7.33 (m, 2H, Ar—H); 7.13-7.00 (m, 2H, Ar—H); 4.02 (broad, 2H, CH$_2$); water signal partially covers a group of signals; 2.33 (m, 2H, CH$_2$); 1.46-1.23 (m, 4H, 2CH$_2$); 0.88 (t, 3H, J=7.2 Hz, CH$_3$).

N-benzyl-4-(3-(3-((4-butylpiperazin-1-yl)(imino)methyl)phenyl)ureido) benzenesulfonamide (36)

The title compound was prepared from N-benzyl-4-(3-(3-cyanophenyl)ureido)benzenesulfonamide following procedure C and using 3 equivalents of n-butylpiperazine as secondary amine. The product was purified by preparative HPLC.
Yield: 6%.
[M+H]$^+$: 549.2.
$^1$H NMR (DMSO-d$_6$): 11.28-11.14 (broad, 2H, 2NH); 8.52 (s broad, 1H, NH); 7.94-7.87 (broad, 1H, NH); 7.83 (m, 1H, Ar—H); 7.75-7.67 (m, 5H, Ar—H); 7.47 (m, 1H, Ar—H); 7.32-7.19 (m, 5H, Ar—H); 7.11-7.07 (m, 1H, Ar—H); 3.95 (s broad, 2H, CH$_2$); water signal partially covers a group of signals; 2.33 (m, 2H, CH$_2$); 1.46-1.23 (m, 4H, 2CH$_2$); 0.88 (t, 3H, J=7.2 Hz, CH$_3$).

4-(3-(3-((4-ethylpiperazin-1-yl)(imino)methyl)phenyl)ureido)-N-(4-sulfamoylbenzyl)benzenesulfonamide (37)

The title compound was prepared from 4-(3-(3-cyanophenyl)ureido)-N-(4-sulfamoylbenzyl)benzenesulfonamide following procedure C and using 1.5 equivalents of 1-ethylpiperazine as secondary amine. The product was purified by flash chromatography on silica gel.
Yield: 30%.
[M+H]$^+$: 600.1.

4-(3-(3-(imino(4-propylpiperazin-1-yl)methyl)phenyl)ureido)-N-(4-sulfamoylbenzyl)benzenesulfonamide (38)

The title compound was prepared from 4-(3-(3-cyanophenyl)ureido)-N-(4-sulfamoylbenzyl)benzenesulfonamide following procedure C and using 2 equivalents of n-propylpiperazine as secondary amine. The product was purified by preparative HPLC.
Yield: 30%.
[M+H]$^+$: 614.1.
$^1$H NMR (DMSO-d$_6$): 9.80 (s broad, 1H, NH); 9.75 (s broad, 1H, NH); 9.70 (s broad, 1H, NH); 9.45 (s broad, 1H, NH); 8.08 (t, 1H, J=6.3 Hz, NH); 7.93 (m, 1H, Ar—H); 7.76-7.62 (m, 7H, Ar—H); 7.56 (m, 1H, Ar—H); 7.45-7.41 (m, 2H, Ar—H); 7.28 (s broad, 2H, NH$_2$); 7.25-7.21 (m, 1H, Ar—H); 4.04 (d, 2H, J=6.3 Hz, CH$_2$); water signal partially covers a group of signals; 1.70-1.58 (m broad, 2H, CH$_2$); 0.92 (t, 3H, J=7.4 Hz, CH$_3$).

4-(3-(3((4-allylpiperazin-1-yl)(imino)methyl)phenyl) ureido)-N-(4-sulfamoylbenzyl)benzenesulfonamide (39)

The title compound was prepared from 4-(3-(3-cyanophenyl)ureido)-N-(4-sulfamoylbenzyl)benzenesulfonamide following procedure C and using 5 equivalents of 1-allylpiperazine as secondary amine. The product was purified by preparative HPLC.
Yield: 3%.
[M+H]$^+$: 612.1.

4-(2-(4-(3-(3-((4-butylpiperazin-1-yl)(imino)methyl) phenyl)ureido)phenylsulfonyl) hydrazinyl)benzenesulfonamide (40)

The title compound was prepared from 4-(2-(4-(3-(3-cyanophenyl)ureido)phenylsulfonyl) hydrazinyl)benzenesulfonamide following procedure C and using 2 equivalents of n-butylpiperazine as secondary amine. The product was purified by preparative HPLC.
Yield: 10%.
[M+H]$^+$: 629.1.

2-(4-(3-(3-((4-butylpiperazin-1-yl)(imino)methyl) phenyl)ureido)phenylsulfonyl)isoindoline-5-sulfonamide (41)

The title compound was prepared from 2-(4-(3-(3-cyanophenyl)ureido)phenylsulfonyl)isoindoline-5-sulfonamide following procedure C and using 3 equivalents of n-butylpiperazine as secondary amine. The product was purified by preparative HPLC.
Yield: 12%.
[M+H]$^+$: 640.2.
$^1$H NMR (DMSO-d$_6$): 11.37-11.17 (broad, 2H, 2NH), 7.81-7.87 (m, 7H, Ar—H); 7.50-7.41 (m, 2H, Ar—H); 7.28 (broad, 2H, NH$_2$); 7.12-7.09 (m, 1H, Ar—H); 4.64-4.59 (m, 4H, 2CH$_2$); water signal partially covers a group of signals; 2.33 (m, 2H, CH$_2$); 1.45-1.22 (m, 4H, 2CH$_2$); 0.88 (t, 3H, J=7.2 Hz, CH$_3$).

4-(3-(3-((4-butylpiperazin-1-yl)(imino)methyl)phenyl)ureido)-N-(1-(4-sulfamoylphenyl)ethyl)benzenesulfonamide (42)

The title compound was prepared from 4-(3-(3-cyanophenyl)ureido)-N-(1-(4-sulfamoylphenyl)ethyl)benzenesulfonamide following procedure C and using 2 equivalents of n-butylpiperazine as secondary amine. The product was purified by preparative HPLC.
Yield: 8%.
[M+H]$^+$: 642.2.

4-(3-(3-(imino(morpholino)methyl)phenyl)ureido)-N-(4-sulfamoylbenzyl)benzenesulfonamide (43)

The title compound was prepared from 4-(3-(3-cyanophenyl)ureido)-N-(4-sulfamoylbenzyl)benzenesulfonamide following procedure C and using 2 equivalents of morpholine as secondary amine. The product was purified by preparative HPLC.
Yield: 38%.
[M+H]$^+$: 573.1.
$^1$H NMR (DMSO-d$_6$): 9.81 (s broad, 1H, NH); 9.74 (s broad, 1H, NH); 9.37 (broad, 1H, NH); 8.07 (t, 1H, J=6.2 Hz, NH); 7.85 (m, 1H, Ar—H); 7.76-7.62 (m, 7H, Ar—H); 7.55-7.42 (m, 3H, Ar—H); 7.28 (s broad, 2H, NH$_2$); 7.28-7.18 (m, 3H, NH$_2$+Ar—H); 4.03 (d, 2H, J=6.0 Hz, CH$_2$); 3.74-3.72 (m broad, 4H, 2CH$_2$); 3.54-3.58 (m broad, 4H, 2CH$_2$).

4-(3-(3-(imino(1,1-dioxidothiomorpholine)methyl) phenyl)ureido)-N-(4-sulfamoylbenzyl)benzenesulfonamide (44)

The title compound was prepared from 4-(3-(3-cyanophenyl)ureido)-N-(4-sulfamoylbenzyl)benzenesulfonamide following procedure C and using 1.5 equivalents of 1,1-dioxothiomorpholine as secondary amine. The product was purified by preparative HPLC.
Yield: 13%.
[M+H]$^+$: 621.1.

4-(3-(3-(imino(4-(pyridin-4-ylmethyl)piperazin-1-yl) methyl)phenyl)ureido)-N-(4-sulfamoylbenzyl)benzenesulfonamide (45)

The title compound was prepared from 4-(3-(3-cyanophenyl)ureido)-N-(4-sulfamoylbenzyl)benzenesulfonamide following procedure C and using 2 equivalents of 1-(pyridin-4-ylmethyl)piperazine as secondary amine. The product was purified by preparative HPLC.
Yield: 11%.
[M+H]$^+$: 663.2.
$^1$H NMR (DMSO-d$_6$): 9.63-9.52 (broad, 3H, 3NH), 9.25 (broad, 1H, NH); 8.67-8.65 (m, 2H, Pyr-H); 8.09 (t, 1H, J=6.1 Hz, NH); 7.88 (m, 1H, Ar—H); 7.77-7.52 (m, 10H, Ar—H+Pyr-H); 7.46-7.41 (m, 2H, Ar—H); 7.30 (broad, 2H, NH$_2$); 7.22-7.18 (m, 1H, Ar—H); 4.04 (d, 2H, J=6.2 Hz, CH$_2$); water signal partially covers a group of signals; 2.80-2.57 (m, 4H, 2CH$_2$).

4-(3-(3-(imino(pyrrolidin-1-yl)methyl)phenyl)ureido)-N-(4-sulfamoylbenzyl)benzenesulfonamide (46)

The title compound was prepared from 4-(3-(3-cyanophenyl)ureido)-N-(4-sulfamoylbenzyl)benzenesulfonamide following procedure C and using 2 equivalents of pyrrolidine as secondary amine. The product was purified by preparative HPLC.
Yield: 16%.
[M+H]$^+$: 557.1.
$^1$H NMR (DMSO-d$_6$): 9.51 (s broad, 1H, NH); 9.42 (s broad, 1H, NH); 9.26 (broad, 1H, NH); 8.75 (s broad, 1H, NH); 8.08 (t, 1H, J=6.4 Hz, NH); 7.90 (m, 1H, Ar—H); 7.76-7.41 (m, 10H, Ar—H); 7.28 (s broad, 2H, NH$_2$); 7.25-7.21 (m, 1H, Ar—H); 4.04 (d, 2H, J=6.3 Hz, CH$_2$); 3.56 (t, 2H, J=6.9 Hz; CH$_2$); 3.41 (t, 2H, J=6.7 Hz; CH$_2$); 2.11-1.84 (m, 4H, 2CH$_2$).

N-(2-(diethylamino)ethyl)-N-methyl-3-(3-(4-(N-(4-sulfamoylbenzyl)sulfamoyl)phenyl)ureido) benzimidamide (47)

The title compound was prepared from 4-(3-(3-cyanophenyl)ureido)-N-(4-sulfamoylbenzyl)benzenesulfonamide following procedure C and using 2 equivalents of N$^1$,N$^1$-diethyl-N$^2$-methylethane-1,2-diamine as secondary amine. The product was purified by preparative HPLC.
Yield: 12%.
[M+H]$^+$: 616.2.
$^1$H NMR (DMSO-d$_6$): 9.87-9.17 (very broad, 4H, 4NH), 8.09 (t, 1H, J=6.3 Hz, NH); 7.96 (m, 1H, Ar—H); 7.77-7.55 (m, 8H, Ar—H); 7.45-7.41 (m, 2H, Ar—H); 7.28 (broad, 2H, NH$_2$); 7.25-7.21 (m, 1H, Ar—H); 4.04 (d, 2H, J=6.3 Hz, CH$_2$); water signal partially covers a group of signals; 1.07 (m broad, 6H, 2CH$_3$).

4-(3-(3-((4-hydroxypiperidin-1-yl)(imino)methyl) phenyl)ureido)-N-(4-sulfamoylbenzyl)benzenesulfonamide (48)

The title compound was prepared from 4-(3-(3-cyanophenyl)ureido)-N-(4-sulfamoylbenzyl)benzenesulfonamide following procedure C and using 1.3 equivalents of 4-hydroxypiperidine as secondary amine. The product was purified by preparative HPLC.

Yield: 42%.

[M+H]$^+$: 587.1.

$^1$H NMR (DMSO-d$_6$): 9.67 (s, 1H, NH); 9.61 (s, 1H, NH); 8.08 (t, 1H, J=6.3 Hz, NH); 7.86 (m, 1H, Ar—H); 7.76-7.51 (m, 8H, Ar—H); 7.45-7.42 (m, 2H, Ar—H); 7.28 (broad, 2H, NH$_2$); 7.21-7.18 (m, 1H, Ar—H); 4.95 (d broad, 1H, J=3.4 Hz, OH); 4.03 (d, 2H, J=6.2 Hz, CH$_2$); 3.90-3.83 (m broad, 1H, CH); water signal partially covers a group of signals; 1.94-1.48 (broad, 4H, 2CH$_2$).

4-(3-(3((3-(dimethylamino)pyrrolidin-1-yl)(imino) methyl)phenyl)ureido)-N-(4-sulfamoylbenzyl)benzenesulfonamide (49)

The title compound was prepared from 4-(3-(3-cyanophenyl)ureido)-N-(4-sulfamoylbenzyl)benzenesulfonamide following procedure C and using 2 equivalents of N,N-dimethylpyrrolidin-3-amine as secondary amine. The product was purified by preparative HPLC.

Yield: 9%.

[M+H]$^+$: 600.2.

$^1$H NMR (DMSO-d$_6$): 9.80-9.55 (broad, 3H, 3NH), 9.04 (broad, 1H, NH); 8.08 (t, 1H, J=6.4 Hz, NH); 7.94 (m, 1H, Ar—H); 7.76-7.51 (m, 8H, Ar—H); 7.45-7.41 (m, 2H, Ar—H); 7.28 (broad, 2H, NH$_2$); 7.25-7.21 (m, 1H, Ar—H); 4.03 (d, 2H, J=6.2 Hz, CH$_2$); 3.84-3.54 (broad, 4H, 2CH$_2$); water signal partially covers a group of signals; 2.84-2.70 (broad, 6H, 2CH$_3$); 2.37-2.01 (broad, 2H, CH$_2$).

4-(3-(3-(imino(2-(pyrrolidin-1-ylmethyl)pyrrolidin-1-yl)methyl)phenyl)ureido)-N-(4-sulfamoylbenzyl) benzenesulfonamide (50)

The title compound was prepared from 4-(3-(3-cyanophenyl)ureido)-N-(4-sulfamoylbenzyl)benzenesulfonamide following procedure C and using 2 equivalents of 1-(pyrrolidin-2-ylmethyl)pyrrolidine as secondary amine. The product was purified by preparative HPLC.

Yield: 12%

[M+H]$^+$: 640.2.

tert-butyl 4-(imino(3-(3-(4-(N-(4-sulfamoylbenzyl) sulfamoyl)phenyl)ureido)phenyl)methyl)piperazine-1-carboxylate (51)

The title compound was prepared from 4-(3-(3-cyanophenyl)ureido)-N-(4-sulfamoylbenzyl)benzenesulfonamide following procedure C and using 2 equivalents of tert-butyl piperazine-1-carboxylate as secondary amine. The product was purified by preparative HPLC.

Yield: 15%.

[M+H]$^+$: 672.2.

$^1$H NMR (DMSO-d$_6$): 9.58 (s broad, 1H, NH); 9.52 (s broad, 1H, NH); 9.45 (broad, 1H, NH); 9.22 (s broad, 1H, NH); 8.08 (t, 1H, J=6.4 Hz, NH); 7.89 (m, 1H, Ar—H); 7.76-7.41 (m, 10H, Ar—H); 7.28 (s broad, 2H, NH$_2$); 7.23-7.20 (m, 1H, Ar—H); 4.03 (d, 2H, J=6.3 Hz, CH$_2$); 3.74 (m broad, 2H, CH$_2$); 3.63 (m broad, 2H, CH$_2$); water signal partially covers a group of signals; 1.42 (s, 9H, 3CH$_3$).

4-(3-(3-(imino(piperazin-1-yl)methyl)phenyl)ureido)-N-(4-sulfamoylbenzyl)benzenesulfonamide (52)

The title compound was obtained after removal of the tert-butyl-carboxylate group from compound 51. 60 mg of N-protected compound were dissolved in 5 ml of tetrahydrofurane and 5 ml of 4 M HCl in dioxane were slowly added under stifling at 0° C. After 2 hours stifling at rt, the solvent was removed. The product was purified by preparative HPLC.

Yield: 85%.

[M+H]$^+$: 572.1.

$^1$H NMR (DMSO-d$_6$): 9.83-9.41 (very broad, 4H, 4NH); 8.09 (t, 1H, J=6.4 Hz, NH); 7.93 (broad, 1H, Ar—H); 7.76-7.53 (m, 8H, Ar—H); 7.45-7.41 (m, 2H, Ar—H); 7.29 (s broad, 2H, NH$_2$); 7.27-7.23 (m, 1H, Ar—H); 4.04 (d, 2H, J=6.3 Hz, CH$_2$); 3.95 (m broad, 2H, CH$_2$); 3.58 (m broad, 2H, CH$_2$); water signal partially covers a group of signals.

4-(3-(3-(imino(4-methylpiperazin-1-yl)methyl)phenyl)ureido)-N-(4-sulfamoylbenzyl)benzenesulfonamide (53)

The title compound was prepared from 4-(3-(3-cyanophenyl)ureido)-N-(4-sulfamoylbenzyl)benzenesulfonamide following procedure C and using 2 equivalents of N-methylpiperazine as secondary amine. The product was purified by preparative HPLC.

Yield: 12%.

[M+H]$^+$: 586.1.

$^1$H NMR (DMSO-d$_6$): 9.79 (s broad, 1H, NH); 9.66 (s broad, 1H, NH); 9.61 (broad, 1H, NH); 9.44 (s broad, 1H, NH); 8.09 (t, 1H, J=6.3 Hz, NH); 7.93 (m, 1H, Ar—H); 7.76-7.54 (m, 8H, Ar—H); 7.45-7.41 (m, 2H, Ar—H); 7.29 (s broad, 2H, NH$_2$); 7.24-7.21 (m, 1H, Ar—H); 4.04 (d, 2H, J=6.2 Hz, CH$_2$); water signal partially covers a group of signals.

4-(3-(3-(imino(4-isopropylpiperazin-1-yl)methyl) phenyl)ureido)-N-(4-sulfamoylbenzyl)benzenesulfonamide (54)

The title compound was prepared from 4-(3-(3-cyanophenyl)ureido)-N-(4-sulfamoylbenzyl)benzenesulfonamide following procedure C and using 1.5 equivalents of 1-isopropylpiperazine as secondary amine. The product was purified by preparative HPLC.

Yield: 3%.

[M+H]$^+$: 614.2.

4-(3-(3-(imino(4-pentylpiperazin-1-yl)methyl)phenyl)ureido)-N-(4-sulfamoylbenzyl)benzenesulfonamide (55)

The title compound was prepared from 4-(3-(3-cyanophenyl)ureido)-N-(4-sulfamoylbenzyl)benzenesulfonamide following procedure C and using 2 equivalents of n-pentylpiperazine as secondary amine. The product was purified by preparative HPLC.

Yield: 13%.

[M+H]$^+$: 642.1.

$^1$H NMR (DMSO-d$_6$): 9.75 (very broad, 1H, NH); 9.54 (broad, 1H, NH); 9.50 (broad, 1H, NH); 9.40 (very broad, 1H, NH); 8.08 (t, 1H, J=6.3 Hz, NH); 7.92 (broad, 1H, Ar—H); 7.76-7.53 (m, 8H, Ar—H); 7.44-7.40 (m, 2H, Ar—H); 7.27 (broad, 2H, NH$_2$); 7.25-7.20 (m, 1H, Ar—H); 4.03 (d, 2H, J=6.3 Hz, CH$_2$); water signal partially covers a group of signals; 1.65-1.53 (broad, 2H, CH$_2$); 1.35-1.24 (m, 4H, 2CH$_2$); 0.88 (t, 3H, J=6.8 Hz, CH$_3$).

4-(3-(3-((4-heptylpiperazin-1-yl)(imino)methyl)phenyl)ureido)-N-(4-sulfamoylbenzyl)benzenesulfonamide (56)

The title compound was prepared from 4-(3-(3-cyanophenyl)ureido)-N-(4-sulfamoylbenzyl)benzenesulfonamide following procedure C and using 1.5 equivalents of n-heptylpiperazine as secondary amine. The product was purified by preparative HPLC.
Yield: 10%.
[M+H]$^+$: 670.1.

4-(3-(3((4-acetylpiperazin-1-yl)(imino)methyl)phenyl)ureido)-N-(4-sulfamoylbenzyl)benzenesulfonamide (57)

The title compound was prepared from 4-(3-(3-cyanophenyl)ureido)-N-(4-sulfamoylbenzyl)benzenesulfonamide following procedure C and using 1 equivalent of 1-(piperazin-1-yl)ethanone as secondary amine. The product was purified by preparative HPLC.
Yield: 14%.
[M+H]$^+$: 614.1.

4-(3-(3-(imino(4-propionylpiperazin-1-yl)methyl)phenyl)ureido)-N-(4-sulfamoylbenzyl)benzenesulfonamide (58)

The title compound was prepared from 4-(3-(3-cyanophenyl)ureido)-N-(4-sulfamoylbenzyl)benzenesulfonamide following procedure C and using 1 equivalent of 1-(piperazin-1-yl)propan-1-one as secondary amine. The product was purified by preparative HPLC.
Yield: 16%.
[M+H]$^+$: 628.0.
$^1$H NMR (DMSO-d$_6$): 10.52 (very broad, 2H, 2NH); 9.38 (broad, 1H, NH); 8.05 (t broad, 1H, NH); 7.85 (broad, 1H, Ar—H); 7.76-7.66 (m, 7H, Ar—H); 7.54-7.41 (m, 3H, Ar—H); 7.29 (broad, 2H, NH$_2$); 7.19-7.14 (m, 1H, Ar—H); 4.03 (d broad, 2H, CH$_2$); 3.67-3.50 (broad, 8H, 4H$_2$); 2.35 (q, 2H, J=7.4 Hz, CH$_2$); 1.00 (t, 3H, J=7.4 Hz, CH$_3$).

4-(3-(3-(imino(4-pentanoylpiperazin-1-yl)methyl)phenyl)ureido)-N-(4-sulfamoylbenzyl)benzenesulfonamide (59)

The title compound was prepared from 4-(3-(3-cyanophenyl)ureido)-N-(4-sulfamoylbenzyl)benzenesulfonamide following procedure C and using 1 equivalent of 1-(piperazin-1-yl)pentan-1-one as secondary amine. The product was purified by preparative HPLC.
Yield: 9%.
[M+H]$^+$: 656.0.
$^1$H NMR (DMSO-d$_6$): 10.05-9.32 (very broad, 4H, 4NH); 8.07 (t, 1H, J=6.3 Hz, NH); 7.85 (broad, 1H, Ar—H); 7.76-7.62 (m, 7H, Ar—H); 7.57-7.51 (m, 1H, Ar—H); 7.46-7.40 (m, 2H, Ar—H); 7.29 (broad, 2H, NH$_2$); 7.23-7.19 (m, 1H, Ar—H); 4.03 (d, 2H, J=5.9 Hz, CH$_2$); 3.69-3.52 (broad, 8H, 4H$_2$); 2.33 (t, 2H, J=7.4 Hz, CH$_2$); 1.49 (m, 2H, 7.4 Hz, CH$_2$); 1.30 (m, 2H, 7.4 Hz, CH$_2$); 0.88 (t, 3H, J=7.4 Hz, CH$_3$).

methyl 4-(imino(3-(3-(4-(N-(4-sulfamoylbenzyl)sulfamoyl)phenyl)ureido) phenyl)methyl)piperazine-1-carboxylate (60)

The title compound was prepared from 4-(3-(3-cyanophenyl)ureido)-N-(4-sulfamoylbenzyl)benzenesulfonamide following procedure C and using 1 equivalent of methyl piperazine-1-carboxylate as secondary amine. The product was purified by preparative HPLC.
Yield: 13%.
[M+H]$^+$: 630.1.
$^1$H NMR (DMSO-d$_6$): 10.87 (s broad, 1H, NH); 10.81 (s broad, 1H, NH); 8.05 (t broad, 1H, NH); 7.85 (m broad, 1H, Ar—H); 7.77-7.69 (m, 7H, Ar—H); 7.53-7.42 (m, 3H, Ar—H); 7.30 (broad, 2H, NH$_2$); 7.17-7.13 (m, 1H, Ar—H); 4.03 (d broad, 2H, CH$_2$); 3.63 (s, 3H, CH$_3$); water signal covers a group of signals.

ethyl 4-(imino(3-(3-(4-(N-(4-sulfamoylbenzyl)sulfamoyl)phenyl)ureido)phenyl)methyl)piperazine-1-carboxylate (61)

The title compound was prepared from 4-(3-(3-cyanophenyl)ureido)-N-(4-sulfamoylbenzyl)benzenesulfonamide following procedure C and using 2 equivalent of ethyl piperazine-1-carboxylate as secondary amine. The product was purified by preparative HPLC.
Yield: 8%.
[M+H]$^+$: 644.1.
$^1$H NMR (DMSO-d$_6$): 9.61-9.21 (very broad, 4H, 4NH); 8.08 (t, 1H, NH); 7.89-7.87 (m, 1H, Ar—H); 7.77-7.52 (m, 8H, Ar—H); 7.45-7.41 (m, 2H, Ar—H); 7.28 ((broad, 2H, NH$_2$); 7.24-7.20 (m, 1H, Ar—H); 4.12-4.02 (m, 4H, CH$_2$+ OCH$_2$); 3.82-3.40 (broad, 8H, 4CH$_2$); 1.20 (t, 3H, J=7.1 Hz, CH$_3$).

propyl 4-(imino(3-(3-(4-(N-(4-sulfamoylbenzyl)sulfamoyl)phenyl)ureido)phenyl)methyl)piperazine-1-carboxylate (62)

The title compound was prepared from 4-(3-(3-cyanophenyl)ureido)-N-(4-sulfamoylbenzyl)benzenesulfonamide following procedure C and using 1 equivalent of propyl piperazine-1-carboxylate. The product was purified by preparative HPLC.
Yield (5%)
[M+H]$^+$: 658.1.
$^1$H NMR (DMSO-d$_6$): 11.06-10.71 (s broad, 2H, 2NH); 8.03 (t, 1H, J=6.1 Hz, NH); 7.85-7.81 (m broad, 1H, Ar—H); 7.77-7.66 (m, 7H, Ar—H); 7.51-7.41 (m, 3H, Ar—H); 7.29 (broad, 2H, NH$_2$); 7.14-7.10 (m, 1H, Ar—H); 4.03 (d, 2H, J=6.0 Hz, CH$_2$); 3.98 (t, 2H, J=6.6 Hz, OCH$_2$); water signal covers a group of signals; 1.59 (m, 2H, CH$_2$); 0.89 (t, 3H, J=7.4 Hz, CH$_3$).

4-(3-(3-((4-butyl-3-oxopiperazin-1-yl)(imino)methyl)phenyl)ureido)-N-(4-sulfamoylbenzyl)benzenesulfonamide (63)

The title compound was prepared from 4-(3-(3-cyanophenyl)ureido)-N-(4-sulfamoylbenzyl)benzenesulfonamide following procedure C and using 2.2 equivalent of 1-butylpiperazin-2-one as secondary amine. The product was purified by preparative HPLC.
Yield: 35%.
[M+H]$^+$: 642.1.
$^1$H NMR (DMSO-d$_6$): 10.59 (very broad, 2H, 2NH); 8.06 (t broad, 1H, NH); 7.85-7.82 (m broad, 1H, Ar—H); 7.77-7.66 (m, 7H, Ar—H); 7.54-7.41 (m, 3H, Ar—H); 7.29 (s broad, 2H, NH$_2$); 7.18-7.13 (m, 1H, Ar—H); 4.16 (broad, 1H, CO—CH$_2$—N); 4.03 (d broad, 2H, CH$_2$); 3.68-3.44 (broad, 4H, 2CH$_2$); 3.35 (t, 2H; J=7.2 Hz, CH$_2$); water signal covers a group of signals; 1.54-1.21 (m, 4H, 2CH$_2$); 0.90 (t, 3H; J=7.3 Hz, CH$_3$).

N,N-dimethyl-3-(3-(4-(N-(4-sulfamoylbenzyl)sulfamoyl)phenyl)ureido)benzimidamide (64)

The title compound was prepared from 4-(3-(3-cyanophenyl)ureido)-N-(4-sulfamoylbenzyl)benzenesulfonamide following procedure C and using 2.2 equivalent of N,N-dimethylamine as secondary amine. The product was purified by preparative HPLC.

Yield: 54%.

[M+H]$^+$: 531.1.

$^1$H NMR (DMSO-d$_6$): 10.90 (s broad, 1H, 1NH); 10.85 (s broad, 1H, 1NH); 10.85 (s broad, 1H, 1NH); 9.14 (broad, 1H, NH); 8.05 (t broad, 1H, NH); 7.83 (m broad, 1H, Ar—H); 7.76-7.68 (m, 7H, Ar—H); 7.54-7.41 (m, 3H, Ar—H); 7.30 (s broad, 2H, NH$_2$); 7.16-7.11 (m, 1H, Ar—H); 4.03 (broad, 2H, CH$_2$); 3.11 (s broad, 6H, 2CH$_3$).

4-(3-(3(4-(2-cyanoethyl)piperazin-1-yl)(imino) methyl)phenyl)ureido)-N-(4-sulfamoylbenzyl)benzenesulfonamide (65)

The title compound was prepared from 4-(3-(3-cyanophenyl)ureido)-N-(4-sulfamoylbenzyl)benzenesulfonamide following procedure C and using 2.2 equivalent of 3-piperazinopropionitrile as secondary amine. The product was purified by preparative HPLC.

Yield: 57%.

[M+H]$^+$: 625.1.

4-(3-(3-((4-(cyclopropylmethyl)piperazin-1-yl) (imino)methyl)phenyl)ureido)-N-(4-sulfamoylbenzyl)benzenesulfonamide (66)

The title compound was prepared from 4-(3-(3-cyanophenyl)ureido)-N-(4-sulfamoylbenzyl)benzenesulfonamide following procedure C and using 2.2 equivalent of 1-(cyclopropylmethyl)piperazine as secondary amine. The product was purified by preparative HPLC.

Yield: 57%.

[M+H]$^+$: 625.1.

$^1$H NMR (DMSO-d$_6$): 11.52 (s, 1H, 1NH); 11.50 (s broad, 1H, 1NH); 8.03 (t broad, 1H, NH); 7.86 (m broad, 1H, Ar—H); 7.79-7.67 (m, 7H, Ar—H); 7.52-7.41 (m, 3H, Ar—H); 7.30 (s broad, 2H, NH$_2$); 7.14-7.09 (m, 1H, Ar—H); 4.03 (broad, 2H, CH$_2$); 3.57 (broad, 4H, 2CH$_2$); 2.60 (broad, 4H, 2CH$_2$); 2.26 (d, 2H, J=6.6 Hz, CH$_2$); 0.84 (m, 1H, CH); 0.47 (m, 2H, CH$_2$); 0.09 (m, 2H, CH$_2$).

4-(3-(3((4-((1,3-dioxolan-2-yl)methyl)piperazin-1-yl)(imino)methyl)phenyl)ureido)-N-(4-sulfamoylbenzyl)benzenesulfonamide (67)

The title compound was prepared from 4-(3-(3-cyanophenyl)ureido)-N-(4-sulfamoylbenzyl)benzenesulfonamide following procedure C and using 2.2 equivalent of 1-(1,3-dioxolan-2-ylmethyl)piperazine as secondary amine. The product was purified by preparative HPLC.

Yield: 43%.

[M+H]$^+$: 658.1.

$^1$H NMR (DMSO-d$_6$): 11.53 (s, 1H, 1NH); 11.49 (s broad, 1H, 1NH); 8.02 (t broad, 1H, NH); 7.83 (m broad, 1H, Ar—H); 7.78-7.67 (m, 7H, Ar—H); 7.50-7.40 (m, 3H, Ar—H); 7.30 (s broad, 2H, NH$_2$); 7.11-7.06 (m, 1H, Ar—H); 4.93 (t, 1H, J=4.4 Hz, CH); 4.02 (broad, 2H, CH$_2$); 3.90-3.74 (m, 4H, 2CH$_2$); 3.51 (broad, 4H, 2CH$_2$); 2.65 (broad, 4H, 2CH$_2$); 2.57 (d, 2H, J=4.4 Hz, CH$_2$).

4-(3-(3-(imino(4-((tetrahydrofuran-2-yl)methyl)piperazin-1-yl)methyl)phenyl)ureido)-N-(4-sulfamoylbenzyl)benzenesulfonamide (68)

The title compound was prepared from 4-(3-(3-cyanophenyl)ureido)-N-(4-sulfamoylbenzyl)benzenesulfonamide following procedure C and using 2.2 equivalent of 1-(tetrahydro-2-furylmethyl)piperazine as secondary amine. The product was purified by preparative HPLC.

Yield: 48%.

[M+H]$^+$: 656.1.

$^1$H NMR (DMSO-d$_6$): 11.38 (s, 1H, 1NH); 11.35 (s broad, 1H, 1NH); 8.03 (t broad, 1H, NH); 7.85 (m broad, 1H, Ar—H); 7.77-7.67 (m, 7H, Ar—H); 7.52-7.41 (m, 3H, Ar—H); 7.30 (s broad, 2H, NH$_2$); 7.13-7.09 (m, 1H, Ar—H); 4.02 (broad, 2H, CH$_2$); 3.98-3.90 (m, 1H, CH); 3.77-3.50 (group of signals, 6H, OCH$_2$+2pipCH$_2$); DMSO signal covers a group of signals; 1.98-1.41 (group of multiplets, 4H, 2CH$_2$).

4-(3-(3-(imino(4-(2-methoxyethyl)piperazin-1-yl) methyl)phenyl)ureido)-N-(4-sulfamoylbenzyl)benzenesulfonamide (69)

The title compound was prepared from 4-(3-(3-cyanophenyl)ureido)-N-(4-sulfamoylbenzyl)benzenesulfonamide following procedure C and using 2.2 equivalent of 1-(2-methoxyethyl)piperazine as secondary amine. The product was purified by preparative HPLC.

Yield: 41.5%.

[M+H]$^+$: 630.1.

$^1$H NMR (DMSO-d$_6$): 11.43 (s, 1H, 1NH); 11.40 (s broad, 1H, 1NH); 8.03 (t broad, 1H, NH); 7.85 (m broad, 1H, Ar—H); 7.78-7.67 (m, 7H, Ar—H); 7.52-7.41 (m, 3H, Ar—H); 7.30 (s broad, 2H, NH$_2$); 7.13-7.09 (m, 1H, Ar—H); 4.03 (broad, 2H, CH$_2$); 3.55 (broad, 4H, 2CH$_2$); 3.45 (t, 2H; J=5.6 Hz, OCH$_2$); 3.23 (s, 3H, CH$_3$); 2.62-2.53 (broad+q, 6H, 3CH$_2$).

5-((4-(3-(3-((4-butylpiperazin-1-yl)(imino)methyl) phenyl)ureido)phenylsulfonamido)methyl) thiophene-2-sulfonamide (70)

The title compound was prepared from 5-((4-(3-(3-cyanophenyl)ureido) phenylsulfonamido)methyl)thiophene-2-sulfonamide following procedure C and using 2.2 equivalent of n-butylpiperazine as secondary amine. The product was purified by preparative HPLC.

Yield: 58%.

[M+H]$^+$: 634.1.

$^1$H NMR (DMSO-d$_6$): 11.22 (s, 1H, 1NH); 11.17 (s broad, 1H, 1NH); 8.23 (broad, 1H, NH); 7.84 (m broad, 1H, Ar—H); 7.76-7.47 (m, 8H, NH$_2$+6 Ar—H); 7.33 (d, 1H, J=3.7 Hz, CH); 7.14-7.10 (m, 1H, Ar—H); 6.91 (d, 1H, J=3.7 Hz, CH); 4.17 (broad, 2H, CH$_2$); 3.55 (broad, 4H, 2CH$_2$); DMSO signal covers a group of signals; 2.34 (t, 2H, J=7.2 Hz, CH$_2$); 1.46-1.23 (m, 4H, 2CH$_2$); 0.88 (t, 3H, J=7.2 Hz, CH$_3$).

4-(3-(4-((4-butylpiperazin-1-yl)(imino)methyl)phenyl)ureido)-N-(4-sulfamoylbenzyl)benzenesulfonamide (71)

The title compound was prepared from 4-(3-(4-cyanophenyl)ureido)-N-(4-sulfamoylbenzyl)benzenesulfonamide following procedure C and using 3 equivalents of n-butylpiperazine as secondary amine. The product was purified by preparative HPLC.

Yield: 2.4%.

[M+H]$^+$: 628.1.

methyl 4-((acetylimino)(3-(3-(4-(N-(4-sulfamoylbenzyl)sulfamoyl)phenyl)ureido)phenyl)methyl) piperazine-1-carboxylate (72)

100 mg of compound 60 were dissolved in 2 ml of DCM/DMF 1:1 solution, containing 2 eq of DIEA. Under stirring and at 0° C., 6 eq of acetylchloride were added portionwise during 30 minutes. The solution was stirred overnight at rt, then water was added and a precipitate formed. The precipitate was separated and the title compound was obtained after preparative HPLC purification.

Yield: 19%.

[M+H]$^+$: 672.2.

methyl 4-((octanoylimino)(3-(3-(4-(N-(4-sulfamoyl-benzyl)sulfamoyl)phenyl)ureido)phenyl)methyl) piperazine-1-carboxylate (73)

The title compound was obtained as described for compound 72 and using 4 eq of octanoylchloride. The product was purified by preparative HPLC.

Yield: 1%.

[M+H]$^+$: 756.3.

methyl 4-((hydroxyimino)(3-(3-(4-(N-(4-sulfamoyl-benzyl)sulfamoyl)phenyl)ureido)phenyl)methyl) piperazine-1-carboxylate (74)

The title compound was obtained following procedure D, starting from 3-nitrobenzaldehyde and using 1 eq of 4-(aminomethyl)benzenesulfonamide as final amino reagent. The product was purified by preparative HPLC Yield: 1% (overall over 6 steps)

[M+H]$^+$: 646.2.

TABLE 1

Exemplary compounds of formula (I) of the present invention include, but not limited to the followings:

| No. | Structure | Name | LC/MS [M + H]+ |
|---|---|---|---|
| 1 | 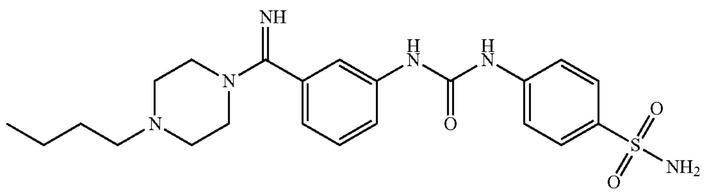 [SMILES: CCCCN1CCN(C(=N)c2cccc(NC(=O)Nc3ccc(S(N)(=O)=O)cc3)c2)CC1] | 4-(3-((4-butylpiperazin-1-yl)(imino)methyl)phenyl)ureido)benzenesulfonamide | 459.1 |
| 2 | 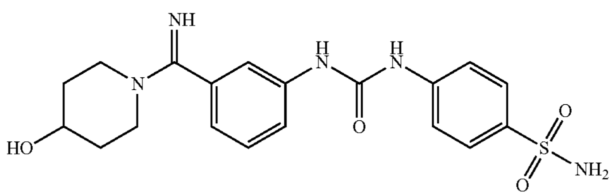 [SMILES: N=C(c1cccc(NC(=O)Nc2ccc(S(N)(=O)=O)cc2)c1)N1CCC(O)CC1] | 4-(3-((4-hydroxypiperidin-1-yl)(imino)methyl)phenyl)ureido)benzenesulfonamide | 418.0 |
| 3 | 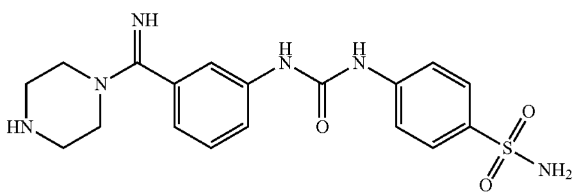 [SMILES: N=C(c1cccc(NC(=O)Nc2ccc(S(N)(=O)=O)cc2)c1)N1CCNCC1] | 4-(3-(imino(piperazin-1-yl)methyl)phenyl)ureido)benzenesulfonamide | 403.0 |
| 4 | 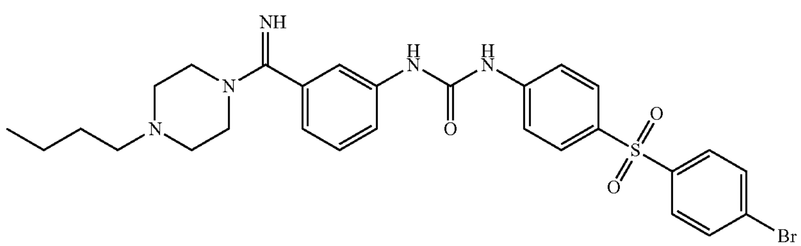 [SMILES: CCCCN1CCN(C(=N)c2cccc(NC(=O)Nc3ccc(S(=O)(=O)c4ccc(Br)cc4)cc3)c2)CC1] | 1-(4-(4-bromophenylsulfonyl)phenyl)-3-(3-((4-butylpiperazin-1-yl)(imino)methyl)phenyl)urea | 599.1 |

TABLE 1-continued

Exemplary compounds of formula (I) of the present invention include, but not limited to the followings:

| No. | Structure | Name | LC/MS [M + H]⁺ |
|---|---|---|---|
| 5 | 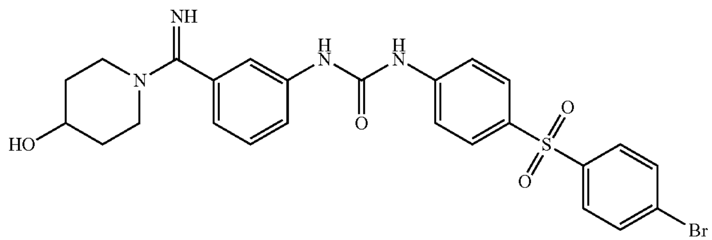 [SMILES: N=C(c1cccc(NC(=O)Nc2ccc(S(=O)(=O)c3ccc(Br)cc3)cc2)c1)N1CCC(O)CC1] | 1-(4-(4-bromophenylsulfonyl)phenyl)-3-(3-((4-hydroxypiperidin-1-yl)(imino)methyl)phenyl)urea | 557.0 |
| 6 | 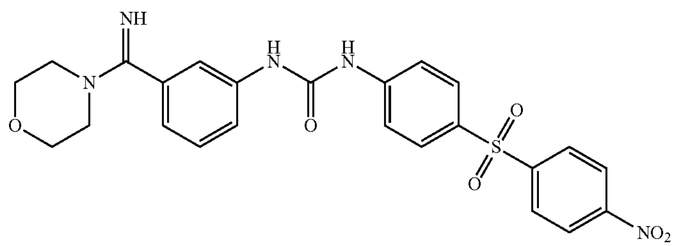 [SMILES: N=C(c1cccc(NC(=O)Nc2ccc(S(=O)(=O)c3ccc([N+](=O)[O-])cc3)cc2)c1)N1CCOCC1] | 1-(3-(imino(morpholino)methyl)phenyl)-3-(4-(4-nitrophenylsulfonyl)phenyl)urea | 510.1 |
| 7 | 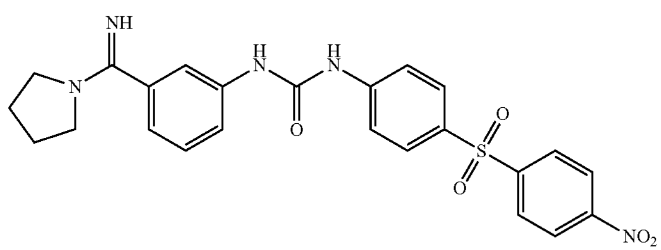 [SMILES: N=C(c1cccc(NC(=O)Nc2ccc(S(=O)(=O)c3ccc([N+](=O)[O-])cc3)cc2)c1)N1CCCC1] | 1-(3-(imino(pyrrolidin-1-yl)methyl)phenyl)-3-(4-(4-nitrophenylsulfonyl)phenyl)urea | 494.0 |

TABLE 1-continued

Exemplary compounds of formula (I) of the present invention include, but not limited to the followings:

| No. | Structure | Name | LC/MS [M + H]⁺ |
|---|---|---|---|
| 8 | 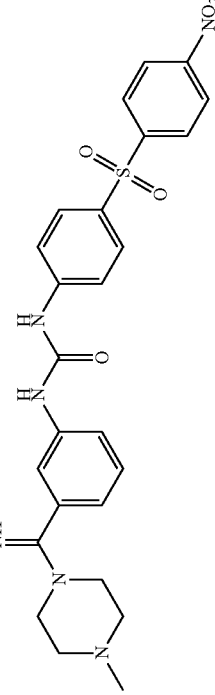 | 1-(3-(imino(4-methyl)piperazin-1-yl)methyl)phenyl)-3-(4-(4-nitrophenylsulfonyl)phenyl)urea | 523.1 |
| 9 | 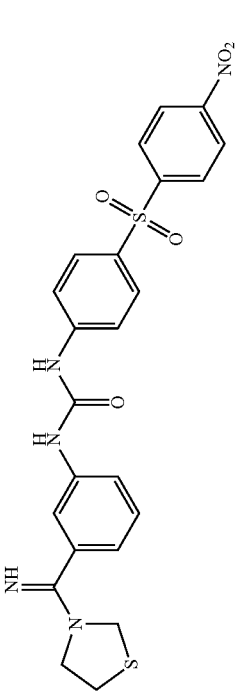 | 1-(3-(imino(thiazolidin-3-yl)methyl)phenyl)-3-(4-(4-nitrophenylsulfonyl)phenyl)urea | 512.1 |
| 10 | 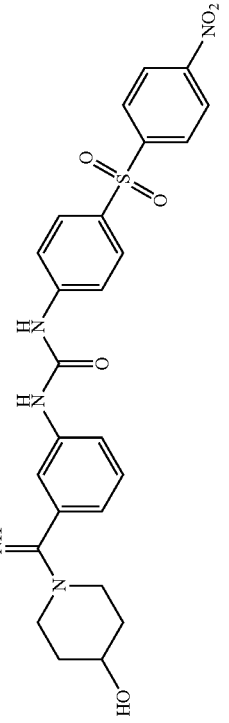 | 1-(3-((4-hydroxypiperidin-1-yl)(imino)methyl)phenyl)-3-(4-(4-nitrophenylsulfonyl)phenyl)urea | 524.1 |

TABLE 1-continued

Exemplary compounds of formula (I) of the present invention include, but not limited to the followings:

| No. | Structure | Name | LC/MS [M + H]+ |
|---|---|---|---|
| 11 | 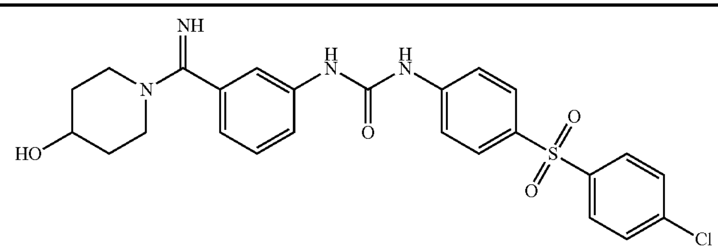 | 1-(4-(4-chlorophenylsulfonyl)phenyl)-3-(3-((4-hydroxypiperidin-1-yl)(imino)methyl)phenyl)urea | 513.0 |
| 12 | 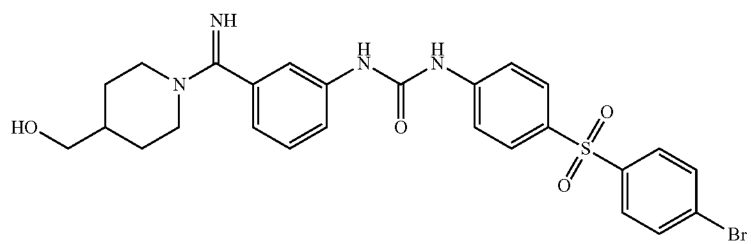 [SMILES: N=C(c1cccc(NC(=O)Nc2ccc(S(=O)(=O)c3ccc(Br)cc3)cc2)c1)N1CCC(CO)CC1] | 1-(4-(4-bromophenylsulfonyl)phenyl)-3-(3-((4-(hydroxymethyl)piperidin-1-yl)(imino)methyl)phenyl)urea | 570.9 |
| 13 | 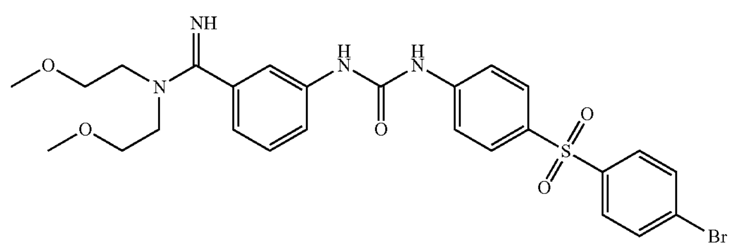 [SMILES: COCCN(CCOC)C(=N)c1cccc(NC(=O)Nc2ccc(S(=O)(=O)c3ccc(Br)cc3)cc2)c1] | 3-(3-(4-(4-bromophenylsulfonyl)phenyl)ureido)-N,N-bis(2-methoxyethyl)benzimidamide | 589.1 |
| 14 | 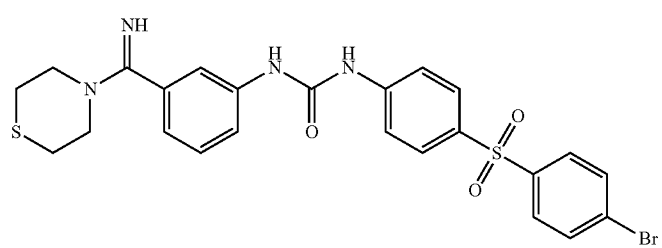 [SMILES: N=C(c1cccc(NC(=O)Nc2ccc(S(=O)(=O)c3ccc(Br)cc3)cc2)c1)N1CCSCC1] | 1-(4-(4-bromophenylsulfonyl)phenyl)-3-(3-(imino(thiomorpholino)methyl)phenyl)urea | 559.0 |

TABLE 1-continued

Exemplary compounds of formula (I) of the present invention include, but not limited to the followings:

| No. | Structure | Name | LC/MS [M+H]+ |
|---|---|---|---|
| 15 | 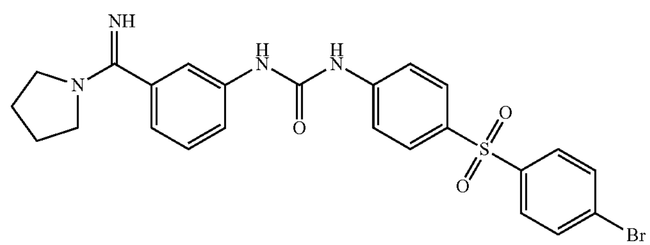 [SMILES: N=C(c1cccc(NC(=O)Nc2ccc(S(=O)(=O)c3ccc(Br)cc3)cc2)c1)N1CCCC1] | 1-(4-(4-bromophenylsulfonyl)phenyl)-3-(3-imino(pyrrolidin-1-yl)methyl)phenyl)urea | 527.0 |
| 16 | 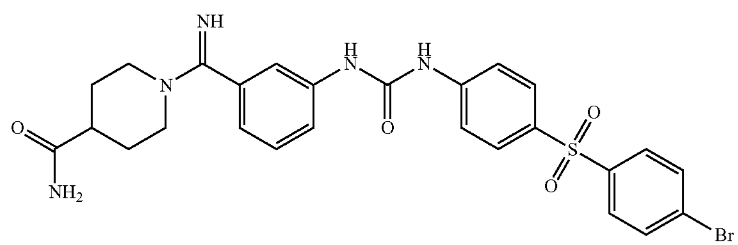 [SMILES: N=C(c1cccc(NC(=O)Nc2ccc(S(=O)(=O)c3ccc(Br)cc3)cc2)c1)N1CCC(C(N)=O)CC1] | 1-((3-(4-(4-bromophenylsulfonyl)phenyl)ureido)phenyl)(imino)methyl)piperidine-4-carboxamide | 584.0 |
| 17 | 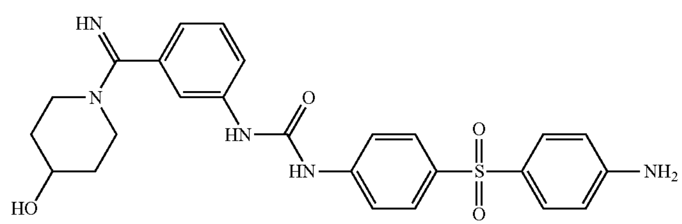 [SMILES: N=C(c1cccc(NC(=O)Nc2ccc(S(=O)(=O)c3ccc(N)cc3)cc2)c1)N1CCC(O)CC1] | 1-(4-(4-aminophenylsulfonyl)phenyl)-3-(3-((4-hydroxypiperidin-1-yl)(imino)methyl)phenyl)urea | 494.1 |
| 18 | 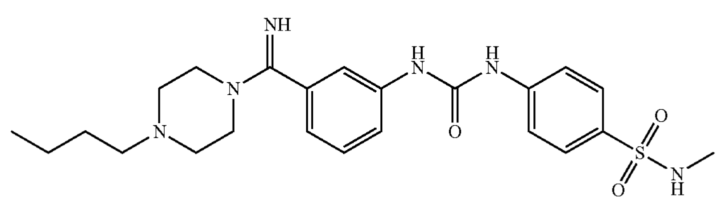 [SMILES: CCCCN1CCN(C(=N)c2cccc(NC(=O)Nc3ccc(S(=O)(=O)NC)cc3)c2)CC1] | 4-(3-(3-((4-butylpiperazin-1-yl)(imino)methyl)phenyl)ureido)-N-methylbenzenesulfonamide | 473.2 |

TABLE 1-continued

Exemplary compounds of formula (I) of the present invention include, but not limited to the followings:

| No. | Structure | Name | LC/MS [M + H]⁺ |
|---|---|---|---|
| 19 | 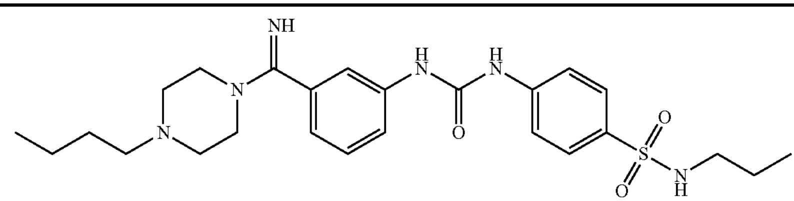 | 4-(3-(3-((4-butylpiperazin-1-yl)(imino)methyl)phenyl)ureido)-N-propylbenzenesulfonamide | 501.3 |
| 20 | 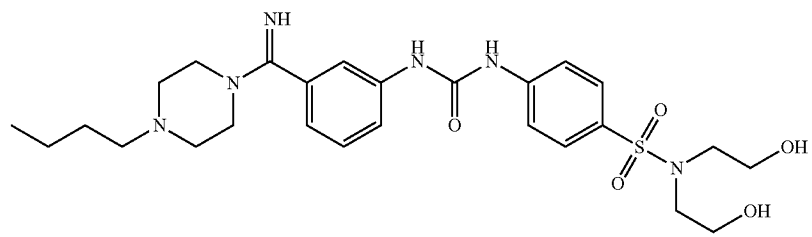 [SMILES: CCCCN1CCN(C(=N)c2cccc(NC(=O)Nc3ccc(S(=O)(=O)N(CCO)CCO)cc3)c2)CC1] | 4-(3-(3-((4-butylpiperazin-1-yl)(imino)methyl)phenyl)ureido)-N,N-bis(2-hydroxyethyl)benzenesulfonamide | 547.2 |
| 21 | 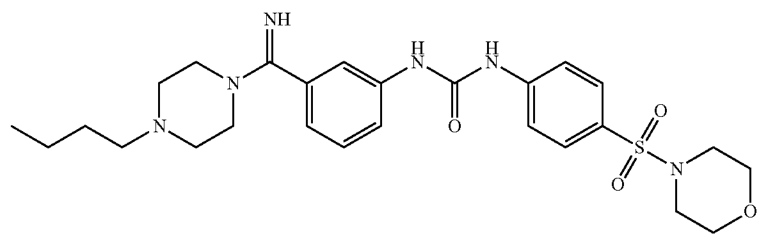 [SMILES: CCCCN1CCN(C(=N)c2cccc(NC(=O)Nc3ccc(S(=O)(=O)N4CCOCC4)cc3)c2)CC1] | 1-(3-((4-butylpiperazin-1-yl)(imino)methyl)phenyl)-3-(4-(morpholinosulfonyl)phenyl)urea | 529.2 |
| 22 | 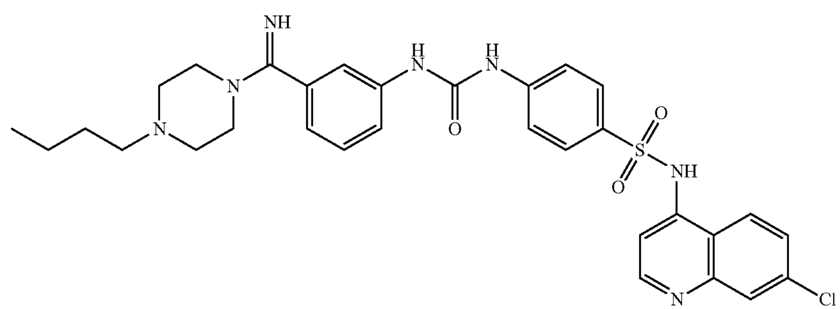 [SMILES: CCCCN1CCN(C(=N)c2cccc(NC(=O)Nc3ccc(S(=O)(=O)Nc4ccnc5cc(Cl)ccc45)cc3)c2)CC1] | 4-(3-(3-((4-butylpiperazin-1-yl)(imino)methyl)phenyl)ureido)-N-(7-chloroquinolin-4-yl)benzenesulfonamide | 620.2 |

TABLE 1-continued

Exemplary compounds of formula (I) of the present invention include, but not limited to the followings:

| No. | Structure | Name | LC/MS [M + H]+ |
|---|---|---|---|
| 23 | 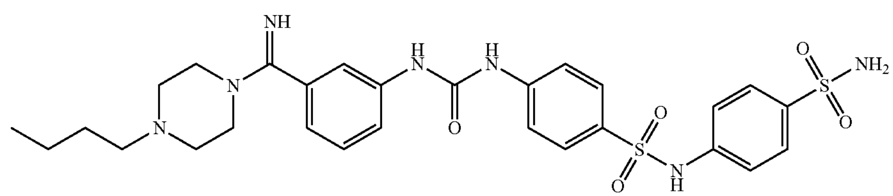 [SMILES: CCCCN1CCN(C(=N)c2cccc(NC(=O)Nc3ccc(S(=O)(=O)Nc4ccc(S(N)(=O)=O)cc4)cc3)c2)CC1] | 4-(3-(4-butylpiperazin-1-yl)(imino)methyl)phenyl)ureido)-N-(4-sulfamoylphenyl)benzenesulfonamide | 614.2 |
| 24 | 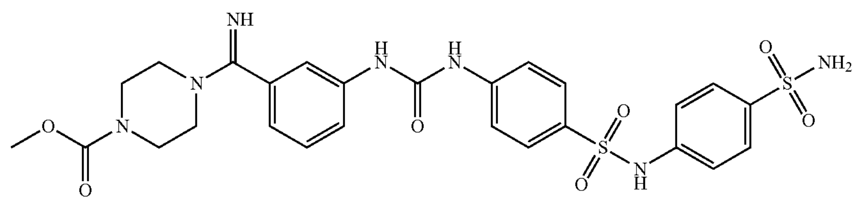 [SMILES: COC(=O)N1CCN(C(=N)c2cccc(NC(=O)Nc3ccc(S(=O)(=O)Nc4ccc(S(N)(=O)=O)cc4)cc3)c2)CC1] | methyl 4-(imino(3-(4-(N-(4-sulfamoylphenyl)sulfamoyl)phenyl)ureido)phenyl)methyl)piperazin-1-carboxylate | 616.0 |
| 25 | 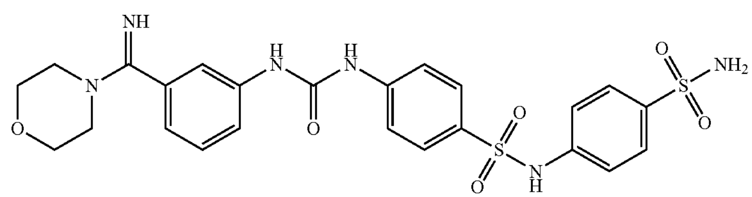 [SMILES: N=C(c1cccc(NC(=O)Nc2ccc(S(=O)(=O)Nc3ccc(S(N)(=O)=O)cc3)cc2)c1)N1CCOCC1] | 4-(3-(imino(morpholino)methyl)phenyl)ureido)-N-(4-sulfamoylphenyl)benzenesulfonamide | 559.1 |
| 26 | 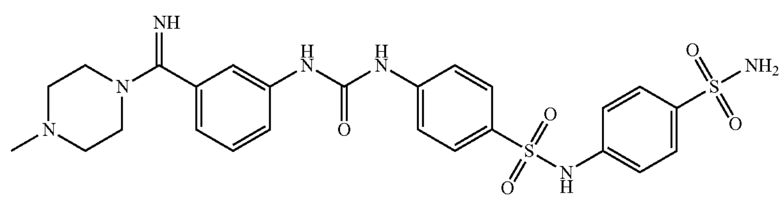 [SMILES: CN1CCN(C(=N)c2cccc(NC(=O)Nc3ccc(S(=O)(=O)Nc4ccc(S(N)(=O)=O)cc4)cc3)c2)CC1] | 4-(3-(imino(4-methylpiperazin-1-yl)methyl)phenyl)ureido)-N-(4-sulfamoylphenyl)benzenesulfonamide | 572.1 |

TABLE 1-continued

Exemplary compounds of formula (I) of the present invention include, but not limited to the followings:

| No. | Structure | Name | LC/MS [M + H]⁺ |
|---|---|---|---|
| 27 | 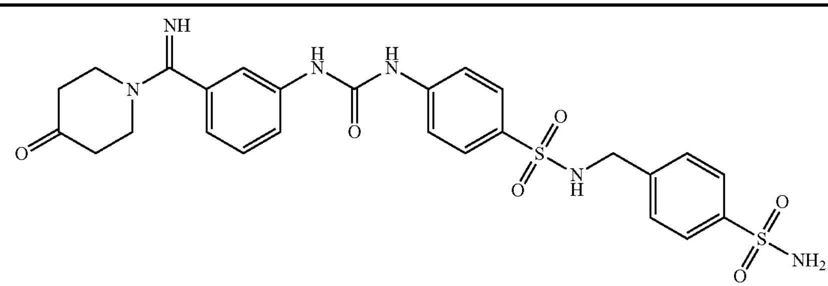 | 4-(3-(3-(imino(4-oxopiperidin-1-yl)methyl)phenyl)ureido)-N-(4-sulfamoylbenzyl)benzenesulfonamide | 585.2 |
| 28 | 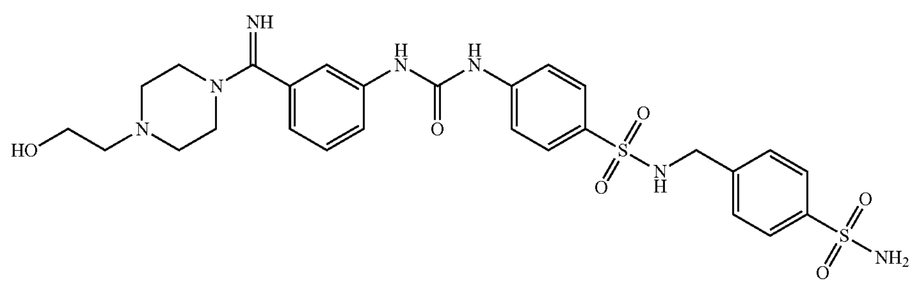 [SMILES: N=C(c1cccc(NC(=O)Nc2ccc(S(=O)(=O)NCc3ccc(S(N)(=O)=O)cc3)cc2)c1)N1CCN(CCO)CC1] | 4-(3-(3-((4-(2-hydroxyethyl)piperazin-1-yl)(imino)methyl)phenyl)ureido)-N-(4-sulfamoylbenzyl)benzenesulfonamide | 616.1 |
| 29 | 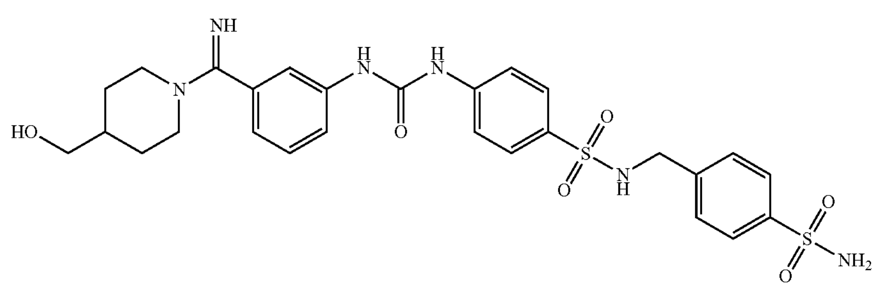 [SMILES: N=C(c1cccc(NC(=O)Nc2ccc(S(=O)(=O)NCc3ccc(S(N)(=O)=O)cc3)cc2)c1)N1CCC(CO)CC1] | 4-(3-(3-((4-(hydroxymethyl)piperidin-1-yl)(imino)methyl)phenyl)ureido)-N-(4-sulfamoylbenzyl)benzenesulfonamide | 601.1 |

TABLE 1-continued

Exemplary compounds of formula (I) of the present invention include, but not limited to the followings:

| No. | Structure | Name | LC/MS [M+H]+ |
|---|---|---|---|
| 30 | 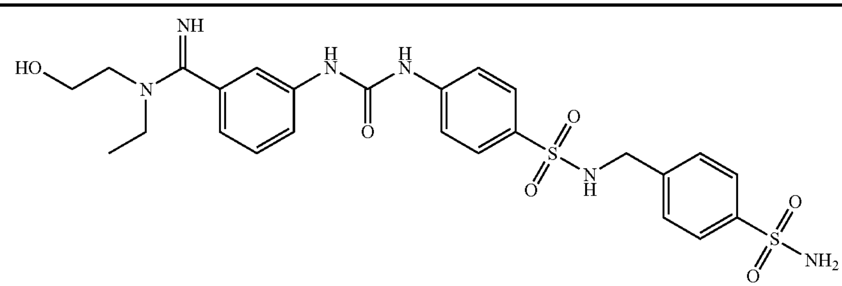 | N-ethyl-N-(2-hydroxyethyl)-3-(3-(4-(N-(4-sulfamoylbenzyl)sulfamoyl)phenyl)ureido)benzimidamide | 575.1 |
| 31 | 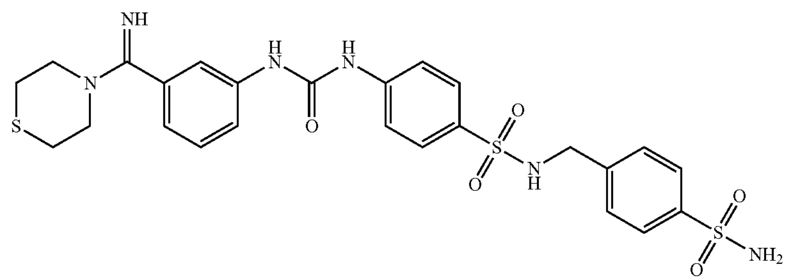 [SMILES: N=C(c1cccc(NC(=O)Nc2ccc(S(=O)(=O)NCc3ccc(S(N)(=O)=O)cc3)cc2)c1)N1CCSCC1] | 4-(3-(3-(imino(thiomorpholino)methyl)phenyl)ureido)-N-(4-sulfamoylbenzyl)benzenesulfonamide | 589.0 |
| 32 | 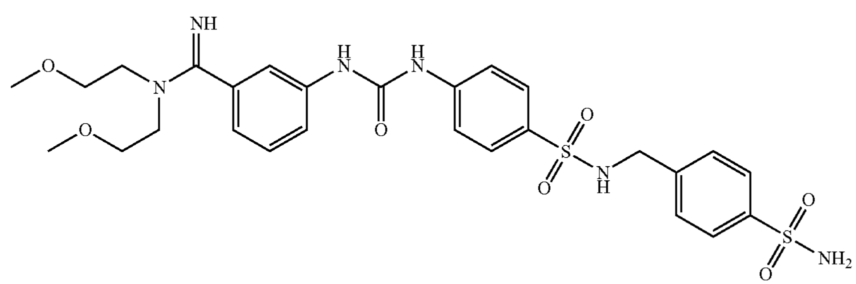 [SMILES: COCCN(CCOC)C(=N)c1cccc(NC(=O)Nc2ccc(S(=O)(=O)NCc3ccc(S(N)(=O)=O)cc3)cc2)c1] | N,N-bis(2-methoxyethyl)-3-(3-(4-(N-(4-sulfamoylbenzyl)sulfamoyl)phenyl)ureido)benzimidamide | 619.1 |

TABLE 1-continued

Exemplary compounds of formula (I) of the present invention include, but not limited to the followings:

| No. | Structure | Name | LC/MS [M + H]+ |
|---|---|---|---|
| 33 | 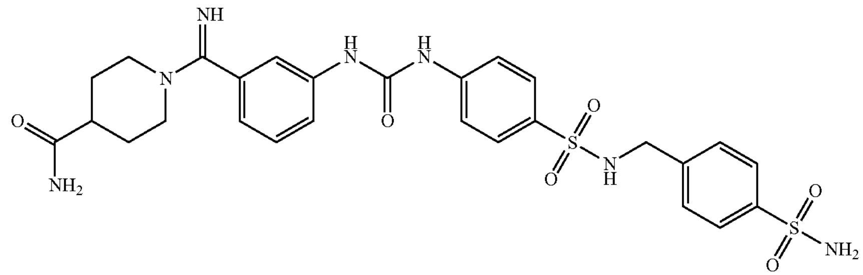 [SMILES: N=C(c1cccc(NC(=O)Nc2ccc(S(=O)(=O)NCc3ccc(S(N)(=O)=O)cc3)cc2)c1)N1CCC(C(N)=O)CC1] | 1-(imino(3-(4-(N-(4-sulfamoylbenzyl)sulfamoyl)phenyl)ureido)phenyl)methyl)piperidin-4-carboxamide | 614.1 |
| 34 | 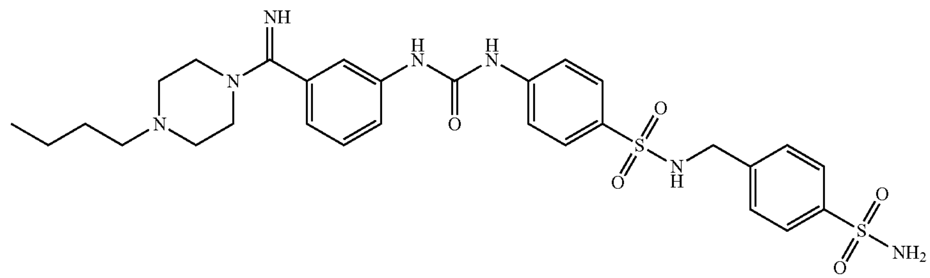 [SMILES: CCCCN1CCN(C(=N)c2cccc(NC(=O)Nc3ccc(S(=O)(=O)NCc4ccc(S(N)(=O)=O)cc4)cc3)c2)CC1] | 4-(3-(3-((4-butylpiperazin-1-yl)(imino)methyl)phenyl)ureido)-N-(4-sulfamoylbenzyl)benzenesulfonamide | 628.1 |
| 35 | 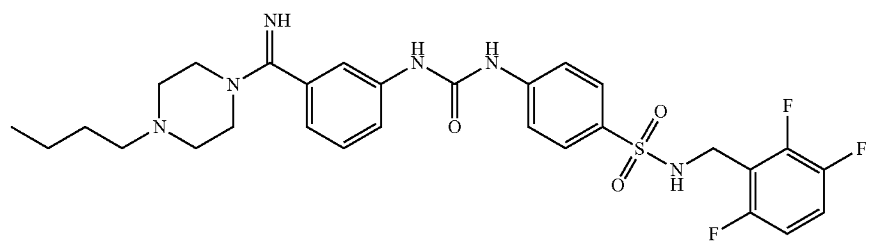 [SMILES: CCCCN1CCN(C(=N)c2cccc(NC(=O)Nc3ccc(S(=O)(=O)NCc4c(F)ccc(F)c4F)cc3)c2)CC1] | 4-(3-(3-((4-butylpiperazin-1-yl)(imino)methyl)phenyl)ureido)-N-(2,3,6-trifluorobenzyl)benzenesulfonamide | 603.2 |

TABLE 1-continued

Exemplary compounds of formula (I) of the present invention include, but not limited to the followings:

| No. | Structure | Name | LC/MS [M + H]+ |
|---|---|---|---|
| 36 | 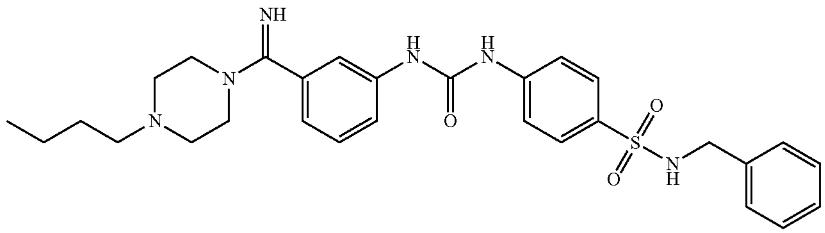 [SMILES: CCCCN1CCN(C(=N)c2cccc(NC(=O)Nc3ccc(S(=O)(=O)NCc4ccccc4)cc3)c2)CC1] | N-benzyl-4-(3-(3-((4-butyl)piperazin-1-yl)(imino)methyl)phenyl)ureido)benzenesulfonamide | 549.2 |
| 37 | 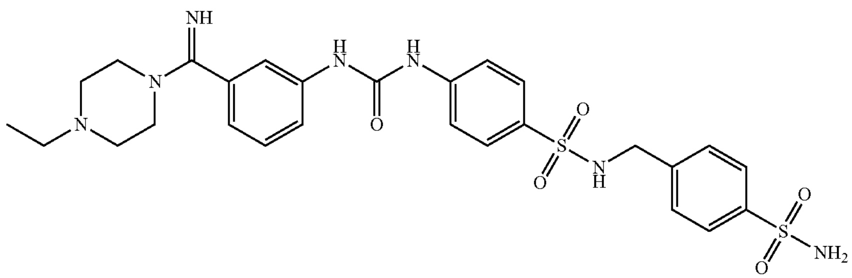 [SMILES: CCN1CCN(C(=N)c2cccc(NC(=O)Nc3ccc(S(=O)(=O)NCc4ccc(S(N)(=O)=O)cc4)cc3)c2)CC1] | 4-(3-(3-((4-ethylpiperazin-1-yl)(imino)methyl)phenyl)ureido)-N-(4-sulfamoylbenzyl)benzenesulfonamide | 600.1 |
| 38 | 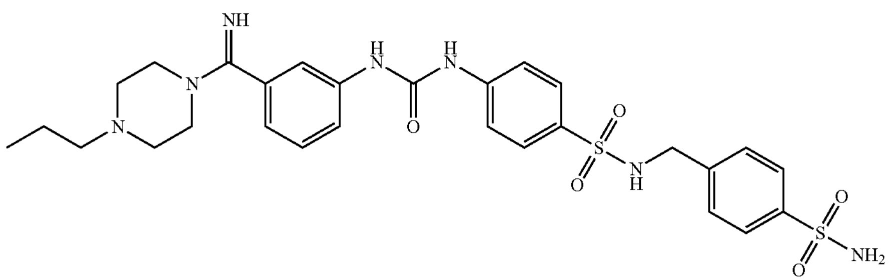 [SMILES: CCCN1CCN(C(=N)c2cccc(NC(=O)Nc3ccc(S(=O)(=O)NCc4ccc(S(N)(=O)=O)cc4)cc3)c2)CC1] | 4-(3-(3-(imino(4-propylpiperazin-1-yl)methyl)phenyl)ureido)-N-(4-sulfamoylbenzyl)benzenesulfonamide | 614.1 |

TABLE 1-continued

Exemplary compounds of formula (I) of the present invention include, but not limited to the followings:

| No. | Structure | Name | LC/MS [M + H]⁺ |
|---|---|---|---|
| 39 | 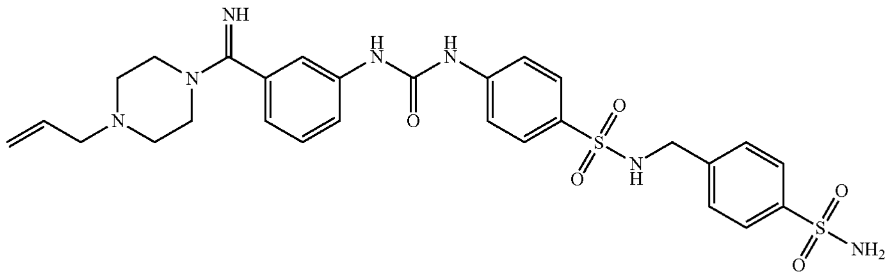 [SMILES: C=CCN1CCN(C(=N)c2cccc(NC(=O)Nc3ccc(S(=O)(=O)NCc4ccc(S(N)(=O)=O)cc4)cc3)c2)CC1] | 4-(3-(4-allylpiperazin-1-yl)(imino)methyl)phenyl)ureido)-N-(4-sulfamoylbenzyl)benzenesulfonamide | 612.1 |
| 40 | 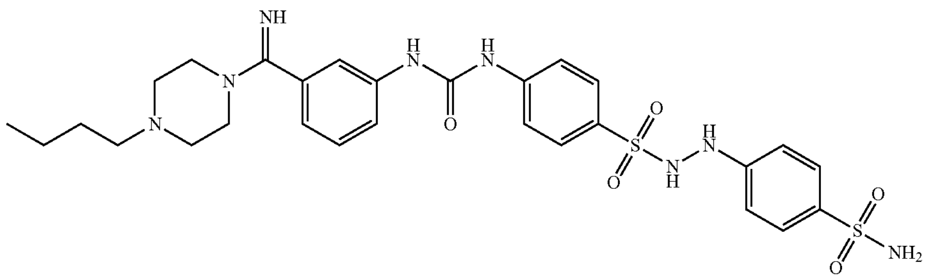 [SMILES: CCCCN1CCN(C(=N)c2cccc(NC(=O)Nc3ccc(S(=O)(=O)NNc4ccc(S(N)(=O)=O)cc4)cc3)c2)CC1] | 4-(2-(4-(3-((4-butylpiperazin-1-yl)(imino)methyl)phenyl)hydrazinyl)phenylsulfonyl)benzenesulfonamide | 629.2 |
| 41 | 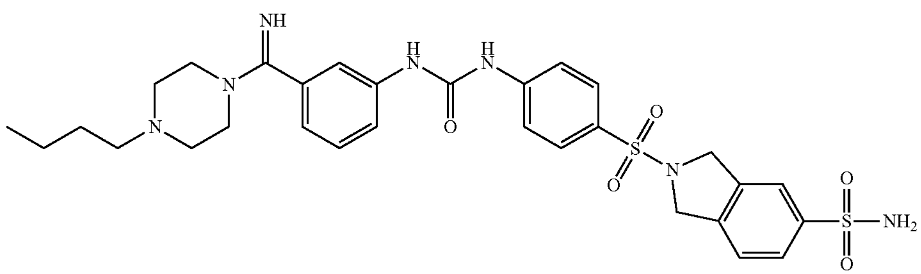 [SMILES: CCCCN1CCN(C(=N)c2cccc(NC(=O)Nc3ccc(S(=O)(=O)N4Cc5ccc(S(N)(=O)=O)cc5C4)cc3)c2)CC1] | 2-(4-(3-((4-butylpiperazin-1-yl)(imino)methyl)phenyl)ureido)phenylsulfonyl)isoindole-5-sulfonamide | 640.2 |

TABLE 1-continued

Exemplary compounds of formula (I) of the present invention include, but not limited to the followings:

| No. | Structure | Name | LC/MS [M+H]+ |
|---|---|---|---|
| 42 | 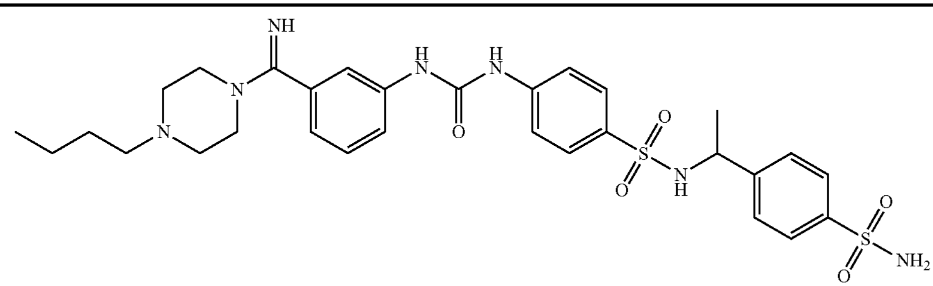 | 4-(3-(3-((4-butylpiperazin-1-yl)(imino)methyl)phenyl)ureido)-N-(1-(4-sulfamoyl)phenyl)ethyl)benzenesulfonamide | 642.2 |
| 43 | 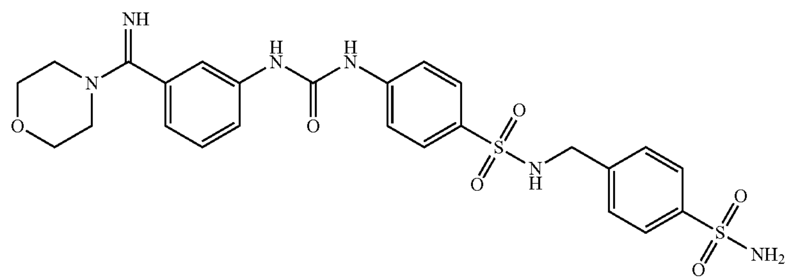 [SMILES: N=C(c1cccc(NC(=O)Nc2ccc(S(=O)(=O)NCc3ccc(S(N)(=O)=O)cc3)cc2)c1)N1CCOCC1] | 4-(3-(3-(imino(morpholino)methyl)phenyl)ureido)-N-(4-sulfamoylbenzyl)benzenesulfonamide | 573.1 |
| 44 | 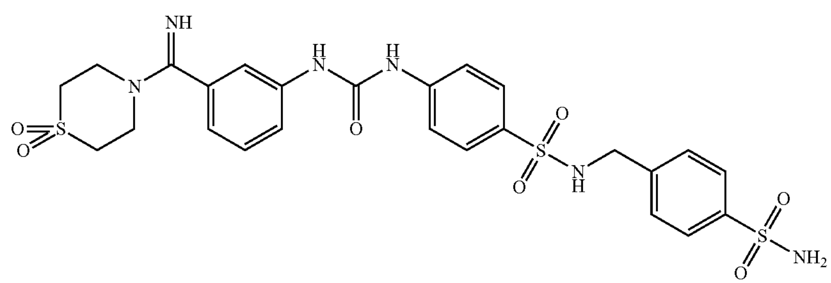 [SMILES: N=C(c1cccc(NC(=O)Nc2ccc(S(=O)(=O)NCc3ccc(S(N)(=O)=O)cc3)cc2)c1)N1CCS(=O)(=O)CC1] | 4-(3-(3-((1,1-dioxidothiomorpholino)(imino)methyl)phenyl)ureido)-N-(4-sulfamoylbenzyl)benzenesulfonamide | 621.1 |

TABLE 1-continued

Exemplary compounds of formula (I) of the present invention include, but not limited to the followings:

| No. | Structure | Name | LC/MS [M + H]+ |
|---|---|---|---|
| 45 | 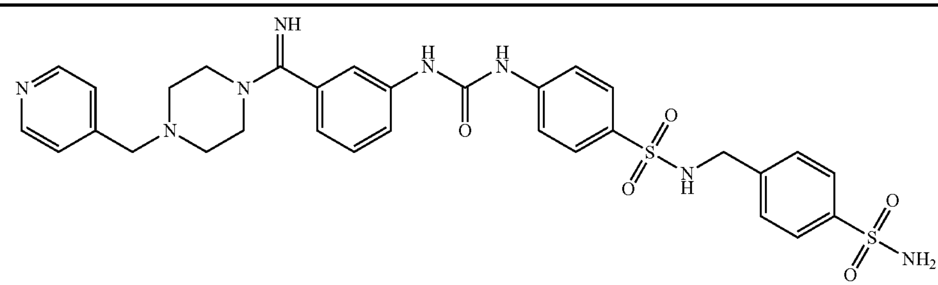 | 4-(3-(imino(4-(pyridin-4-ylmethyl)piperazin-1-yl)methyl)phenyl)ureido)-N-(4-sulfamoylbenzyl)benzenesulfonamide | 663.2 |
| 46 | 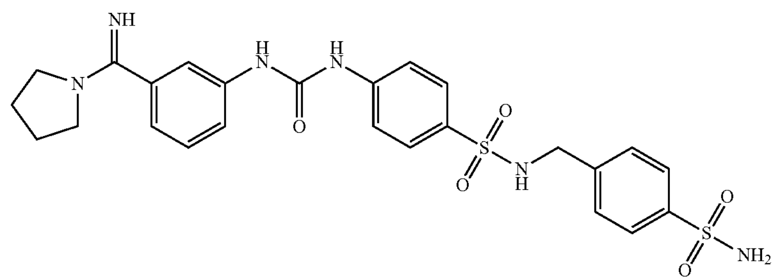 [SMILES: N=C(c1cccc(NC(=O)Nc2ccc(S(=O)(=O)NCc3ccc(S(N)(=O)=O)cc3)cc2)c1)N1CCCC1] | 4-(3-(imino(pyrrolidin-1-yl)methyl)phenyl)ureido)-N-(4-sulfamoylbenzyl)benzenesulfonamide | 557.1 |
| 47 | 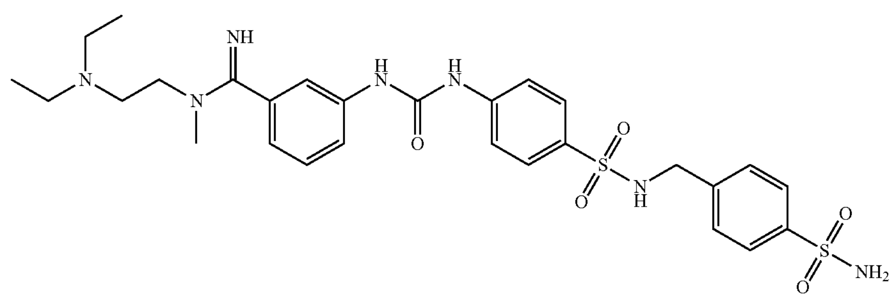 [SMILES: CCN(CC)CCN(C)C(=N)c1cccc(NC(=O)Nc2ccc(S(=O)(=O)NCc3ccc(S(N)(=O)=O)cc3)cc2)c1] | N-(2-(diethylamino)ethyl)-N-methyl-3-(4-(N-(4-sulfamoylbenzyl)sulfamoyl)phenyl)ureido)benzimidamide | 616.2 |

TABLE 1-continued

Exemplary compounds of formula (I) of the present invention include, but not limited to the followings:

| No. | Structure | Name | LC/MS [M + H]+ |
|---|---|---|---|
| 48 | 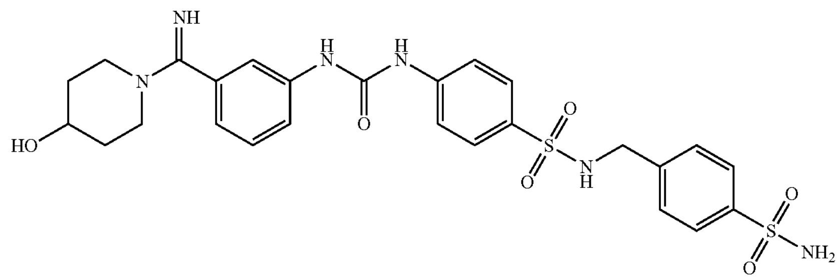 [SMILES: N=C(c1cccc(NC(=O)Nc2ccc(S(=O)(=O)NCc3ccc(S(N)(=O)=O)cc3)cc2)c1)N1CCC(O)CC1] | 4-(3-(3-((4-hydroxypiperidin-1-yl)(imino)methyl)phenyl)ureido)-N-(4-sulfamoylbenzyl)benzenesulfonamide | 587.1 |
| 49 | 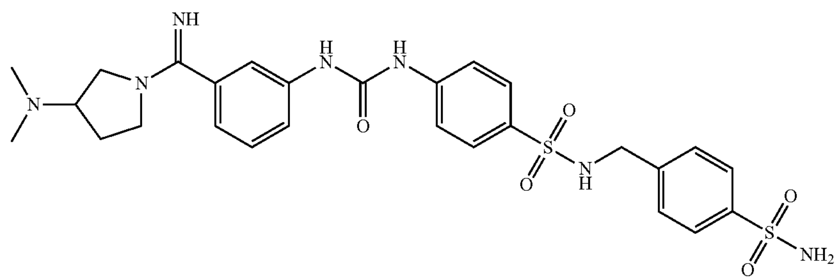 [SMILES: CN(C)C1CCN(C(=N)c2cccc(NC(=O)Nc3ccc(S(=O)(=O)NCc4ccc(S(N)(=O)=O)cc4)cc3)c2)C1] | 4-(3-(3-(3-(dimethylamino)pyrrolidin-1-yl)(imino)methyl)phenyl)ureido)-N-(4-sulfamoylbenzyl)benzenesulfonamide | 600.2 |
| 50 | 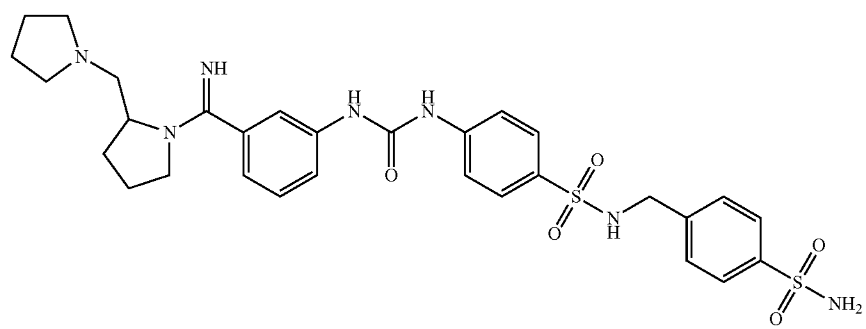 [SMILES: N=C(c1cccc(NC(=O)Nc2ccc(S(=O)(=O)NCc3ccc(S(N)(=O)=O)cc3)cc2)c1)N1CCCC1CN1CCCC1] | 4-(3-(3-(imino(2-(pyrrolidin-1-ylmethyl)pyrrolidin-1-yl)methyl)phenyl)ureido)-N-(4-sulfamoylbenzyl)benzenesulfonamide | 640.2 |

TABLE 1-continued

Exemplary compounds of formula (I) of the present invention include, but not limited to the followings:

| No. | Structure | Name | LC/MS [M + H]+ |
|---|---|---|---|
| 51 | 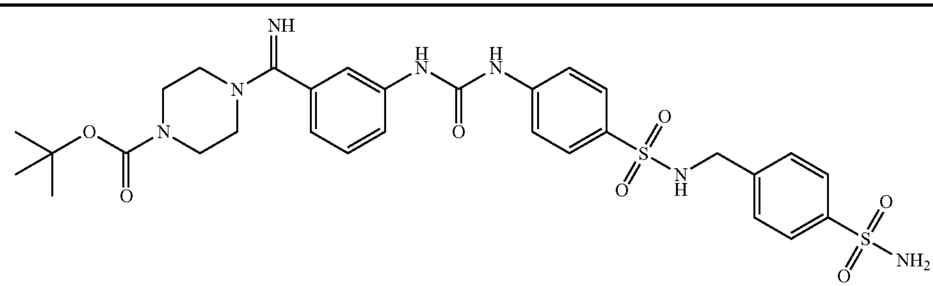 | tert-butyl 4-(imino(3-(3-(4-(N-(4-sulfamoylbenzyl)sulfamoyl)phenyl)ureido)phenyl)methyl)piperazine-1-carboxylate | 672.2 |
| 52 | 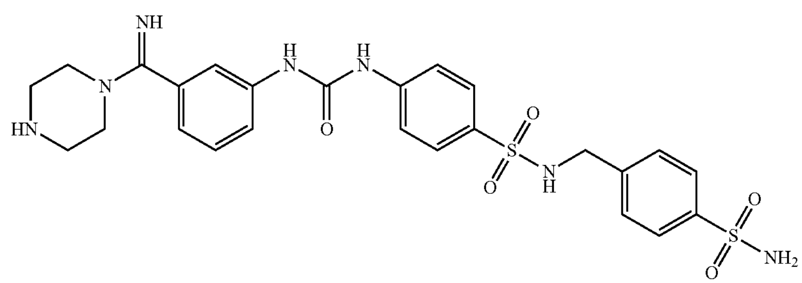 [SMILES: N=C(c1cccc(NC(=O)Nc2ccc(S(=O)(=O)NCc3ccc(S(N)(=O)=O)cc3)cc2)c1)N1CCNCC1] | 4-(3-(3-imino(piperazin-1-yl)methyl)phenyl)ureido)-N-(4-sulfamoylbenzyl)benzenesulfonamide | 572.1 |
| 53 | 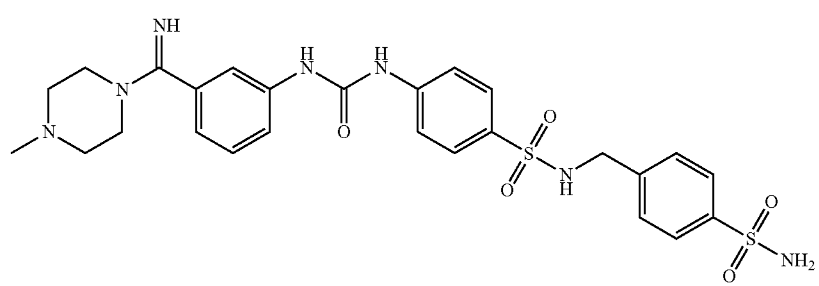 [SMILES: CN1CCN(C(=N)c2cccc(NC(=O)Nc3ccc(S(=O)(=O)NCc4ccc(S(N)(=O)=O)cc4)cc3)c2)CC1] | 4-(3-(3-(imino(4-methylpiperazin-1-yl)methyl)phenyl)ureido)-N-(4-sulfamoylbenzyl)benzenesulfonamide | 586.1 |

TABLE 1-continued

Exemplary compounds of formula (I) of the present invention include, but not limited to the followings:

| No. | Structure | Name | LC/MS [M + H]+ |
|---|---|---|---|
| 54 | 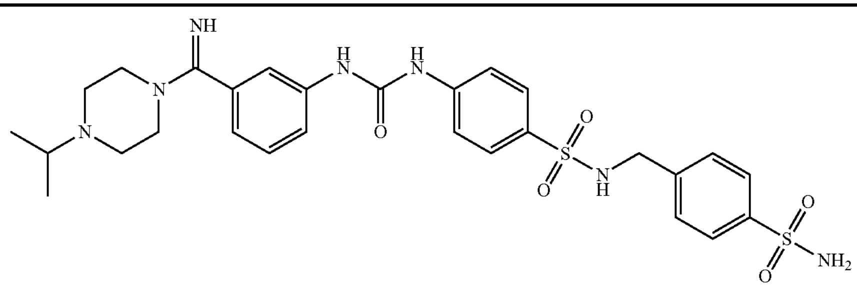 | 4-(3-(3-imino(4-isopropylpiperazin-1-yl)methyl)phenyl)ureido)-N-(4-sulfamoylbenzyl)benzenesulfonamide | 614.2 |
| 55 | 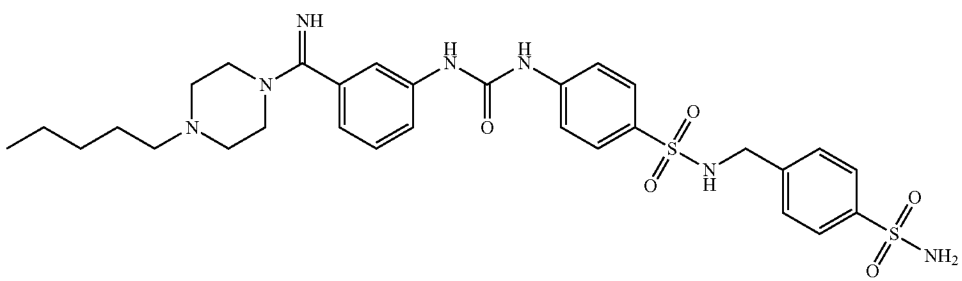 [SMILES: CCCCCN1CCN(C(=N)c2cccc(NC(=O)Nc3ccc(S(=O)(=O)NCc4ccc(S(N)(=O)=O)cc4)cc3)c2)CC1] | 4-(3-(3-(imino(4-pentylpiperazin-1-yl)methyl)phenyl)ureido)-N-(4-sulfamoylbenzyl)benzenesulfonamide | 642.1 |
| 56 | 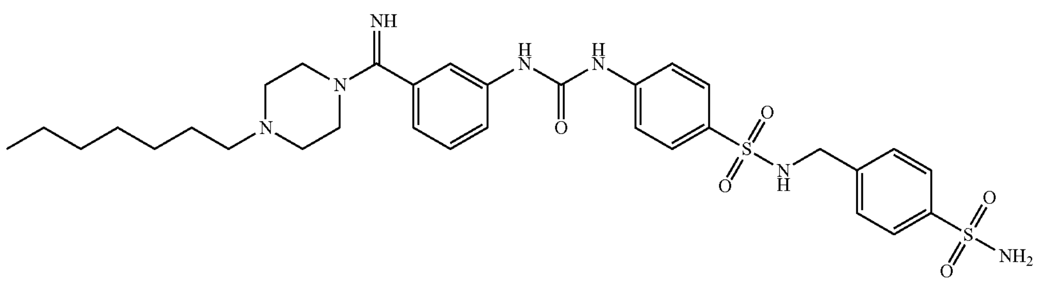 [SMILES: CCCCCCCN1CCN(C(=N)c2cccc(NC(=O)Nc3ccc(S(=O)(=O)NCc4ccc(S(N)(=O)=O)cc4)cc3)c2)CC1] | 4-(3-((4-heptylpiperazin-1-yl)(imino)methyl)phenyl)ureido)-N-(4-sulfamoylbenzyl)benzenesulfonamide | 670.1 |

TABLE 1-continued

Exemplary compounds of formula (I) of the present invention include, but not limited to the followings:

| No. | Structure | Name | LC/MS [M + H]⁺ |
|---|---|---|---|
| 57 | 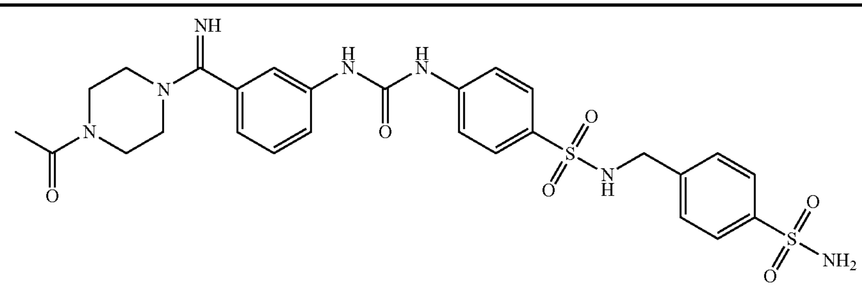 | 4-(3-(3-((4-acetylpiperazin-1-yl)(imino)methyl)phenyl)ureido)-N-(4-sulfamoylbenzyl)benzenesulfonamide | 614.1 |
| 58 | 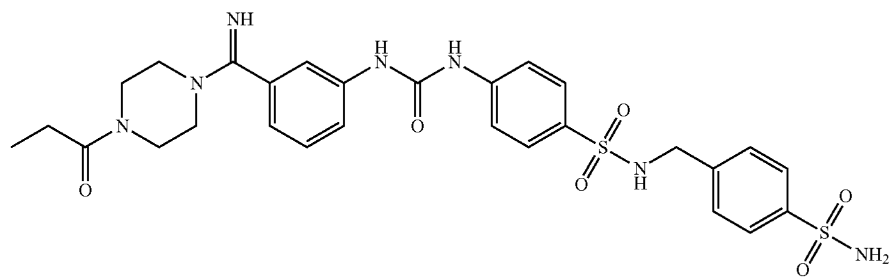 [SMILES: CCC(=O)N1CCN(C(=N)c2cccc(NC(=O)Nc3ccc(S(=O)(=O)NCc4ccc(S(N)(=O)=O)cc4)cc3)c2)CC1] | 4-(3-(3-(imino(4-propionylpiperazin-1-yl)methyl)phenyl)ureido)-N-(4-sulfamoylbenzyl)benzenesulfonamide | 628.0 |
| 59 | 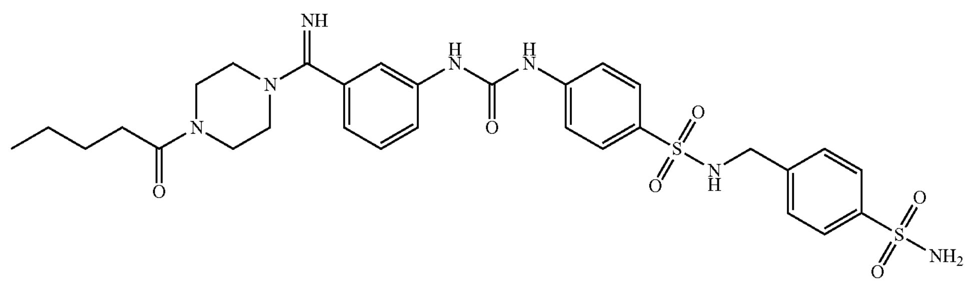 [SMILES: CCCCC(=O)N1CCN(C(=N)c2cccc(NC(=O)Nc3ccc(S(=O)(=O)NCc4ccc(S(N)(=O)=O)cc4)cc3)c2)CC1] | 4-(3-(3-(imino(4-pentenoylpiperazin-1-yl)methyl)phenyl)ureido)-N-(4-sulfamoylbenzyl)benzenesulfonamide | 656.0 |

TABLE 1-continued

Exemplary compounds of formula (I) of the present invention include, but not limited to the followings:

| No. | Structure | Name | LC/MS [M + H]+ |
|---|---|---|---|
| 60 | 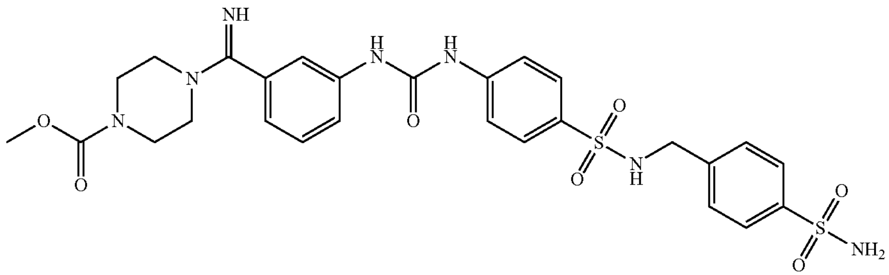 [SMILES: COC(=O)N1CCN(C(=N)c2cccc(NC(=O)Nc3ccc(S(=O)(=O)NCc4ccc(S(N)(=O)=O)cc4)cc3)c2)CC1] | methyl 4-(imino(3-(3-(4-(N-(4-sulfamoylbenzyl)sulfamoyl)phenyl)ureido)phenyl)methyl)piperazin-1-carboxylate | 630.1 |
| 61 | 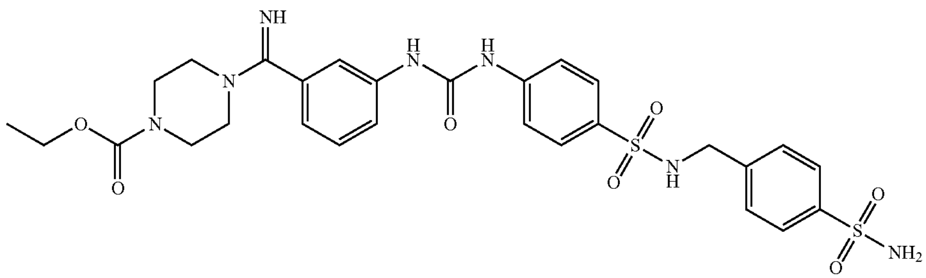 [SMILES: CCOC(=O)N1CCN(C(=N)c2cccc(NC(=O)Nc3ccc(S(=O)(=O)NCc4ccc(S(N)(=O)=O)cc4)cc3)c2)CC1] | ethyl 4-(imino(3-(3-(4-(N-(4-sulfamoylbenzyl)sulfamoyl)phenyl)ureido)phenyl)methyl)piperazin-1-carboxylate | 644.1 |
| 62 | 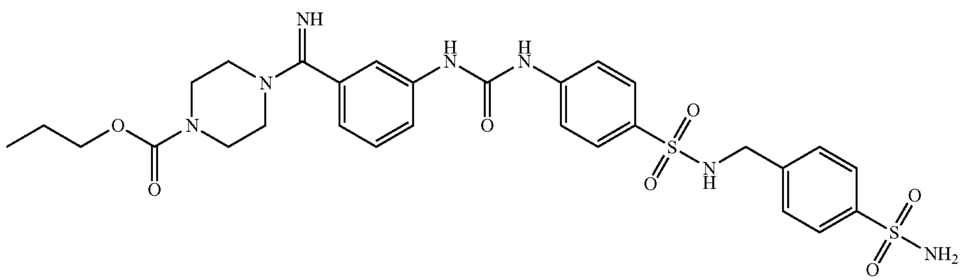 [SMILES: CCCOC(=O)N1CCN(C(=N)c2cccc(NC(=O)Nc3ccc(S(=O)(=O)NCc4ccc(S(N)(=O)=O)cc4)cc3)c2)CC1] | propyl 4-(imino(3-(3-(4-(N-(4-sulfamoylbenzyl)sulfamoyl)phenyl)ureido)phenyl)methyl)piperazin-1-carboxylate | 658.1 |

TABLE 1-continued

Exemplary compounds of formula (I) of the present invention include, but not limited to the followings:

| No. | Structure | Name | LC/MS [M + H]⁺ |
|---|---|---|---|
| 63 | 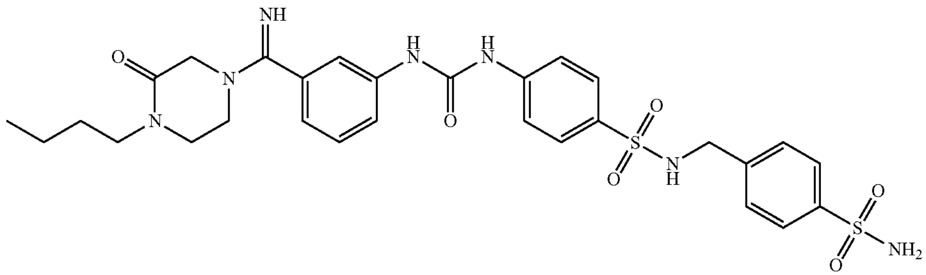 [SMILES: CCCCN1CCN(C(=N)c2cccc(NC(=O)Nc3ccc(S(=O)(=O)NCc4ccc(S(N)(=O)=O)cc4)cc3)c2)CC1=O] | 4-(3-(3-((4-butyl-3-oxopiperazin-1-yl)(imino)methyl)phenyl)ureido)-N-(4-sulfamoylbenzyl)benzenesulfonamide | 642.1 |
| 64 | 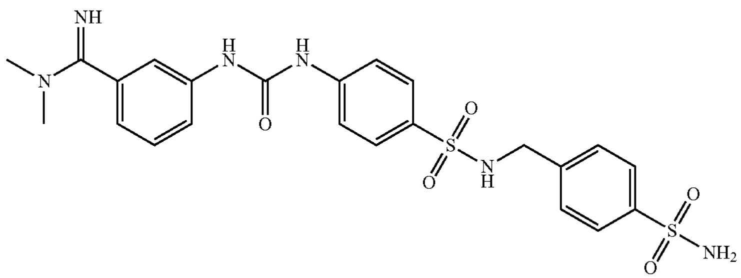 [SMILES: CN(C)C(=N)c1cccc(NC(=O)Nc2ccc(S(=O)(=O)NCc3ccc(S(N)(=O)=O)cc3)cc2)c1] | N,N-dimethyl-3-(3-(4-(N-(4-sulfamoylbenzyl)sulfamoyl)phenyl)ureido)benzimidamide | 531.1 |
| 65 | 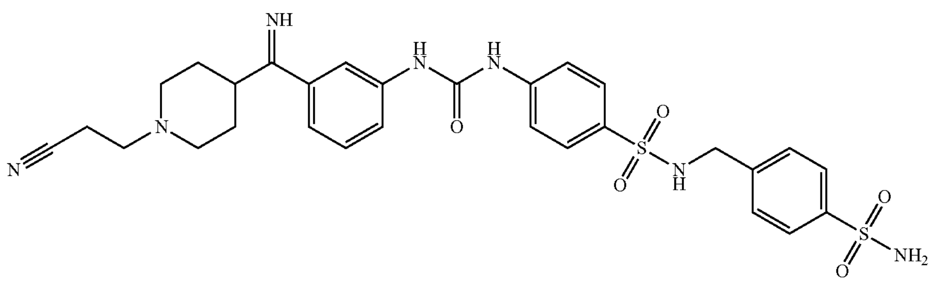 [SMILES: N#CCCN1CCC(C(=N)c2cccc(NC(=O)Nc3ccc(S(=O)(=O)NCc4ccc(S(N)(=O)=O)cc4)cc3)c2)CC1] | 4-(3-(3-((4-(2-cyanoethyl)piperazin-1-yl)(imino)methyl)phenyl)ureido)-N-(4-sulfamoylbenzyl)benzenesulfonamide | 625.1 |

TABLE 1-continued

Exemplary compounds of formula (I) of the present invention include, but not limited to the followings:

| No. | Structure | Name | LC/MS [M + H]+ |
|---|---|---|---|
| 66 | 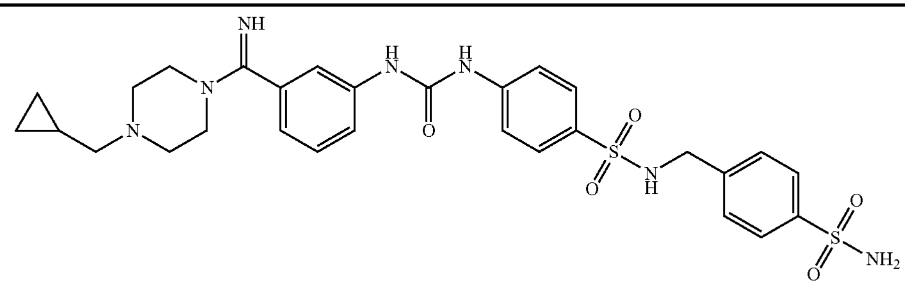 | 4-(3-(3-(4-(cyclopropylmethyl)piperazin-1-yl)(imino)methyl)phenyl)ureido)-N-(4-sulfamoylbenzyl)benzenesulfonamide | 626.1 |
| 67 | 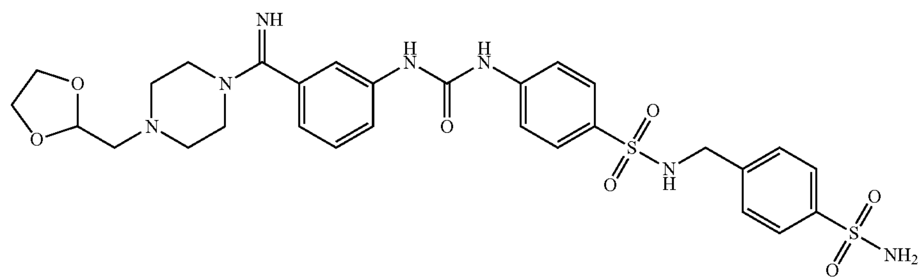 [SMILES: N=C(c1cccc(NC(=O)Nc2ccc(S(=O)(=O)NCc3ccc(S(N)(=O)=O)cc3)cc2)c1)N1CCN(CC2OCCO2)CC1] | 4-(3-(3-(4-((1,3-dioxolan-2-yl)methyl)piperazin-1-yl)(imino)methyl)phenyl)ureido)-N-(4-sulfamoylbenzyl)benzenesulfonamide | 658.1 |
| 68 | 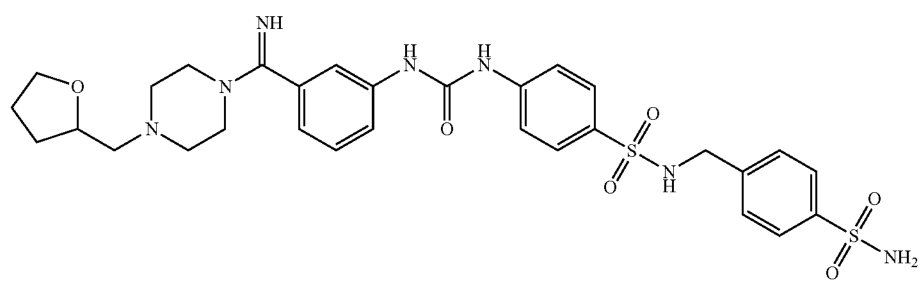 [SMILES: N=C(c1cccc(NC(=O)Nc2ccc(S(=O)(=O)NCc3ccc(S(N)(=O)=O)cc3)cc2)c1)N1CCN(CC2CCCO2)CC1] | 4-(3-(3-(imino(4-((tetrahydrofuran-2-yl)methyl)piperazin-1-yl)methyl)phenyl)ureido)-N-(4-sulfamoylbenzyl)benzenesulfonamide | 656.1 |

TABLE 1-continued

Exemplary compounds of formula (I) of the present invention include, but not limited to the followings:

| No. | Structure | Name | LC/MS [M + H]+ |
|---|---|---|---|
| 69 | 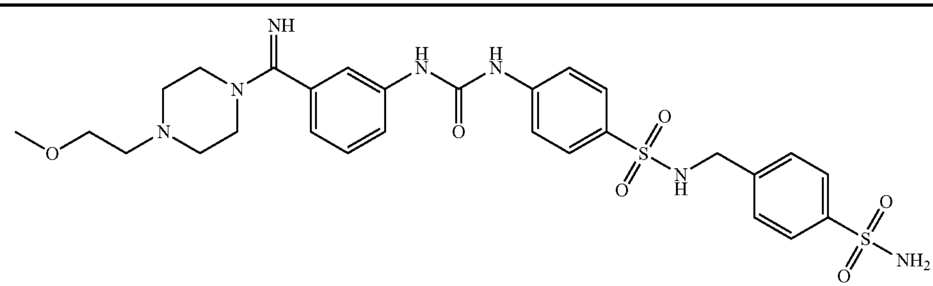 | 4-(3-(imino(4-(2-methoxyethyl)piperazin-1-yl)methyl)phenyl)ureido)-N-(4-sulfamoylbenzyl)benzenesulfonamide | 630.1 |
| 70 | 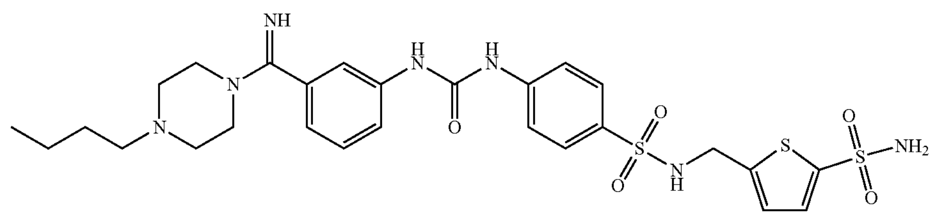 [SMILES: CCCCN1CCN(C(=N)c2cccc(NC(=O)Nc3ccc(S(=O)(=O)NCc4ccc(S(N)(=O)=O)s4)cc3)c2)CC1] | 5-((4-(3-(3-((4-butylpiperazin-1-yl)(imino)methyl)phenylureido)phenylsulfonamido)methyl)thiophene-2-sulfonamide | 634.1 |
| 71 | 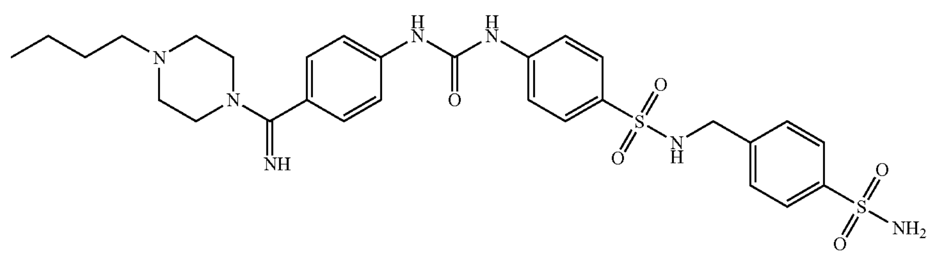 [SMILES: CCCCN1CCN(C(=N)c2ccc(NC(=O)Nc3ccc(S(=O)(=O)NCc4ccc(S(N)(=O)=O)cc4)cc3)cc2)CC1] | 4-(3-(4-((4-butylpiperazin-1-yl)(imino)methyl)phenyl)ureido)-N-(4-sulfamoylbenzyl)benzenesulfonamide | 628.1 |

TABLE 1-continued

Exemplary compounds of formula (I) of the present invention include, but not limited to the followings:

| No. | Structure | Name | LC/MS [M + H]+ |
|---|---|---|---|
| 72 | 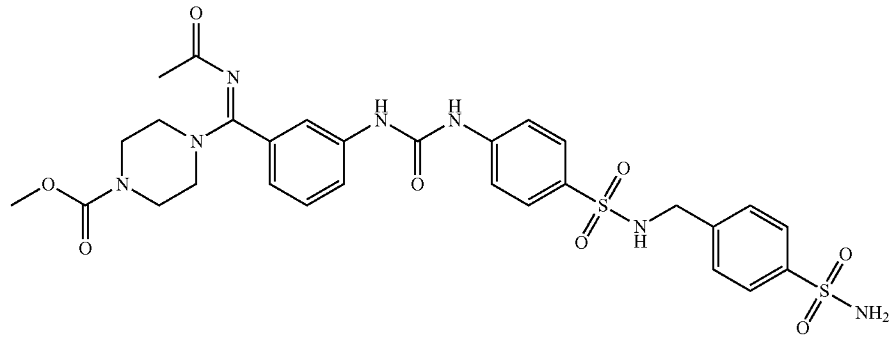 [SMILES: COC(=O)N1CCN(/C(=N\C(C)=O)c2cccc(NC(=O)Nc3ccc(S(=O)(=O)NCc4ccc(S(N)(=O)=O)cc4)cc3)c2)CC1] | methyl 4-((acetylamino)(3-(4-(N-(4-sulfamoylbenzyl)sulfamoyl)phenyl)ureido)phenyl)methyl)piperazine-1-carboxylate | 672.2 |
| 73 | 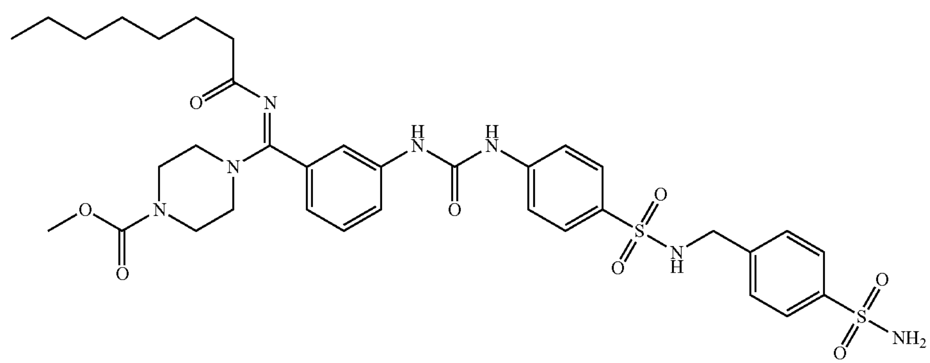 [SMILES: CCCCCCCC(=O)/N=C(/c1cccc(NC(=O)Nc2ccc(S(=O)(=O)NCc3ccc(S(N)(=O)=O)cc3)cc2)c1)N1CCN(C(=O)OC)CC1] | methyl 4-((octanoylimino)(3-(4-(N-(4-sulfamoylbenzyl)sulfamoyl)phenyl)ureido)phenyl)methyl)piperazine-1-carboxylate | 756.3 |
| 74 | 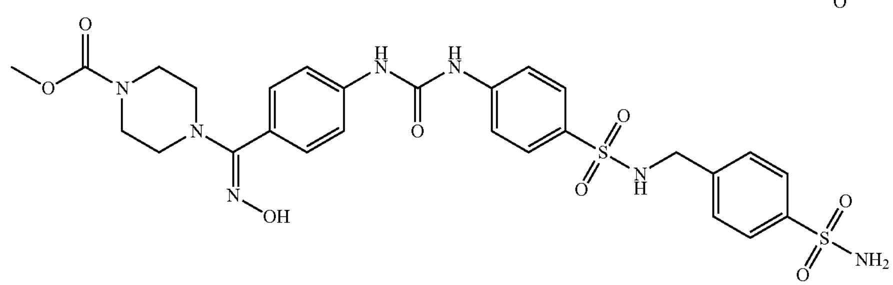 | methyl 4-((hydroxyimino)(4-(3-(4-(N-(4-sulfamoylbenzyl)sulfamoyl)phenyl)ureido)phenyl)methyl)piperazine-1-carboxylate | 646.2 |

In Vitro Assays

Antiplasmodial Activity against Dd2 Strain of *Plasmodium falciparum*

For the determination of the antiplasmodial activity of the compounds described above, the multiresistant Dd2 strain of *Plasmodium falciparum* was used. The incorporation of [8-$^3$H]hypoxanthine into the parasitic nucleic acids was measured. The plasmodia were incubated at 0.3% parasitaemia and an erythrocyte haematocrit of 2.5% in the presence of different concentrations of the compounds in a final volume of 200 µl. The medium employed was RPMI 1640 which contained 10% of heat-treated human serum and 3 mg/l of gentamycin. In the incubations, the concentrations of the compounds varied from 0.001 to 100 µM. After 48 h, each batch was treated with 50 µl of [8-$^3$H]hypoxanthine (1 mCi/ml) and incubated for a further 18 h. The cells were filtered off, washed and suspended in 20 µl of scintillation fluid. The radioactive hypoxanthine absorbed by the parasites was then quantified using a scintillation counter. The results were presented graphically and the $IC_{50}$ value was determined using a fitting function. The value $IC_{50}$, the 'inhibition constant', indicates the value in µMol/l at which 50% parasite growth inhibition occurs (R. E. Desjardins, et al., *Antimicrobiol. Agent Chemother.* 16, pp. 710-718, 1979; J. D. Chulay, et al., *Exp. Parasitol.* 55, pp. 138-146, 1983). In table 2, the antimalaria activity was defined as following: A: $IC_{50}$ value≧1 µM; B: $IC_{50}$ value between 0.99 µM and 0.21 µM; C: $IC_{50}$ value between 0.20 µM and 0.02 µM; D: $IC_{50}$ value <0.02 µM.

TABLE 2

In vitro antiplasmodia activity:

| Antiplasmodia activity | Compound |
|---|---|
| A | 1, 2, 3, 8, 9, 12, 13, 17, 18, 19, 20, 21, 22, 24, 25, 26, 40; |
| B | 4, 23, 27, 29, 30, 31, 32, 35, 36, 42, 45, 51, 53, 64, 65; |
| C | 5, 6, 7, 10, 11, 14, 15, 16, 28, 33, 37, 41, 43, 44, 46, 47, 48, 49, 50, 52, 54, 56, 57, 59, 67, 68, 69, 70, 71; |
| D | 34, 38, 39, 55, 58, 60, 61, 62, 63, 66; |

Solubility and solubility-range Determination in 50 mM Phosphate Buffer at Different pH The compounds were dissolved in DMSO at a concentration of 20 mg/ml. These stock solutions were further diluted 1:1 with DMSO (50 µl solution+50 µl DMSO) in seven steps. Subsequently, these solutions were diluted 1:100 (5 µl DMSO-stock+495 µl 50 mM phosphate buffer) in all four pH buffers (respectively: pH=4; pH=6; pH=7.4; pH=9) resulting in a final DMSO concentration of 1% in the buffers. These dilutions were vigorously mixed and transferred into 96-well reading plate. The plates were incubated in a shaker (600 rpm) at 23° C. for 24 hours. After that, the contents of the wells were mixed with a pipette and optical density (OD) was recorded at wavelengths of 550 nm; 600 nm; 650 nm and 700 nm in the Tecan Sunrise plate reader. The cut-off OD sum for an undissolved concentration of a compound was defined as follows: Cut off OD sum=mean blank OD+0.050 OD. For the determination of the solubility range, the following rule was applied:
OD>cut off=>compound not dissolved at this concentration
OD<cut-off=>compound dissolved at this concentration For the determination of the solubility, a titration curve (OD/concentration) was prepared and the concentrations were determined based on the measured OD of the mixture supernatant after centrifugation. The solubility values are given in µg/ml (table 3).

Determination of In Vitro Clearance Using Human Liver Microsomes

These experiments were performed at Nikem Research (Via Zambeletti 25; Baranzate, Milan, Italy).

Test compounds in duplicate at the final concentration of 1 µM were dissolved in DMSO and pre-incubated for 10 min at 37° C. in phosphate buffer pH 7.4, 3 mM $MgCl_2$, with human liver microsomes at the final concentration of 0.5 mg/ml. After the pre-incubation period, reaction was started by adding the cofactor mixture (NADP, Glc6P, G6P-DH); samples were taken at time 0, 5, 10, 15, 20 and 30 min and added to acetonitrile to quench the metabolic reaction, centrifuged and supernatant analysed and quantified by HPLC/MS. A control sample without cofactors was always added in order to check the chemical stability of test compounds. 7-ethoxycoumarin was added as reference standard. A fixed concentration of verapamil was added in every sample as internal standard for HPLC/MS. The concentration of the remaining compound at different times was determined by HPLC/MS.

The rate constant, k ($min^{-1}$) derived for the exponential decay equation (peak area vs time) was used to calculate the rate of intrinsic clearance (Cli) of the compounds using the following equations: Cli (µl/min/mg compound)=k×V; where:
V (µl/mg compound)=incubation volume/mg compound added.

In table 3 the clearance (in vitro metabolic stability) classification was as follows: Cli<10=compound stable; Cli between 10 and 60=low metabolism; Cli between 60 and 600=medium metabolism Cli>600=high metabolism.

TABLE 3

Solubility and in vitro metabolic stability

| No. | Solubility or solubility range | In vitro metabolism as determined from Cli |
|---|---|---|
| 1 |  | low |
| 23 |  | low |
| 34 | pH 4 = 960 µg/ml<br>pH 6 = 960 µg/ml<br>pH 7.4 = 750 µg/ml<br>pH 9 = 540 µg/ml | medium |
| 37 |  | medium |
| 38 | pH 4 = >200 µg/ml<br>pH 6 = >200 µg/ml<br>pH 7.4 = >200 µg/ml<br>pH 9 = >200 µg/ml | medium |
| 41 |  | medium |
| 43 |  | medium |
| 44 | pH 4 = >200 µg/ml<br>pH 6 = >200 µg/ml<br>pH 7.4 = >200 µg/ml<br>pH 9 = >200 µg/ml |  |
| 52 | pH 4 = >200 µg/ml<br>pH 6 = >200 µg/ml<br>pH 7.4 = >200 µg/ml<br>pH 9 = >200 µg/ml | low |
| 53 |  | low |
| 54 |  | medium |
| 58 | pH 4 = >200 µg/ml<br>pH 6 = >200 µg/ml<br>pH 7.4 = >200 µg/ml<br>pH 9 = >200 µg/ml | low |

TABLE 3-continued

Solubility and in vitro metabolic stability

| No. | Solubility or solubility range | In vitro metabolism as determined from Cli |
|---|---|---|
| 60 | pH 4 = 1480 µg/ml | medium |
|  | pH 6 = 1286 µg/ml |  |
|  | pH 7.4 = 763 µg/ml |  |
|  | pH 9 = 456 µg/ml |  |
| 63 |  | medium |
| 64 |  | low |
| 65 |  | medium |
| 66 |  | medium |
| 69 |  | medium |
| 70 |  | medium |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the formula (I) or a physiologically acceptable salt thereof, or a mono-, di-, tri- or tetrahydrate of said compound or said salt, formula (I)

wherein
$R^a$ is hydrogen;
$R^b$ and $R^c$ together form a 5- or 6-membered saturated heterocycloalkyl ring, which contains one or more ring heteroatoms each selected from the group consisting of O, S and N, and which has 0 or 1 substituents R", and which is optionally substituted by 1 or 2 oxo groups;
R' independently represents hydrogen, —CO$_2$R", —CONHR", —CR'O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, amino, aminoalkyl, alkylamino, alkoxy, —OH, —SH, alkylthio, hydroxyalkyl, hydroxyalkylamino, halogen, haloalkyl, haloalkoxy, aryl, haloaryl, haloarylalkyl, arylalkyl, heterocyclyl or heteroaryl;
R" independently represents hydrogen, —(CH$_2$)$_m$R', —CO$_2$R', —CON(R')$_2$, —CR'O, —SO$_2$N(R")$_2$, —NR'—CO-haloalkyl, —NO$_2$, —NR'—SO$_2$-haloalkyl, —NR'—SO$_2$-alkyl, —NR'—SO$_2$-aryl, —NR'—SO$_2$-heteroaryl, —SO$_2$-alkyl, —SO$_2$-aryl, —SO$_2$-heteroaryl, —NR'—CO-alkyl, —NR'—CO-aryl, —NR'—CO-heteroaryl, —NR'—CO—N(R')$_2$, —CN, alkyl, amino, aminoalkyl, alkylamino, alkoxy, alkoxyalkyl, hydroxyl, —SH, alkylthio, hydroxyalkyl, hydroxyalkylamino, halogen, haloalkyl, or haloalkoxy;
$R^1$ and $R^2$ represent hydrogen;
m is 1, 2, 3, 4, 5, 6, 7, 8, 9, 10, 11, or 12;
X is N,
$R^3$ is hydrogen; and
$R^4$ is arylalkyl or aryl, which is optionally substituted with R".

2. A compound according to claim 1, wherein $R^4$ is phenyl or benzyl.

3. A compound according to claim 1, wherein $R^4$ is phenyl or benzyl substituted with SO$_2$NH$_2$.

4. A compound according to claim 1, wherein $R^4$ is benzyl substituted with SO$_2$NH$_2$.

5. A pharmaceutical composition, comprising a compound according to claim 1 and a pharmaceutically acceptable carrier or diluent.

6. A method of treating or preventing or ameliorating malaria in a subject, comprising administering an effective amount of a compound according to claim 1 to said subject.

7. A method according to claim 6, which is for treating malaria.

8. A method according to claim 6, wherein the malaria is caused by a strain of *Plasmodium falciparum*.

9. A method according to claim 6, wherein the compound of formula (I) is administered in combination with another antimalaria compound.

10. A method according to claim 9, wherein the other antimalaria compound is selected from chloroquine, sulfadoxine/pyrimethamine, dapsone/pyrimethamine, halofantrine, amodiaquine, mefloquine, quinine, quinidine, doxycycline, lumefantrine, primaquine, proguanil, atovaquone, pyronaridine, chlorproguanyl, artemesinin, arteflene, artemether, artesunate or trimethoprim.

11. A method according to claim 8, wherein the compound of formula (I) is administered in combination with another antimalaria compound.

12. A method according to claim 11, wherein the other antimalaria compound is selected from chloroquine, sulfadoxine/pyrimethamine, dapsone/pyrimethamine, halofantrine, amodiaquine, mefloquine, quinine, quinidine, doxycycline, lumefantrine, primaquine, proguanil, atovaquone, pyronaridine, chlorproguanyl, artemesinin, arteflene, artemether, artesunate or trimethoprim.

13. A compound according to claim 1, or a physiologically acceptable salt thereof.

14. A method of treating or preventing or ameliorating malaria in a subject, comprising administering an effective amount of a compound according to claim 13 to said subject.

15. A compound according to claim 1, wherein $R^b$ and $R^c$ together form a heterocyclic ring, which has 0 or 1 substituents R", which heterocyclic ring is selected from the group consisting of piperidinyl, piperazinyl, morpholinyl, pyrrolidinyl, thiazolidinyl, thiomorpholinyl, piperidin-4-one-1-yl, S,S-dioxo-thio-morpholinyl, and piperazin-3-one-1-yl.

16. A compound according to claim 1, wherein R' independently represents hydrogen, —CN, cycloalkyl, —OH, heterocyclyl or heteroaryl.

17. A compound according to claim 1, wherein R" independently represents hydrogen, —(CH$_2$)$_m$R', —CO$_2$R', —CON(R')$_2$, —SO$_2$N(R')$_2$, —NR'—CO -alkyl, alkyl, alkylamino, alkoxyalkyl, hydroxyl, hydroxyalkyl, or halogen.

18. A compound according to claim 1, wherein R' independently represents hydrogen, —NO$_2$, —SO$_2$-alkyl, —CN, alkyl, cycloalkyl, amino, aminoalkyl, alkylamino, alkoxy, —OH, —SH, alkylthio, hydroxyalkyl, hydroxyalkylamino, halogen, haloalkyl, haloalkoxy, aryl, haloaryl, haloarylalkyl, arylalkyl, heterocyclyl or heteroaryl.

19. A compound of the formula (I) or a physiologically acceptable salt thereof, or a mono-, di-, tri- or tetrahydrate of said compound or said salt,

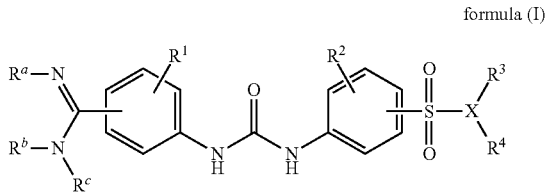

formula (I)

wherein
$R^a$ is hydrogen;
$R^b$ and $R^c$ together form a 5- or 6-membered saturated heterocycloalkyl ring, which contains one or more ring heteroatoms each selected from the group consisting of O, S and N, and which has 0 or 1 substituents R", and which is optionally substituted by 1 or 2 oxo groups
R' independently represents hydrogen, —CN, cycloalkyl, —OH, heterocyclyl or heteroaryl;
R" independently represents hydrogen, —$(CH_2)_m$R', —$CO_2$R'—CON(R')$_2$, —$SO_2$N(R')$_2$, —NR'—CO-alkyl, alkyl, alkylamino, alkoxyalkyl, hydroxyl, hydroxyalkyl, or halogen;
$R^1$ and $R^2$ represent hydrogen;
m is 1, 2, 3, 4, 5, 6, 7, 8, 9, 10, 11, or 12;
X is N,
$R^3$ is hydrogen; and
$R^4$ is arylalkyl or aryl, which is optionally substituted with R".

20. A compound according to claim 1, or a physiologically acceptable salt thereof.

21. A compound according to claim 20, wherein $R^b$ and $R^c$ together form a heterocyclic ring, which has 0 or 1 substituents R", which heterocyclic ring is selected from the group consisting of piperidinyl, piperazinyl, morpholinyl, pyrrolidinyl, thiazolidinyl, thiomorpholinyl, piperidin-4-one-1-yl, S,S-dioxo-thio -morpholinyl, and piperazin-3-one-1-yl.

22. A compound, which is one of the following compounds or a physiologically acceptable salt thereof, or a mono-, di-, tri- or tetrahydrate of said compound or said salt, 4-(3-(3-((4-butylpiperazin-1-yl)(imino)methyl)phenyl) ureido)benzenesulfonamide;
4-(3-(3-((4-hydroxypiperidin-1-yl)(imino)methyl)phenyl)ureido)benzenesulfonamide;
4-(3-(3-(imino(piperazin-1-yl)methyl)phenyl)ureido)benzenesulfonamide;
1-(4-(4-bromophenylsulfonyl)phenyl)-3-(3-((4-butylpiperazin-1-yl)(imino)methyl)phenyl)urea;
1-(4-(4-bromophenylsulfonyl)phenyl)-3-(3-((4-hydroxypiperidin- 1-yl)(imino)methyl)phenyl)urea;
1-(3-(imino(morpholino)methyl)phenyl)-3-(4-(4-nitrophenylsulfonyl)phenyl)urea;
1-(3-(imino(pyrrolidin-1-yl)methyl)phenyl)-3-(4-(4-nitrophenylsulfonyl)phenyl)urea;
1-(3-(imino(4-methylpiperazin-1-yl)methyl)phenyl)-3-(4-(4-nitrophenylsulfonyl)phenyl)urea;
1-(3-(imino(thiazolidin-3-yl)methyl)phenyl)-3-(4-(4-nitrophenylsulfonyl)phenyl)urea;
1-(3-((4-hydroxypiperidin-1-yl)(imino)methyl)phenyl)-3-(4-(4-nitrophenylsulfonyl)phenyl)urea;
1-(4-(4-chlorophenylsulfonyl)phenyl)-3-(3- ((4-hydroxypiperidin- 1-yl)(imino)methyl)phenyl)urea;
1-(4-(4-bromophenylsulfonyl)phenyl)-3-(3-((4-(hydroxymethyl)piperidin-1-yl)(imino)methyl)phenyl) urea;
3-(3-(4-(4-bromophenylsulfonyl)phenyl)ureido)-N,N-bis (2-methoxyethyl)benzimidamide;
1-(4-(4-bromophenylsulfonyl)phenyl)-3-(3-(imino (thiomorpholino)methyl)phenyl)urea;
1-(4-(4-bromophenylsulfonyl)phenyl)-3-(3-(imino(pyrrolidin-1-yl)methyl)phenyl)urea;
1-((3-(3-(4-(4-bromophenylsulfonyl)phenyl)ureido)phenyl) (imino)methyl)piperidine-4-carboxamide;
1-(4-(4-aminophenylsulfonyl)phenyl)-3-(3-((4-hydroxypiperidin- 1-yl)(imino)methyl)phenyl)urea;
4-(3-(3-((4-butylpiperazin-1-yl)(imino)methyl)phenyl) ureido)-N -methylbenzenesulfonamide;
4-(3-(3-((4-butylpiperazin-1-yl)(imino)methyl)phenyl) ureido)-N -propylbenzenesulfonamide;
4-(3-(3-((4-butylpiperazin-1-yl)(imino)methyl)phenyl) ureido) -N,N-bis(2-hydroxyethyl)benzenesulfonamide;
1-(3-((4-butylpiperazin-1-yl)(imino)methyl)phenyl)-3-(4-(morpholinosulfonyl)phenyl)urea;
4-(3-(3-((4-butylpiperazin-1-yl)(imino)methyl)phenyl) ureido)-N -(7-chloroquinolin-4-yl)benzenesulfonamide;
4-(3-(3-((4-butylpiperazin-1-yl)(imino)methyl)phenyl) ureido)-N -(4- sulfamoylphenyl)benzenesulfonamide;
methyl 4-(imino(3-(3-(4-(N-(4-sulfamoylphenyl)sulfamoyl)phenyl)ureido)phenyl)methyl)piperazine-1-carboxylate;
4-(3-(3-(imino(morpholino)methyl)phenyl)ureido)-N-(4-sulfamoylphenyl)benzenesulfonamide;
4-(3-(3-(imino(4-methylpiperazin-1-yl)methyl)phenyl) ureido)-N -(4-sulfamoylphenyl)benzenesulfonamide;
4-(3-(3-(imino(4-oxopiperidin-1-yl)methyl)phenyl)ureido)-N-(4-sulfamoylbenzyl)benzenesulfonamide;
4-(3-(3-((4-(2-hydroxyethyl)piperazin-1-yl) (imino)methyl)phenyl)ureido)-N-(4-sulfamoylbenzyl)benzenesulfonamide;
4-(3-(3-((4-(hydroxymethyl)piperidin-1-yl) (imino)methyl)phenyl)ureido)-N- (4-sulfamoylbenzyl)benzenesulfonamide;
N-ethyl-N-(2-hydroxyethyl)-3-(3-(4-(N-(4-sulfamoylbenzyl) sulfamoyl)phenyl)ureido)benzimidamide;
4-(3-(3-(imino(thiomorpholino)methyl)phenyl)ureido)-N-(4-sulfamoylbenzyl)benzenesulfonamide;
N,N-bis(2-methoxyethyl)-3-(3-(4-(N-(4-sulfamoylbenzyl)sulfamoyl)phenyl)ureido)benzimidamide;
1-(imino(3-(3-(4-(N-(4-sulfamoylbenzyl)sulfamoyl) -phenyl)ureido)phenyl)methyl)piperidine-4-carboxamide;
4-(3-(3-((4-butylpiperazin-1-yl)(imino)methyl)phenyl) ureido)-N -(4-sulfamoylbenzyl)benzenesulfonamide;
4-(3-(3-((4-butylpiperazin-1-yl)(imino)methyl)phenyl) ureido)-N -(2,3,6-trifluorobenzyl)benzenesulfonamide;
N-benzyl-4-(3-(3-((4-butylpiperazin-1-yl)(imino)methyl) phenyl)ureido)benzenesulfonamide;
4-(3-(3-((4-ethylpiperazin-1-yl)(imino)methyl)phenyl) ureido)-N -(4-sulfamoylbenzyl)benzenesulfonamide;
4-(3-(3-(imino(4-propylpiperazin-1-yl)methyl)phenyl) ureido)-N -(4-sulfamoylbenzyl)benzenesulfonamide;
4-(3-(3-((4-allylpiperazin-1-yl)(imino)methyl)phenyl) ureido)-N -(4-sulfamoylbenzyl)benzenesulfonamide;
4-(2-(4-(3-(3-((4-butylpiperazin-1-yl)(imino)methyl)phenyl)ureido)phenylsulfonyl)hydrazinyl)benzenesulfonamide;

2-(4-(3-(3-((4-butylpiperazin-1-yl)(imino)methyl)phenyl)ureido)phenylsulfonyl)isoindoline-5-sulfonamide;

4-(3-(3-((4-butylpiperazin-1-yl)(imino)methyl)phenyl)ureido)-N -(1-(4-sulfamoylphenyl)ethyl)benzenesulfonamide;

4-(3-(3-(imino(morpholino)methyl)phenyl)ureido)-N-(4-sulfamoylbenzyl)benzenesulfonamide;

4-(3-(3-(((1,1-dioxidothiomorpholino)(imino)methyl)phenyl)ureido)-N -(4-sulfamoylbenzyl)benzenesulfonamide;

4-(3-(3-(imino(4-(pyridin-4-ylmethyl)piperazin-1-yl)methyl)phenyl)ureido)-N-(4-sulfamoylbenzyl)benzenesulfonamide;

4-(3-(3-(imino(pyrrolidin-1-yl)methyl)phenyl)ureido)-N-(4-sulfamoylbenzyl)benzenesulfonamide;

N-(2-(diethylamino)ethyl)-N-methyl-3-(3-(4-(N-(4-sulfamoylbenzyl)sulfamoyl)phenyl)ureido)benzimidamide;

4-(3-(3-((4-hydroxypiperidin-1-yl)(imino)methyl)phenyl)ureido)-N-(4-sulfamoylbenzyl)benzenesulfonamide;

4-(3-(3-((3-(dimethylamino)pyrrolidin-1-yl) (imino)methyl)phenyl)ureido)-N-(4-sulfamoylbenzyl)benzenesulfonamide;

4-(3-(3-(imino(2-(pyrrolidin-1-ylmethyl)pyrrolidin-1-yl)methyl)phenyl)ureido)-N-(4-sulfamoylbenzyl)benzenesulfonamide;

tert-butyl 4-(imino(3-(3-(4-(N-(4-sulfamoylbenzyl) sulfamoyl)phenyl)ureido)phenyl)methyl)piperazine-1-carboxylate;

4-(3-(3-(imino(piperazin-1-yl)methyl)phenyl)ureido)-N-(4-sulfamoylbenzyl)benzenesulfonamide;

4-(3-(3-(imino(4-methylpiperazin-1-yl)methyl)phenyl)ureido)-N -(4-sulfamoylbenzyl)benzenesulfonamide;

4-(3-(3-(imino(4-isopropylpiperazin-1-yl)methyl)phenyl)ureido) -N-(4-sulfamoylbenzyl)benzenesulfonamide;

4-(3-(3-(imino(4-pentylpiperazin-1-yl)methyl)phenyl)ureido)-N -(4-sulfamoylbenzyl)benzenesulfonamide;

4-(3-(3-((4-heptylpiperazin-1-yl)(imino)methyl)phenyl)ureido) -N-(4-sulfamoylbenzyl)benzenesulfonamide;

4-(3-(3-((4-acetylpiperazin-1-yl)(imino)methyl)phenyl)ureido) -N-(4-sulfamoylbenzyl)benzenesulfonamide;

4-(3-(3-(imino(4-propionylpiperazin-1-yl)methyl)phenyl)ureido) -N-(4-sulfamoylbenzyl)benzenesulfonamide;

4-(3-(3-(imino(4-pentanoylpiperazin-1-yl)methyl)phenyl)ureido) -N-(4-sulfamoylbenzyl)benzenesulfonamide;

methyl 4-(imino(3-(3-(4-(N-(4-sulfamoylbenzyl)sulfamoyl)phenyl)ureido)phenyl)methyl)piperazine-1-carboxylate;

ethyl 4-(imino(3-(3-(4-(N-(4-sulfamoylbenzyl)sulfamoyl)phenyl)ureido)phenyl)methyl)piperazine-1-carboxylate;

propyl 4-(imino(3-(3-(4-(N-(4-sulfamoylbenzyl)sulfamoyl)phenyl)ureido)phenyl)methyl)piperazine-1-carboxylate;

4- (3- (3-((4-butyl-3-oxopiperazin-1-yl) (imino)methyl)phenyl)ureido)-N-(4-sulfamoylbenzyl)benzenesulfonamide;

N,N-dimethyl-3-(3-(4-(N-(4-sulfamoylbenzyl)sulfamoyl)phenyl)ureido)benzimidamide;

4-(3-(3-((4-(2-cyanoethyl)piperazin-1-yl)(imino)methyl)phenyl)ureido)-N-(4-sulfamoylbenzyl)benzenesulfonamide;

4-(3-(3-((4-(cyclopropylmethyl)piperazin-1-yl)(imino)methyl)phenyl)ureido)-N-(4-sulfamoylbenzyl)benzenesulfonamide;

4-(3-(3-((4-((1,3-dioxolan-2-yl)methyl)piperazin-1-yl)(imino)methyl)phenyl)ureido)-N-(4- sulfamoylbenzyl)benzenesulfonamide;

4-(3-(3-(imino(4-((tetrahydrofuran-2-yl)methyl)piperazin-1-yl)methyl)phenyl)ureido)-N-(4-sulfamoylbenzyl)benzenesulfonamide;

4-(3-(3-(imino(4-(2-methoxyethyl)piperazin-1-yl)methyl)phenyl)ureido)-N-(4-sulfamoylbenzyl)benzenesulfonamide;

5-((4-(3-(3-((4-butylpiperazin-1-yl)(imino)methyl)phenyl)ureido)phenylsulfonamido)methyl)thiophene-2-sulfonamide;

4-(3-(4-((4-butylpiperazin-1-yl)(imino)methyl)phenyl)ureido)-N -(4-sulfamoylbenzyl)benzenesulfonamide;

methyl 4-((acetylimino)(3-(3-(4-(N-(4-sulfamoylbenzyl)sulfamoyl)phenyl)ureido)phenyl)methyl)piperazine-1-carboxylate;

methyl 4-((octanoylimino)(3-(3-(4-(N-(4-sulfamoylbenzyl)sulfamoyl)phenyl)ureido)phenyl)methyl)piperazine-1-carboxylate; or methyl 4-((hydroxyimino)(4-(3-(4-(N-(4-sulfamoylbenzyl)sulfamoyl)phenyl)ureido)phenyl)methyl)piperazine-1-carboxylate.

23. A compound according to claim 22, or a physiologically acceptable salt thereof.

24. A method of treating or preventing or ameliorating malaria in a subject, comprising administering an effective amount of a compound according to claim 22 to said subject.

* * * * *